US008329188B2

(12) United States Patent
Moyle et al.

(10) Patent No.: US 8,329,188 B2
(45) Date of Patent: Dec. 11, 2012

(54) HUMAN M2E PEPTIDE IMMUNOGENS

(75) Inventors: Matthew Moyle, Redmond, WA (US); Jennifer Mitcham, Redmond, WA (US)

(73) Assignee: Theraclone Sciences, Inc., Seattle, WA (US)

( * ) Notice: Subject to any disclaimer, the term of this patent is extended or adjusted under 35 U.S.C. 154(b) by 136 days.

(21) Appl. No.: 12/617,243

(22) Filed: Nov. 12, 2009

(65) Prior Publication Data
US 2010/0135955 A1 Jun. 3, 2010

Related U.S. Application Data

(60) Provisional application No. 61/113,880, filed on Nov. 12, 2008.

(51) Int. Cl.
*A61K 39/12* (2006.01)
(52) U.S. Cl. .................. 424/186.1; 424/209.1; 530/300
(58) Field of Classification Search .................. None
See application file for complete search history.

(56) References Cited

U.S. PATENT DOCUMENTS

| 4,033,940 | A | 7/1977 | Hughes et al. |
|---|---|---|---|
| 4,102,877 | A | 7/1978 | Nutt |
| 4,816,567 | A | 3/1989 | Cabilly et al. |
| 5,057,540 | A | 10/1991 | Kensil et al. |
| 5,500,362 | A | 3/1996 | Robinson et al. |
| 5,641,870 | A | 6/1997 | Rinderknecht et al. |
| 5,821,337 | A | 10/1998 | Carter et al. |
| 6,090,388 | A | 7/2000 | Wang |
| 6,207,646 | B1 | 3/2001 | Krieg et al. |
| 2006/0115489 | A1* | 6/2006 | Birkett et al. ............. 424/189.1 |

FOREIGN PATENT DOCUMENTS

| EP | 404097 A2 | 12/1990 |
|---|---|---|
| WO | WO-9219265 A1 | 11/1992 |
| WO | WO-9311161 A1 | 6/1993 |
| WO | WO-9313302 A1 | 7/1993 |
| WO | WO-0018434 A1 | 4/2000 |
| WO | WO-02098368 A2 | 12/2002 |
| WO | WO-02098369 A2 | 12/2002 |
| WO | WO 2006/061723 * | 6/2006 |
| WO | WO-2007031550 A2 | 3/2007 |

OTHER PUBLICATIONS

De Filette et al., Universal influenza A vaccine: Optimization of M2-based constructs, 2005, Virology, vol. 337, pp. 149-161.*
Wu et al., Humanization of a Murine Monoclonal ntibody by Simultaneous Optimization of Framework and DDR Residues, 1999, Journal of Molecular Biology, vol. 294, pp. 151-162.*
Feng et al. "Influenza A Virus Infection Engenders a Poor Antibody Response Against the Ectodomain of Matrix Protein 2." *Virol. J.* 3.102(2006).
Altschul et al., "Basic Local Alignment Search Tool", *J. Mol. Biol.*, 215:403-410 (1990).
Altschul et al., "Gapped BLAST and PSI-BLAST: a new generation of protein database search programs", *Nucl. Acids Res.*, 25:3389-3402 (1977).
Camarero et al., "Biosynthesis of a Head-to-Tail Cyclized Protein with Improved Biological Activity", *J. Am. Chem. Soc.*, 121:5597-5598 (1999).
Camarero et al., "Chemical Synthesis of a Circular Protein Domain: Evidence for Folding-Assisted Cyclization", *Angew. Chem. Int. Ed.*, 37(3):347-349 (1998).
Camerero et al., "Chemoselective backbone cyclization of unprotected peptides", *Chem. Commun.*, 15:1369-1370 (1997).
Capel et al., "Heterogeneity of Human IgG Fc Receptors", *Immunomethods*, 4:25-34 (1994).
Chothia et al., "Canonical Structures for the Hypervariable Regions of Immunoglobulins", *J. Mol. Biol.*, 196:901-917 (1987).
Chothia et al., "Conformations of immunoglobulin hypervariable regions", *Nature*, 342:877-883 (1989).
Ciampor et al., "Regulation of pH by the M2 protein of influenza A viruses", *Virus Res.*, 22(3):247-258 (1992).
Clackson et al., "Making antibody fragments using phage display libraries", *Nature*, 352:624-628 (1991).
Clynes et al., "Fc receptors are required in passive and active immunity to melanoma", *Proc. Natl. Acad. Sci. U.S.A.*, 95:652-656 (1998).
Cox et al., "Adjuvants—a classification and review of their modes of action", *Vaccine*, 15(3):248-256 (1997).
Daeron, M., "Fc Receptor Biology", *Ann. Rev. Immunol.*, 15:203-234 (1997).
Dalum et al., "Therapeutic antibodies elicited by immunization against TNF-α", *Nature Biotechnol.*, 17(7):666-669 (1999).
Dayhoff, M.O., "A model of evolutionary change in proteins—Matrices for detecting distant relationships", in *Atlas of Protein Sequence and Structure*, National Biomedical Research Foundation, Washington, DC, 5(Suppl. 3) pp. 345-358 (1978).
de Haas et al., "Fcγ receptors of phagocytes" *J. Lab. Clin. Med.*, 126:330-341 (1995).
Devlin et al., "Random Peptide Libraries: A Source of Specific Protein Binding Molecules", *Science*, 249(4967):404-406 (1990).
Evans et al., "The Cyclization and Polymerization of Bacterially Expressed Proteins Using Modified Self-Splicing Inteins", *J. Biol. Chem.*, 274(26):18359-18363 (1999).
Frace et al., "Modified M2 proteins produce heterotypic immunity against influenza A virus", *Vaccine*, 17(18):2237-2244 (1999).
Furka et al., "General method for rapid synthesis of multicomponent peptide mixtures", *Int. J. Pept. Protein Res.* 37(6):487-493 (1991).
Gazzano-Santoro et al., "A non-radioactive complement-dependent cytotoxicity assay for anti-CD20 monoclonal antibody", *J. Immunol. Meth.*, 202:163-171 (1996).
Geysen et al., "*A Priori* Delineation of a Peptide Which Mimics a Discontinuous Antigenic Determinant", *Mol. Immunol.*, 23(7):709-715 (1986).

(Continued)

*Primary Examiner* — Benjamin P Blumel
(74) *Attorney, Agent, or Firm* — Mintz Levin Cohn Ferris Glovsky and Popeo, P.C.; Ivor R. Elrifi; Katherine J. Miller

(57) ABSTRACT

The present invention provides novel peptide immunogens comprising influenza virus matrix 2 protein epitopes and related compositions and methods. The present invention relates to a composition comprising a peptide immunogen useful for the prevention and treatment of an influenza virus-mediated disease. The invention also relates to vaccines, immunogenic products and immunogenic compositions containing the peptide immunogens.

7 Claims, 8 Drawing Sheets

OTHER PUBLICATIONS

Geysen et al., "The delineation of peptides able to mimic assembled epitopes", in *Synthetic peptides as antigens*, Wiley, Chichester, Ciba Foundation Symposium 119, pp. 130-149 (1986).

Goebel et al., "Studies on Antibacterial Immunity Induced by Artificial Antigens", *J. Exp. Med.*, 69:353-364 (1939).

Goldenburg et al., "Circular and Circularly Permuted Forms of Bovine Pancreatic Trypsin Inhibitor", *J. Mol. Biol.*, 165:407-413 (1983).

Grambas et al., "Maturation of Influenza A Virus Hemagglutinin—Estimates of the pH Encountered during Transport and its Regulation by the M2 Protein", *Virology*, 190:11-18 (1992).

Guyer et al., "Immunoglobin Binding by Mouse Intestinal Epithelial Cell Receptors", *J. Immunol.*, 117(2):587-593 (1976).

Hein, J., "Unified Approach to Alignment and Phylogenes", *Meth. Enzymol.*, 183:626-645 (1990).

Henikoff et al., "Amino acid substitution matrices from protein blocks", *Proc. Nat'l. Acad. Sci. U.S.A.*, 89:10915-10929 (1989).

Higgins et al., "Fast and sensitive multiple sequence alignments on a microcomputer", *CABIOS*, 5:151-153 (1989).

Holliger et al., "'Diabodies': Small bivalent and bispecific antibody fragments", *Proc. Natl. Acad. Sci. U.S.A.*, 90:6444-6448 (1993).

Ito et al., "Evolutionary Analysis of the Influenza A Virus M Gene with Comparison of the M1 and M2 Proteins", *J. Virology*, 65(10):5491-5498 (1991).

Iwai et al., "Circular β-lactamase: stability enhancement by cyclizing the backbone", *FEBS Lett.*, 459(2):166-172 (1999).

Jackson et al., "Enzymatic Cyclization of Linear Peptide Esters Using Subtiligase", *J. Am. Chem. Soc.*, 117:819-820 (1995).

Jones et al., "Replacing the complementarity-determining regions in a human antibody with those from a mouse", *Nature*, 321:522-525 (1986).

Kim et al., "Localization of the site of the murine IgG1 molecule that is involved in binding to the murine intestinal Fc receptor", *Eur. J. Immunol.*, 24:2429-2434 (1994).

Kohler et al., "Continuous cultures of fused cells secreting antibody of predefined specificity", *Nature*, 256:495-497 (1975).

Lam et al., "A new type of synthetic peptide library for identifying ligand-binding activity", *Nature*, 354(6348):82-84 (1991).

Le et al., "Avian Flu: Isolation of Drug-Resistant H5N1 Virus", *Nature*, 437(7062):1108 (2005).

Lipatov et al., "Influenza: Emergence and Control", *Virology*, 78(17):8951-8959 (2004).

Manning et al., "Stability of Protein Pharmaceuticals", *Pharm. Res.*, 6(11):903-918 (1989).

Marks et al., "By-passing Immunization. Human Antibodies from V-gene Libraries Displayed of Phage", *J. Mol. Biol.*, 222:581-597 (1991).

Merrifield et al., "Solid Phase Synthesis (Nobel Lecture)", *Angew Chem.*, 24:799-810 (1985).

Moore, M. L., "Peptide Design Considerations", in *Synthetic Peptides: A User's Guide*, Ed. Grant, WH Freeman and Company, New York, NY, Ch. 2, pp. 63-67 (1992).

Morrison et al., "Chimeric human antibody molecules: Mouse antigen-binding domains with human constant region domains", *Proc. Nat'l. Acad. Sci. U.S.A.*, 81:6851-6855 (1984).

Muller, R., "Determination of Affinity and Specificity of Anti-Hapten Antibodies by Competitive Radioimmunoassay", *Meth. Enzymol.*, 92:589-601 (1983).

Myers et al., "Optimal alignments in linear space", *CABIOS*, 4(1):11-17 (1988).

Needleman et al., "A General Method Applicable to the Search for Similarities in the Amino Acid Sequence of Two Proteins", *J. Mol. Biol.*, 48:443-453 (1970).

Neirynck et al., "A universal influenza A vaccine based on the extracellular domain of the M2 protein", *Nature Med.*, 5(10):1157-1163 (1999).

Osterholm et al., "Preparing for the Next Pandemic", *N. E. J. Med.*, 352:1839-1842(2005).

Pearson et al., "Improved tools for biological sequence comparison" *Proc. Natl. Acad. Sci. U.S.A.*, 85:2444-2448 (1988).

Pluckthun, "Antibodies from *Escherichia coli*" in *The Pharmacology of Monoclonal Antibodies*, Rosenburg and Moore, Eds., 113:269-315 (1994).

Presta, "Antibody engineering", *Curr. Op. Struct. Biol.*, 2:593-596 (1992).

Ravetch et al., "Fc Receptors", *Ann. Rev. Immunol.*, 9:457-492 (1991).

Riechmann et al., "Reshaping human antibodies for therapy", *Nature*, 332:323-329 (1988).

Robinson, D. F., "Comparison of Labeled Trees with Valency Three", *J. Comb. Theor.*, 11:105-119 (1971).

Saitou et al, "The Neighbor-joining Method: A New Method for Reconstructing Phylogenetic Trees", *Mol. Biol. Evol.*, 4:406-425 (1987).

Scatchard, G., "The Attractions of Proteins for Small Molecules and Ions", *Ann. N.Y. Acad. Sci. U.S.A.*, 51:660-672 (1949).

Schneerson et al., "Serum Antibody Responses of Juvenile and Infant Rhesus Monkeys Injected with Haemophilus influenzae Type b and *Pneumococcus* Type 6A Capsular Polysaccharide-Protein Conjugates", *Infect. Immun.*, 45(3):582-591 (1984).

Schutze et al., "Carrier-induced epitopic suppression, a major issue for future synthetic vaccines", *J Immunol.*, 135(4):2319-2322 (1985).

Scott et al., "Production of cyclic peptides and proteins in vivo", *Proc. Natl. Acad. Sci. U.S.A.*, 96(24):13638-13643 (1999).

Scott et al., "Searching for Peptide Ligands with an Epitope Library", *Science*, 249(4967):386-390 (1990).

Slepushkin et al., "Protection of mice against influenza A virus challenge by vaccination with baculovirus-expressed M2 protein", *Vaccine*, 13(15):1399-1402 (1995).

Smith et al., "Comparison of Biosequences", Adv. Applied Math., 2:482-489 (1981).

Sugrue et al., "Specific structural alteration of the influenza haemagglutinin by amantadine", *EMBO J.*, 9(11):3469-3476 (1990).

Tam et al., "A biomimetic strategy in the synthesis and fragmentation of cyclic protein", *Prot. Sci.*, 7(7): 1583-1592 (1998).

Verhoeyen et al., "Reshaping Human Antibodies: Grafting an Antilysozyme Activity", *Science*, 239:1534-1536 (1988).

Wilbur et al., "Rapid similarity searches of nucleic acid and protein data banks", *Proc. Nat'l. Acad. Sci. U.S.A.*, 80:726-730 (1983).

Wood et al., "A genetic system yields self-cleaving inteins for bioseparations", *Nat. Biotechnol.*, 17(9):889-892 (1999).

Wu et al., "Protein *trans*-splicing by a split intein encoded in a split DnaE gene of *Synechocystis* sp. PCC6803", *Proc. Natl. Acad. Sci. U.S.A.*, 95(16):9226-9231 (1998).

Zapata et al., "Engineering linear F(ab')$_2$ fragments for efficient production in *Escheticha coli* and enhanced antiproliferative activity", *Protein Eng.*, 8(10):1057-1062 (1995).

Zhang et al., "Synthesis and Application of Unprotected Cyclic Peptides as Building Blocks for Peptide Dendrimers", *J. Am. Chem. Soc.*, 119(10):2363-2370 (1997).

De Filette et al. "Improved design of intranasal delivery of an M2e-based human influenza A vaccine." Vaccine, vol. 24, No. 44-46, pp. 6597-6601. Nov. 10, 2006.

Eliasson et al. "CTA1-M2e-DD: A novel mucosal adjuvant targeted influence vaccine." Vaccine, vol. 26, No. 9, pp. 1243-1252. Jan. 10, 2008.

Fiers et al. "M2e-based universal influenza A vaccine." Vaccine, vol. 27, No. 45, pp. 6280-6283. Oct. 23, 2009.

Huleatt et al. "Potent immunogenicity and efficacy of a universal influenza vaccine candidate comprising a recombinant fusion protein linking influenza M2e to the TLR5 ligand flagellin." Vaccine, vol. 26, No. 2, pp. 201-214. Jan. 10, 2008.

Liu et al. "N-terminus of M2 protein could induce antibodies with inhibitory activity against influenza virus replication." FEMS Immunology and Medical Microbiology, vol. 35, No. 2, pp. 141-146. Mar. 20, 2003.

Liu et al. "High epitope density in a single protein molecule significantly enhances antigenicity as well as immunogenicity: a novel strategy for modern vaccine development and a preliminary investigation about B cell discrimination of monomeric proteins." European Journal of Immunology, vol. 35, No. 2, pp. 505-514. Feb. 2005.

Mozdzanowska et al. "Roles of adjuvant and route of vaccination in antibody response and protection engendered by a synthetic matrix protein-2-based influenza A virus vaccine in the mouse." Virology Journal, vol. 4, p. 118. 2007.

Wang et al. "Therapeutic potential of a fully human monoclonal antibody against influenza A virus M2 protein." Antiviral Research, vol. 80, No. 2, pp. 168-177. Jun. 2008.

Wang et al. "Monoclonal antibody recognizing SLLTEVET epitope of M2 protein potently inhibited the replication of influenza A viruses in MDCK cells." Biochemical and Biophysical Research Communications, vol. 385, No. 1, pp. 118-122. Jul. 17, 2009.

Wu et al. "Characterization of immunity induced by M2e of influenza virus." Vaccine, vol. 25, No. 52, pp. 8868-8873. Oct. 22, 2007.

Wu et al. "Heterosubtypic protection conferred by combined vaccination with M2e peptide and split influenza vaccine." Vaccine, vol. 27, No. 43, pp. 6095-6101. Oct. 9, 2009.

Zhang et al. "Fine specificity and sequence of antibodies directed against the ectodomain of matrix protein 2 of influenza A virus." Molecular Immunology, vol. 43, No. 14, pp. 2195-2206. Jul. 2006.

* cited by examiner

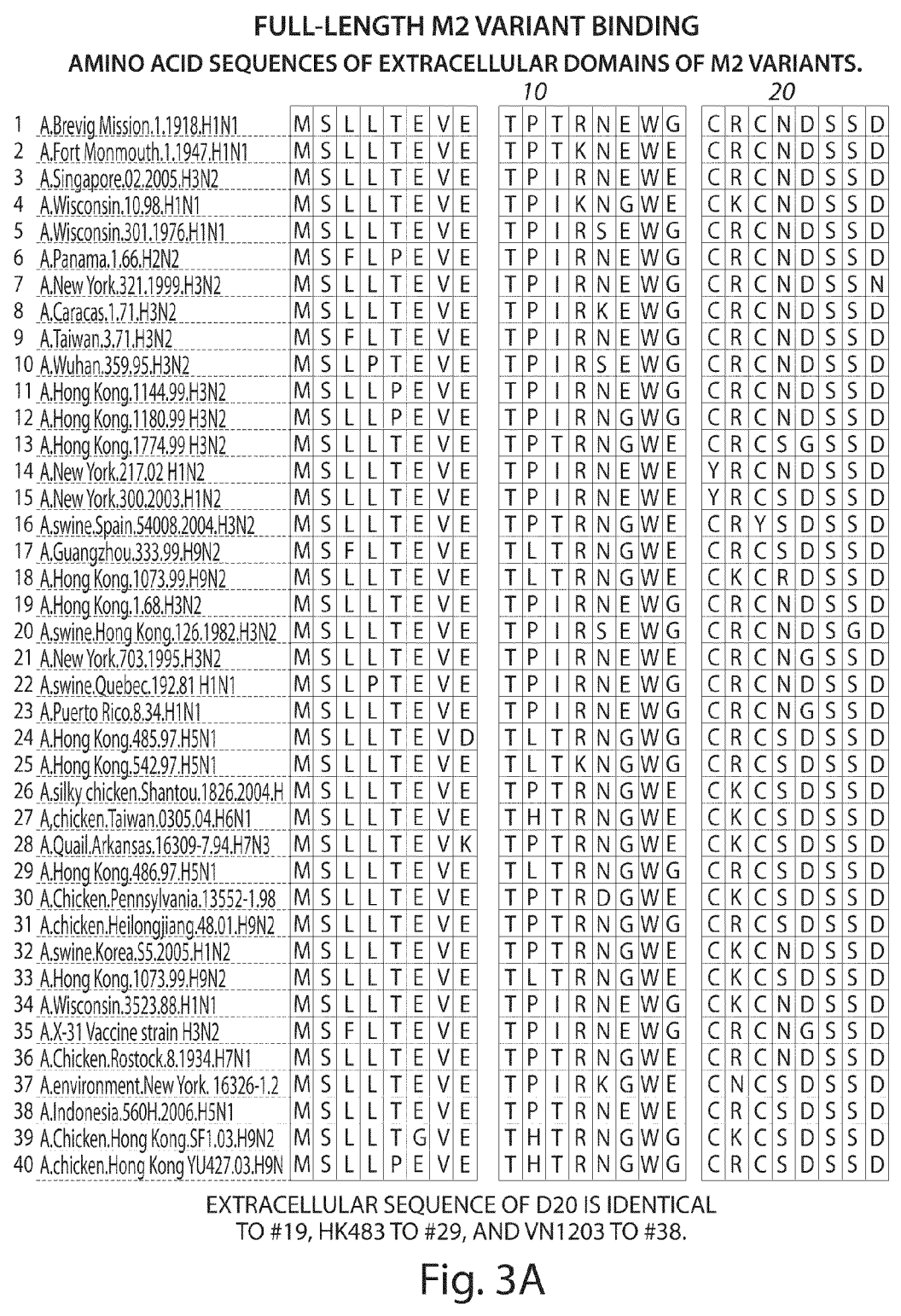

FULL-LENGTH M2 VARIANT BINDING
AMINO ACID SEQUENCES OF EXTRACELLULAR DOMAINS OF M2 VARIANTS.

| # | Strain | 1 | 2 | 3 | 4 | 5 | 6 | 7 | 8 | 9 | 10 | 11 | 12 | 13 | 14 | 15 | 16 | 17 | 18 | 19 | 20 | 21 | 22

CORE SEQUENCES - 1:

| S | L | L | T | E |
|---|---|---|---|---|
| C | A | A | - | D |
| T | C | C |   | C |
|   | F | E |   |   |
|   | K | F |   |   |
|   |   | I |   |   |
|   |   | K |   |   |
|   |   | M |   |   |
|   |   | Q |   |   |
|   |   | S |   |   |
|   |   | T |   |   |
|   |   | V |   |   |

PREFERRED CORE SEQUENCE SHOWN IN BOX; ALLOWABLE VARIANT RESIDUES SHOWN AT EACH POSITION

Fig. 6A

CORE SEQUENCES - 2:

| S | L | L | T | E |
|---|---|---|---|---|
| A | A | B | M | A |
| C | C |   | N | D |
| D | F |   | Q | F |
| L | H |   | S | H |
| T | I |   | W | I |
| V | K |   |   | K |
|   | M |   |   | M |
|   | N |   |   | N |
|   | Q |   |   | Q |
|   | R |   |   | S |
|   | T |   |   | W |
|   | W |   |   | Y |
|   | Y |   |   | C |

PREFERRED CORE SEQUENCE SHOWN IN BOX; ALLOWABLE VARIANT RESIDUES SHOWN AT EACH POSITION; B=ANY RESIDUE

Fig. 6B

CORE VARIANTS:

| S | L | L | T | E |   |   | SEQ ID NO: 47 |
| S | L | L | T | E | X |   | SEQ ID NO: 1597 |
| S | L | L | T | E | X | Z | SEQ ID NO: 1598 |

WHERE X IS ANY AMINO ACID BUT PREFERABLY = V OR C
WHERE Z IS ANY AMINO ACID BUT PREFERABLY = E

Fig. 6C

IMMUNOGENS (LINEAR & CYCLIZED PEPTIDES):

(CORE)
(CORE)G(CORE)
(CORE)G(CORE)G(CORE)
(CORE)G(CORE)G(CORE)G(CORE)
(CORE)G(CORE)G(CORE)G(CORE)G(CORE)

Fig. 6D

IMMUNOGENS (LINEAR & CYCLIZED PEPTIDES):

J(CORE)
J(CORE)G(CORE)
J(CORE)G(CORE)G(CORE)
J(CORE)G(CORE)G(CORE)G(CORE)
J(CORE)G(CORE)G(CORE)G(CORE)G(CORE)

WHERE J IS ANY AMINO ACID BUT PREFERABLY = C

Fig. 6E

SPECIFIC IMMUNOGENS (LINEAR & CYCLIZED PEPTIDES):

| | |
|---|---|
| SLLTEVGSLLTEV | SEQ ID NO: 320 |
| CSLLTEVGSLLTEV | SEQ ID NO: 283 |
| CSLLTECGSLLTCV | SEQ ID NO: 463 |

Fig. 6F

HUMAN M2E PEPTIDE IMMUNOGENS

RELATED APPLICATIONS

This application is related to provisional application U.S. Ser. No. 61/113,880, filed Nov. 12, 2008, the contents of which are herein incorporated by reference in their entirety.

FIELD OF THE INVENTION

The present invention relates generally to vaccines and therapeutics for influenza virus infection. The invention specifically relates to peptide immunogens suitable for generating influenza matrix 2 protein-specific antibodies and their manufacture and use.

BACKGROUND OF THE INVENTION

Influenza virus infects 5-20% of the population and results in 30,000-50,000 deaths each year in the U.S. Although the influenza vaccine is the primary method of infection prevention, four antiviral drugs are also available in the U.S.: amantadine, rimantadine, oseltamivir and zanamivir. As of December 2005, only oseltamivir (TAMIFLU™) is recommended for treatment of influenza A due to the increasing resistance of the virus to amantadine and rimantadine resulting from an amino acid substitution in the M2 protein of the virus. Recently, a drug resistant avian virus was found in a 14-year-girl in Viet Nam. Resistance to Tamiflu has also been found in human influenza as well (Mai Le et al., Nature 437:1108 (2005)).

Influenza vaccines have been demonstrated to have a protective effect against influenza infection. However, yearly emerging antigenic variants of influenza viruses necessitate surveillance to contemporary of circulating virus strains. In some cases, difficulty in the prediction of new variant strains has prevented the timely production of the vaccine (Frace et al., Vaccine 17:2237 (1999)). Recently, pandemic avian influenza has become a serious threat due to the emergence of avian influenza viruses such as $H5N_1$ in southern Asia. The currently available vaccines would be ineffective against avian viruses (Lipatov et al., J. Virology 78:8951 (2004); Osterholm et al., N Engl. Med. 352:1839 (2005)). A third problem with the current vaccine is the ineffectiveness in certain populations with compromised immune systems, for instance premature infants, the elderly, AIDS and transplant patients.

Disease caused by influenza A viral infections is typified by its cyclical nature. Antigenic drift and shift allow for different A strains to emerge every year. Added to that, the threat of highly pathogenic strains entering into the general population has stressed the need for novel therapies for flu infections.

SUMMARY OF THE INVENTION

The present invention relates to a synthetic peptide immunogen capable of inducing antibodies against a M2e target peptide of influenza A virus. In particular, the peptide immunogen of this invention comprises one or more epitopes. Optionally, the peptide immunogen further comprises a general immune stimulator. These peptide immunogens of the present invention are effective, capable of inducing antibodies against influenza A virus to prevent infection by the virus.

The peptide immunogen of this invention is represented by the following formula: $[Xaa_0]_m$-$Xaa_1$-$Xaa_2$-$Xaa_3$-$Xaa_4$-$Xaa_5$-$[Xaa_6]_p$-$[Xaa_7]_q$-$[Xaa_8]$-$[Xaa_0]_m$-$Xaa_1$-$Xaa_2$-$Xaa_3$-$Xaa_4$-$Xaa_5$-$[Xaa_6]_p$-$[Xaa_7]_q]_n$; wherein, m, p and q are independently 0 or 1, n is any number between 0 and 4, $Xaa_0$ is any amino acid, preferably C; $Xaa_6$ is any amino acid, preferably V or C; $Xaa_7$ is any amino acid, preferably E; $Xaa_8$ is any amino acid not including proline, preferably G or A; $Xaa_1$-$Xaa_2$-$Xaa_3$-$Xaa_4$-$Xaa_5$- is S-L-L-T-E or, a peptide having a single substitution to the sequence S-L-L-T-E (SEQ ID NO: 47), the substitution selected from the group consisting of: $Xaa_1$ is C or T; $Xaa_2$ is A, C, F or K, $Xaa_3$ is A, C, E, F, I, K, M, Q, S, T or V, and $Xaa_5$ is D or C.

In another aspect the peptide immunogen of this invention is represented by the following formula: $[Xaa_0]_m$-$Xaa_1$-$Xaa_2$-$Xaa_3$-$Xaa_4$-$Xaa_5$-$[Xaa_6]_p$-$[Xaa_7]_q$-$[Xaa_8]$-$[Xaa_0]_m$-$Xaa_1$-$Xaa_2$-$Xaa_3$-$Xaa_4$-$Xaa_5$-$[Xaa_6]_p$-$[Xaa_7]_q]_n$; wherein, m, p and q are independently 0 or 1, n is any number between 0 and 4, $Xaa_0$ is any amino acid, preferably C; $Xaa_6$ is any amino acid, preferably V or C; $Xaa_7$ is any amino acid, preferably E; $Xaa_8$ is any amino acid not including proline, preferably G or A; $Xaa_1$-$Xaa_2$-$Xaa_3$-$Xaa_4$-$Xaa_5$- is S-L-L-T-E or, a peptide having a single substitution to the sequence S-L-L-T-E (SEQ ID NO: 47), the substitution selected from the group consisting of: $Xaa_1$ is A, C, D, L, T or V, $Xaa_2$ is A, C, F, H, I, K, M, N, Q, R, T, W, or Y, $Xaa_3$ is any amino acid, $Xaa_4$ is M, N, Q, S, or W, and $Xaa_5$ is A, D, F, H, I, K, M, N, Q, S, W, Y, or C.

In some aspects of the inventions, one or more amino acids are D-amino acids.

In some aspects of the inventions, the peptide immunogens are cyclic. Cyclization of peptide immunogens can be performed by cross-linking cysteine residues present in the peptide or by chemical means.

In some aspects of the inventions, the peptide immunogens are conjugated to carrier proteins such as KLH through intermolecular crosslinking.

The invention relates to compositions comprising the peptide immunogen and a pharmaceutically acceptable adjuvant and/or carrier selected from the group consisting of alum, liposyn, saponin, squalene, L121, emulsigen monophosphyryl lipid A (MPL), polysorbate 80, QS21, Montanide ISA51, ISA35, ISA206 and ISA 720.

The invention relates to preventing or treating a disease associated with influenza virus infection by administering compositions comprising the peptide immunogens of the invention.

The invention relates to methods for generating antibodies reactive to influenza matrix 2 (M2) protein by administering compositions comprising the peptide immunogens of the invention. It is an object of the invention to develop an immunogen that will enable the generation of high levels of high affinity antibodies against M2 protein.

One aspect of this invention provides a vaccine comprising an immunologically effective amount of a peptide immunogen composition in accordance with this invention and one or more pharmaceutically acceptable carriers. The vaccine when administered at an appropriate dosage will generate immunotherapeutic antibodies directed against influenza A virus.

The present invention provides a vaccine delivery vehicle that is suitable for human or veterinary use for the prophylaxis and treatment of influenza.

The present invention and other objects, features, and advantages of the present invention will become further apparent in the following Detailed Description of the invention and the accompanying figures and embodiments.

BRIEF DESCRIPTION OF THE DRAWINGS

FIG. 3A is a chart showing amino acid sequences of extracellular domains of M2 variants.

FIGS. 6A and 6B are schematic diagrams that depict a core peptide immunogen and amino acid variants that are effective in binding anti-M2e huMAbs 8I10 and 23K12 under high (6A) and low (6B) stringency conditions.

FIG. 6C is a schematic diagram that depicts variants of the core sequence.

FIGS. 6D, 6E and 6F are schematic diagrams that depict specific linear and cyclized peptide immunogens containing the core sequences of the invention.

DETAILED DESCRIPTION

Figure 1:
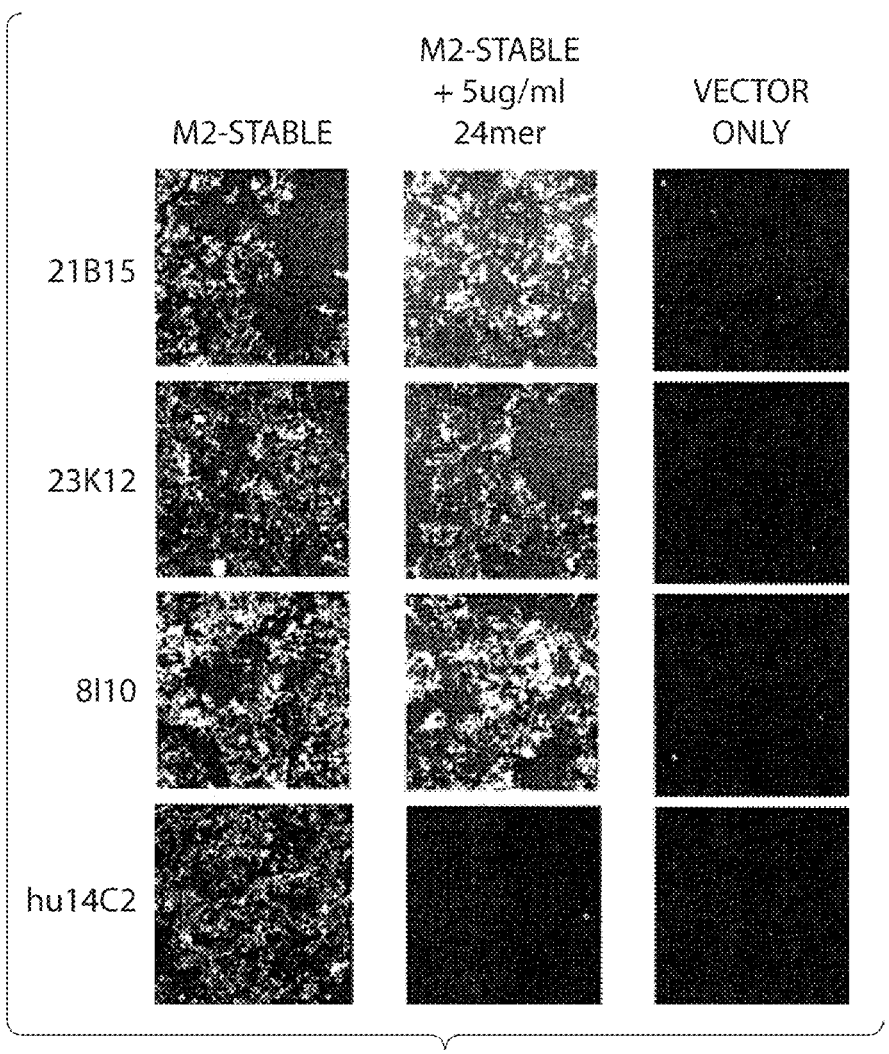
FIG. 1 shows the binding of three anti-M2 antibodies and control hu14C2 antibody to 293-HEK cells transfected with an M2 expression construct or control vector, in the presence or absence of free M2 peptide.

The present invention relates to an immunogenic composition comprising synthetic peptide immunogens capable of inducing antibodies against the extracellular domain of the matrix 2 (M2) polypeptide of influenza A virus. The present invention provides peptides that bind human monoclonal antibodies specific against the extracellular domain of the matrix 2 (M2) polypeptide of influenza A virus.

The predominant fraction of neutralizing antibodies is directed to the polymorphic regions of the hemagglutinin and neuraminidase proteins. A third transmembrane protein of type A influenza virus, matrix protein 2 (M2), is abundantly expressed by virus-infected cells, where it is believed to provide an obligatory transmembrane proton flux for viral replication (Ciampor et al., Virus Research 22:247 (1992); Grambas and Hay, Virology 190:11 (1992); Sugrue et al., EMBO J. 9:3469 (1990)). Unlike HA and NA, M2 is conserved and may represent a target for the development of antibody-based passive immunotherapies for influenza patients (Ito et al., J. Virology 65:5491 (1991); Slepushkin et al., Vaccine 13:1399 (1995); Neirynck et al., Nature Med. 5:1157 (1999)). Thus, such a neutralizing MAb would presumably target only one or a few strains. A recent focus has been on the relatively invariant matrix 2 (M2) protein. Potentially, a neutralizing MAb to M2 would be an adequate therapy for all influenza A strains.

The M2 protein is found in a homotetramer that forms an ion channel and is thought to aid in the uncoating of the virus upon entering the cell. After infection, M2 can be found in abundance at the cell surface. It is subsequently incorporated into the virion coat, where it only comprises about 2% of total coat protein. The M2 extracellular domain (M2e) is short, with the amino terminal 2-24 amino acids displayed outside of the cell.

Anti-M2 monoclonal antibodies to date have been directed towards this linear sequence. Thus, they may not exhibit desired binding properties to cellularly expressed M2, including conformational determinants on native M2.

Recent vaccine development has used immunogenic peptides conjugated to carrier proteins. However, carrier proteins are too complex for use in driving antibody responses to site-specific targets. The mass of the carrier molecule is much greater than that of the functionally important target peptide site. Consequently, the major immune response is directed to the carrier protein rather than to the target site of the peptide immunogen. Moreover, immunization with hapten-carrier conjugates frequently leads to carrier-induced immune suppression (Schutze et al., J Immunol, 1985, 135:2319). A disadvantage with the peptide-carrier protein conjugates is that these molecules are highly complex and are difficult to characterize and it is difficult to develop effective quality control procedures for the manufacturing process.

To be effective, a peptide immunogen must do more than merely evoke an anti-peptide response. An effective peptide immunogen must also evoke a functional immune response, i.e., the antibody produced must have immunological cross-reactivity to the authentic target. It is known that peptide immunogens generally do not retain a preferred structure. Therefore, it is important in designing a peptide target site to introduce structural constraints. However, the imposed structural constraint must be able to mimic the conformation of the targeted epitope so that antibodies evoked will be cross-reactivities to that site on the authentic molecule (Moore, Chapter 2 in Synthetic Peptides A User's guide, ed Grant, WH Freeman and Company: New York, 1992, pp 63-67). Peptide immunogens have been designed employing promiscuous Th epitopes, the invasin domain, and with imposed structural constraint for a peptide-based vaccine for HIV (U.S. Pat. No. 6,090,388).

A long-felt need exists in the art for new antibodies that bind to the cell-expressed M2 and conformational determinants on the native M2. Accordingly, a suitable peptide-based immunogen that mimic M2 is needed for generating vaccines and therapeutics against influenza virus. It would be desirable to provide a synthetic peptide immunogen that generates a site-specific immune response without epitopic suppression by undesirable T cell responses. The peptide-based anti-M2e immunogen should provoke an early and strong immune response in humans for protective immunity without the adverse carrier-induced immune suppression. The peptide immunogen should also be stable and well defined chemically with no need of elaborate downstream processing for ease of manufacture and quality control to avoid the need of an elaborate production plant.

M2 is a 96 amino acid transmembrane protein present as a homotetramer on the surface of influenza virus and virally infected cells. M2 contains a 23 amino acid ectodomain (M2e) that is highly conserved across influenza A strains. Few amino acid changes have occurred since the 1918 pandemic strain thus M2e is an attractive target for influenza therapies. Peptides that incorporate immunogenic epitopes of M2e form a preferred aspect of the present invention.

Mimotopes which have the same characteristics as these epitopes, and immunogens comprising such mimotopes which generate an immune response which cross-react with the IgE epitope in the context of the IgE molecule, also form part of the present invention.

The present invention, therefore, includes isolated peptides encompassing these IgE epitopes themselves, and any mimotope thereof. The meaning of mimotope is defined as an entity which is sufficiently similar to the native M2e epitope so as to be capable of being recognized by antibodies which recognize the native M2e epitope; (Gheysen, H. M., et al., 1986, Synthetic peptides as antigens. Wiley, Chichester, Ciba foundation symposium 119, p 130-149; Gheysen, H. M., 1986, Molecular Immunology, 23, 7, 709-715); or are capable of raising antibodies, when coupled to a suitable carrier, which antibodies cross-react with the native M2e epitope.

Monoclonal Antibodies for Screening M2e Peptide Immunogens

The antibodies used for screening the peptide immunogens are referred to herein as huM2e antibodies. Monoclonal antibodies used are specific to the M2 ectodomain (M2e) and derived from full-length M2 is expressed in cell lines. The huM2e antibodies bind conformational determinants on the M2-transfected cells, as well as native M2, either on influenza infected cells, or on the virus itself. The huM2e antibodies do not bind the linear M2e peptide, but they do bind several natural M2 variants expressed upon cDNA transfection into cell lines. The human monoclonal antibodies exhibit specificity for a very broad range of influenza A virus strains.

The huM2e antibodies have one or more of the following characteristics: the huM2e antibody binds a) to an epitope in the extracellular domain of the matrix 2 (M2) polypeptide of an influenza virus; b) binds to influenza A infected cells; and/or c) binds to influenza A virus (i.e., virons). The huM2e antibodies of the invention eliminate influenza infected cells through immune effector mechanisms such as ADCC and promotes direct viral clearance by binding to influenza virons. The huM2e antibodies of the invention bind to the amino-terminal region of the M2e polypeptide. Preferably, the huM2e antibodies of the invention bind to the amino-terminal region of the M2e polypeptide wherein the N-terminal methionine residue is absent. Exemplary M2e sequences include those sequences listed on Table 1 below.

TABLE 1

Exemplary M2e sequences

| Type | Name | Subtype | M2E Sequence | SEQ ID NO: |
|---|---|---|---|---|
| A | BREVIG MISSION.1.1918 | H1N1 | MSLLTEVETPTRNEWGCRCNDSSD | 48 |
| A | FORT MONMOUTH.1.1947 | H1N1 | MSLLTEVETPTKNEWECRCNDSSD | 49 |
| A | .SINGAPORE.02.2005 | H3N2 | MSLLTEVETPIRNEWECRCNDSSD | 50 |
| A | WISCONSIN.10.98 | H1N1 | MSLLTEVETPIRNGWECKCNDSSD | 51 |
| A | WISCONSIN.301.1976 | H1N1 | MSLLTEVETPIRSEWGCRCNDSSD | 52 |
| A | PANAMA.1.66 | H2N2 | MSFLPEVETPIRNEWGCRCNDSSD | 53 |
| A | NEW YORK.321.1999 | H3N2 | MSLLTEVETPIRNEWGCRCNDSSN | 54 |
| A | CARACAS.1.71 | H3N2 | MSLLTEVETPIRKEWGCRCNDSSD | 55 |
| A | TAIWAN.3.71 | H3N2 | MSFLTEVETPIRNEWGCRCNDSSD | 56 |
| A | WUHAN.359.95 | H3N2 | MSLPTEVETPIRSEWGCRCNDSSD | 57 |
| A | HONG KONG.1144.99 | H3N2 | MSLLPEVETPIRNEWGCRCNDSSD | 58 |
| A | HONG KONG.1180.99 | H3N2 | MSLLPEVETPIRNGWGCRCNDSSD | 59 |
| A | HONG KONG.1774.99 | H3N2 | MSLLTEVETPTRNGWECRCSGSSD | 60 |
| A | NEW YORK.217.02 | H1N2 | MSLLTEVETPIRNEWEYRCNDSSD | 61 |
| A | NEW YORK.300.2003 | H1N2 | MSLLTEVETPIRNEWEYRCSDSSD | 62 |
| A | SWINE.SPAIN.54008.2004 | H3N2 | MSLLTEVETPTRNGWECRYSDSSD | 63 |
| A | GUANGZHOU.333.99 | H9N2 | MSFLTEVETLTRNGWECRCSDSSD | 64 |
| A | HONG KONG.1073.99 | H9N2 | MSLLTEVETLTRNGWECKCRDSSD | 65 |
| A | HONG KONG.1.68 | H3N2 | MSLLTEVETPIRNEWGCRCNDSSD | 66 |
| A | SWINE.HONG KONG.126.1982 | H3N2 | MSLLTEVETPIRSEWGCRCNDSGD | 67 |
| A | NEW YORK.703.1995 | H3N2 | MSLLTEVETPIRNEWECRCNGSSD | 68 |
| A | SWINE.QUEBEC.192.81 | H1N1 | MSLPTEVETPIRNEWGCRCNDSSD | 69 |
| A | PUERTO RICO.8.34 | H1N1 | MSLLTEVETPIRNEWGCRCNGSSD | 70 |
| A | HONG KONG.485.97 | H5N1 | MSLLTEVDTLTRNGWGCRCSDSSD | 71 |
| A | HONG KONG.542.97 | H5N1 | MSLLTEVETLTKNGWGCRCSDSSD | 72 |
| A | SILKY CHICKEN.SHANTOU.1826.2004 | H9N2 | MSLLTEVETPTRNGWECKCSDSSD | 73 |
| A | CHICKEN.TAIWAN.0305.04 | H6N1 | MSLLTEVETHTRNGWECKCSDSSD | 74 |
| A | QUAIL.ARKANSAS.16309-7.94 | H7N3NSA | MSLLTEVKTPTRNGWECKCSDSSD | 75 |
| A | HONG KONG.486.97 | H5N1 | MSLLTEVETLTRNGWGCRCSDSSD | 76 |

TABLE 1-continued

Exemplary M2e sequences

| Type | Name | Subtype | M2E Sequence | SEQ ID NO: |
|---|---|---|---|---|
| A | CHICKEN.PENNSYLVANIA.13552-1.98 | H7N2NSB | MSLLTEVETPTRDGWECKCSDSSD | 77 |
| A | CHICKEN.HEILONGJIANG.48.01 | H9N2 | MSLLTEVETPTRNGWGCRCSDSSD | 78 |
| A | SWINE.KOREA.S5.2005 | H1N2 | MSLLTEVETPTRNGWECKCNDSSD | 79 |
| A | HONG KONG.1073.99 | H9N2 | MSLLTEVETLTRNGWECKCSDSSD | 80 |
| A | WISCONSIN.3523.88 | H1N1 | MSLLTEVETPIRNEWGCKCNDSSD | 81 |
| A | X-31 VACCINE STRAIN | H3N2 | MSFLTEVETPIRNEWGCRCNGSSD | 82 |
| A | CHICKEN.ROSTOCK.8.1934 | H7N1 | MSLLTEVETPTRNGWECRCNDSSD | 83 |
| A | ENVIRONMENT.NEW YORK.16326-1.2005 | H7N2 | MSLLTEVETPIRKGWECNCSDSSD | 84 |
| A | INDONESIA.560H.2006 | H5N1 | MSLLTEVETPTRNEWECRCSDSSD | 85 |
| A | CHICKEN.HONG KONG.SF1.03 | H9N2 | MSLLTGVETHTRNGWGCKCSDSSD | 86 |
| A | CHICKEN.HONGKONG.YU427.03 | H9N2 | MSLLPEVETHTRNGWGCRCSDSSD | 87 |

In one embodiment, the peptide immunogens of the invention comprise a M2e peptide that wholly or partially includes the amino acid residues from position 2 to position 7 of M2e (SLLTEV). The huM2e antibodies bind wholly or partially to the amino acid sequence SLLTE (SEQ ID NO: 47) comprising the peptide immunogens of the invention.

Exemplary huM2e monoclonal antibodies that bind to the peptide immunogens are the 8I10, 21B15 and 23K12 antibodies described herein.

The 8I10 antibody includes a heavy chain variable region (SEQ ID NO: 88) encoded by the nucleic acid sequence shown below in SEQ ID NO: 89, and a light chain variable region (SEQ ID NO: 90) encoded by the nucleic acid sequence shown in SEQ ID NO: 91.

The amino acids encompassing the CDRs as defined by Chothia, C. et al. (1989, Nature, 342: 877-883) are underlined and those defined by Kabat E. A. et al. (1991, Sequences of Proteins of Immunological Interest, 5$^{th}$ edit., NIH Publication no. 91-3242 U.S. Department of Heath and Human Services.) are highlighted in bold in the sequences below.

The heavy chain CDRs of the 8I10 antibody have the following sequences per Kabat definition: NYYWS (SEQ ID NO: 92), FIYYGGNTKYNPSLKS (SEQ ID NO: 93) and ASCSGGYCILD (SEQ ID NO: 94). The light chain CDRs of the 8I10 antibody have the following sequences per Kabat definition: RASQNIYKYLN (SEQ ID NO: 95), AA SGLQS (SEQ ID NO: 96) and QQSYSPPLT (SEQ ID NO: 97).

The heavy chain CDRs of the 8I10 antibody have the following sequences per Chothia definition: GSSISN (SEQ ID NO: 98), FIYYGGNTK (SEQ ID NO: 99) and ASCSG-GYCILD (SEQ ID NO: 94). The light chain CDRs of the 8I10 antibody have the following sequences per Chothia definition: RASQNIYKYLN (SEQ ID NO: 95), AASGLQS (SEQ ID NO: 96) and QQSYSPPLT (SEQ ID NO: 97).

```
>8I10 VH nucleotide sequence:
                                                         (SEQ ID NO: 89)
CAGGTGCAATTGCAGGAGTCGGGCCCAGGACTGGTGAAGCCTTCGGAGACCCTGTCCCTCACCTGCACTGTCT

CTGGTTCGTCCATCAGTAATTACTACTGGAGCTGGATCCGGCAGTCCCCAGGGAAGGGACTGGAGTGGATTGG

GTTTATCTATTACGGTGGAAACACCAAGTACAATCCCTCCCTCAAGAGCCGCGTCACCATATCACAAGACACT

TCCAAGAGTCAGGTCTCCCTGACGATGAGCTCTGTGACCGCTGCGGAATCGGCCGTCTATTTCTGTGCGAGAG

CGTCTTGTAGTGGTGGTTACTGTATCCTTGACTACTGGGGCCAGGGAACCCTGGTCACCGTCTCG

>8I10 VH amino acid sequence:
Kabat Bold, Chothia underlined
                                                         (SEQ ID NO: 88)
  Q V Q L Q E S G P G L V K P S E T L S L T C T V S

G S S I S N Y Y W S W I R Q S P G K G L E W I G F

I Y Y G G N T K Y N P S L K S R V T I S Q D T S K

S Q V S L T M S S V T A A E S A V Y F C A R A S C

S G G Y C I L D Y W G Q G T L V T V S

>8I10 VL nucleotide sequence:
```

-continued

```
                                                              (SEQ ID NO: 91)
GACATCCAGATGACCCAGTCTCCATCCTCCCTGTCTGCATCTGTAGGAGACAGAGTCACCATCACTTGCCGGG

CGAGTCAGAACATTTACAAGTATTTAAATTGGTATCAGCAGAGACCAGGGAAAGCCCCTAAGGGCCTGATCTC

TGCTGCATCCGGGTTGCAAAGTGGGGTCCCATCAAGGTTCAGTGGCAGTGGATCTGGGACAGATTTCACTCTC

ACCATCACCAGTCTGCAACCTGAAGATTTTGCAACTTACTACTGTCAACAGAGTTACAGTCCCCCTCTCACTT

TCGGCGGAGGGACCAGGGTGGAGATCAAAC
```

>8I10 VL amino acid sequence:
Kabat Bold, Chothia underlined
                                                              (SEQ ID NO: 90)
D I Q M T Q S P S S L S A S V G D R V T I T C <u>R A</u>

<u>S Q N I Y K Y L N</u> W Y Q Q R P G K A P K G L I S <u>A</u>

<u>A S G L Q S</u> G V P S R F S G S G S G T D F T L T I

T S L Q P E D F A T Y Y C <u>Q Q S Y S P P L T</u> F G G

G T R V E I K

The 21B15 antibody includes antibody includes a heavy chain variable region (SEQ ID NO: 100) encoded by the nucleic acid sequence shown below in SEQ ID NO: 101, and a light chain variable region (SEQ ID NO: 102) encoded by the nucleic acid sequence shown in SEQ ID NO: 103.

The amino acids encompassing the CDRs as defined by Chothia et al. 1989, are underlined and those defined by Kabat et al., 1991 are highlighted in bold in the sequences below.

The heavy chain CDRs of the 21B15 antibody have the following sequences per Kabat definition: NYYWS (SEQ ID NO: 92), FIYYGGNTKYNPSLKS (SEQ ID NO: 93) and ASCSGGYCILD (SEQ ID NO: 94). The light chain CDRs of the 21B15 antibody have the following sequences per Kabat definition: RASQNIYKYLN (SEQ ID NO: 95), AASGLQS (SEQ ID NO: 96) and QQSYSPPLT (SEQ ID NO: 97).

The heavy chain CDRs of the 21B15 antibody have the following sequences per Chothia definition: GSSISN (SEQ ID NO: 98), FIYYGGNTK (SEQ ID NO: 93) and ASCSGGYCILD (SEQ ID NO: 94). The light chain CDRs of the 21B15 antibody have the following sequences per Chothia definition: RASQNIYKYLN (SEQ ID NO: 95), AASGLQS (SEQ ID NO: 96) and QQSYSPPLT (SEQ ID NO: 97).

>21B15 VH nucleotide sequence:
```
                                                              (SEQ ID NO: 101)
CAGGTGCAATTGCAGGAGTCGGGCCCAGGACTGGTGAAGCCTTCGGAGACCCTGTCCCTCACCTGCACTGTCT

CTGGTTCGTCCATCAGTAATTACTACTGGAGCTGGATCCGGCAGTCCCCAGGGAAGGGACTGGAGTGGATTGG

GTTTATCTATTACGGTGGAAACACCAAGTACAATCCCTCCCTCAAGAGCCGCGTCACCATATCACAAGACACT

TCCAAGAGTCAGGTCTCCCTGACGATGAGCTCTGTGACCGCTGCGGAATCGGCCGTCTATTTCTGTGCGAGAG

CGTCTTGTAGTGGTGGTTACTGTATCCTTGACTACTGGGGCCAGGGAACCCTGGTCACCGTCTCG
```

>21B15 VH amino acid sequence:
Kabat Bold, Chothia underlined
                                                              (SEQ ID NO: 100)
Q V Q L Q E S G P G L V K P S E T L S L T C T V S <u>G S S I S</u> N Y Y W S W I R Q S P G K G L E W I G F

I Y Y G G N T K Y N P S L K S R V T I S Q D T S K

S Q V S L T M S S V T A A E S A V Y F C A R <u>A S C</u>

<u>S G G Y C I L D</u> Y W G Q G T L V T V S

>21B15 VL nucleotide sequence:
```
                                                              (SEQ ID NO: 103)
GACATCCAGGTGACCCAGTCTCCATCCTCCCTGTCTGCATCTGTAGGAGACAGAGTCACCATCACTTGCCGCG

CGAGTCAGAACATTTACAAGTATTTAAATTGGTATCAGCAGAGACCAGGGAAAGCCCCTAAGGGCCTGATCTC

TGCTGCATCCGGGTTGCAAAGTGGGGTCCCATCAAGGTTCAGTGGCAGTGGATCTGGGACAGATTTCACTCTC

ACCATCACCAGTCTGCAACCTGAAGATTTTGCAACTTACTACTGTCAACAGAGTTACAGTCCCCCTCTCACTT

TCGGCGGAGGGACCAGGGTGGATATCAAAC
```

>21B15 VL amino acid sequence:
Kabat Bold, Chothia underlined
                                                              (SEQ ID NO: 102)

-continued

D I Q V T Q S P S S L S A S V G D R V T I T C R A

S Q N I Y K Y L N W Y Q Q R P G K A P K G L I S A

A S G L Q S G V P S R F S G S G S G T D F T L T I

T S L Q P E D F A T Y Y C Q Q S Y S P P L T F G G

G T R V D I K

The 23K12 antibody includes antibody includes a heavy chain variable region (SEQ ID NO: 104) encoded by the nucleic acid sequence shown below in SEQ ID NO: 105, and a light chain variable region (SEQ ID NO: 106) encoded by the nucleic acid sequence shown in SEQ ID NO: 107.

The amino acids encompassing the CDRs as defined by Chothia et al., 1989 are underlined and those defined by Kabat et al., 1991 are highlighted in bold in the sequences below.

The heavy chain CDRs of the 23K12 antibody have the following sequences per Kabat definition: SNYMS (SEQ ID NO: 108), VIYSGGSTYYADSVK (SEQ ID NO: 109) and CLSRMRGYGLDV (SEQ ID NO: 110). The light chain CDRs of the 23K12 antibody have the following sequences per Kabat definition: RTSQSISSYLN (SEQ ID NO: 111), AASSLQSGVPSRF (SEQ ID NO: 112) and QQSYSMPA (SEQ ID NO: 113).

The heavy chain CDRs of the 23K12 antibody have the following sequences per Chothia definition: GFTVSSN (SEQ ID NO: 114), VIYSGGSTY (SEQ ID NO: 115) and CLSRMRGYGLDV (SEQ ID NO: 110). The light chain CDRs of the 23K12 antibody have the following sequences per Chothia definition: RTSQSISSYLN (SEQ ID NO: 111), AASSLQSGVPSRF (SEQ ID NO: 112) and QQSYSMPA (SEQ ID NO: 113).

```
>23K12 VH nucleotide sequence:
                                                        (SEQ ID NO: 105)
GAGGTGCAGCTGGTGGAGTCTGGGGGAGGCTTGGTCCAGCCTGGGGGGTCCCTGAGAATCTCCTGTGCAGCCT

CTGGATTCACCGTCAGTAGCAACTACATGAGTTGGGTCCGCCAGGCTCCAGGGAAGGGGCTGGAGTGGGTCTC

AGTTATTTATAGTGGTGGTAGCACATACTACGCAGACTCCGTGAAGGGCAGATTCTCCTTCTCCAGAGACAAC

TCCAAGAACACAGTGTTTCTTCAAATGAACAGCCTGAGAGCCGAGGACACGGCTGTGTATTACTGTGCGAGAT

GTCTGAGCAGGATGCGGGGTTACGGTTTAGACGTCTGGGGCCAAGGGACCACGGTCACCGTCTCG

>23K12 VH amino acid sequence:
Kabat Bold, Chothia underlined
                                                        (SEQ ID NO: 104)
E V Q L V E S G G G L V Q P G G S L R I S C A A S

G F T V S S N Y M S W V R Q A P G K G L E W V S V

I Y S G G S T Y Y A D S V K G R F S F S R D N S K

N T V F L Q M N S L R A E D T A V Y Y C A R C L S

R M R G Y G L D V W G Q G T T V T V S

>23K12 VL nucleotide sequence:
                                                        (SEQ ID NO: 107)
GACATCCAGATGACCCAGTCTCCATCCTCCCTGTCTGCATCTGTAGGAGACAGAGTCACCATCACTTGCCGGA

CAAGTCAGAGCATTAGCAGCTATTTAAATTGGTATCAGCAGAAACCAGGGAAAGCCCCTAAACTCCTGATCTA

TGCTGCATCCAGTTTGCAAAGTGGGGTCCCATCAAGGTTCAGTGGCAGTGGATCTGGGACAGATTTCACTCTC

ACCATCAGCGGTCTGCAACCTGAAGATTTTGCAACCTACTACTGTCAACAGAGTTACAGTATGCCTGCCTTTG

GCCAGGGGACCAAGCTGGAGATCAAA

>23K12 VL amino acid sequence:
Kabat Bold, Chothia underlined
                                                        (SEQ ID NO: 106)
D I Q M T Q S P S S L S A S V G D R V T I T C R T

S Q S I S S Y L N W Y Q Q K P G K A P K L L I Y A

A S S L Q S G V P S R F S G S G S G T D F T L T I

S G L Q P E D F A T Y Y C Q Q S Y S M P A F G Q G

T K L E I K
```

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Sambrook, et al. Molecular Cloning: A Laboratory Manual (2nd Edition, 1989); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984).

The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

Definitions

The following definitions are useful in understanding the present invention:

The term "antibody" (Ab) as used herein includes monoclonal antibodies, polyclonal antibodies, multispecific antibodies (e.g., bispecific antibodies), and antibody fragments, so long as they exhibit the desired biological activity. The term "immunoglobulin" (Ig) is used interchangeably with "antibody" herein.

An "isolated antibody" is one that has been separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody is purified: (1) to greater than 95% by weight of antibody as determined by the Lowry method, and most preferably more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic four-chain antibody unit is a heterotetrameric glycoprotein composed of two identical light (L) chains and two identical heavy (H) chains. An IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H 1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71, and Chapter 6.

The L chain from any vertebrate species can be assigned to one of two clearly distinct types, called kappa (κ) and lambda (λ), based on the amino acid sequences of their constant domains ($C_L$). Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated alpha (α), delta (δ), epsilon (ε), gamma (γ) and mu (μ), respectively. The γ and α classes are further divided into subclasses on the basis of relatively minor differences in $C_H$ sequence and function, e.g., humans express the following subclasses: IgG1, IgG2, IgG3, IgG4, IgA 1, and IgA2.

The term "variable" refers to the fact that certain segments of the V domains differ extensively in sequence among antibodies. The V domain mediates antigen binding and defines specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody that are responsible for antigen binding. The hypervariable region generally comprises amino acid residues from a "complementarity determining region" or "CDR" (e.g., around about residues 24-34

(L1), 50-56 (L2) and 89-97 (L3) in the $V_L$, and around about 1-35 (H1), 50-65 (H2) and 95-102 (H3) in the $V_H$; Kabat et al., Sequences of Proteins of Immunological Interest, 5th Ed. Public Health Service, National Institutes of Health, Bethesda, Md. (1991)) and/or those residues from a "hypervariable loop" (e.g., residues 26-32 (L1), 50-52 (L2) and 91-96 (L3) in the $V_L$, and 26-32 (H1), 53-55 (H2) and 96-101 (H3) in the $V_H$; Chothia and Lesk, J. Mol. Biol. 196:901-917 (1987)).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816, 567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)). The present invention provides variable domainantigen-binding sequences derived from human antibodies. Accordingly, chimeric antibodies of primary interest herein include antibodies having one or more human antigen binding sequences (e.g., CDRs) and containing one or more sequences derived from a non-human antibody, e.g., an FR or C region sequence. In addition, chimeric antibodies of primary interest herein include those comprising a human variable domain antigen binding sequence of one antibody class or subclass and another sequence, e.g., FR or C region sequence, derived from another antibody class or subclass. Chimeric antibodies of interest herein also include those containing variable domain antigen-binding sequences related to those described herein or derived from a different species, such as a non-human primate (e.g., Old World Monkey, Ape, etc). Chimeric antibodies also include primatized and humanized antibodies.

Furthermore, chimeric antibodies may comprise residues that are not found in the recipient antibody or in the donor antibody. These modifications are made to further refine antibody performance. For further details, see Jones et al., Nature 321:522-525 (1986); Riechmann et al., Nature 332:323-329 (1988); and Presta, Curr. Op. Struct. Biol. 2:593-596 (1992).

A "humanized antibody" is generally considered to be a human antibody that has one or more amino acid residues introduced into it from a source that is non-human. These non-human amino acid residues are often referred to as "import" residues, which are typically taken from an "import" variable domain. Humanization is traditionally performed following the method of Winter and co-workers (Jones et al., Nature, 321:522-525 (1986); Reichmann et al., Nature, 332:323-327 (1988); Verhoeyen et al., Science, 239: 1534-1536 (1988)), by substituting import hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species.

A "human antibody" is an antibody containing only sequences present in an antibody naturally produced by a human. However, as used herein, human antibodies may comprise residues or modifications not found in a naturally occurring human antibody, including those modifications and variant sequences described herein. These are typically made to further refine or enhance antibody performance.

An "intact" antibody is one that comprises an antigen-binding site as well as a $C_L$ and at least heavy chain constant domains, $C_H1$, $C_H2$ and $C_H3$. The constant domains may be native sequence constant domains (e.g., human native sequence constant domains) or amino acid sequence variant thereof. Preferably, the intact antibody has one or more effector functions.

An "antibody fragment" comprises a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870; Zapata et al., Protein Eng. 8(10): 1057-1062 [1995]); single-chain antibody molecules; and multispecific antibodies formed from antibody fragments.

The phrase "functional fragment or analog" of an antibody is a compound having qualitative biological activity in common with a full-length antibody. For example, a functional fragment or analog of an anti-IgE antibody is one that can bind to an IgE immunoglobulin in such a manner so as to prevent or substantially reduce the ability of such molecule from having the ability to bind to the high affinity receptor, Fc$_\epsilon$RI.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment that roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments that have hinge cysteines between them. Other chemical couplings of antibody fragments are also known.

The "Fc" fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment that contains a complete antigen-recognition and -binding site. This fragment consists of a dimer of one heavy- and one light-chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$, domains that enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

As used herein, an antibody that "internalizes" is one that is taken up by (i.e., enters) the cell upon binding to an antigen on a mammalian cell (e.g., a cell surface polypeptide or receptor). The internalizing antibody will of course include antibody fragments, human or chimeric antibody, and antibody conjugates. For certain therapeutic applications, internalization in vivo is contemplated. The number of antibody molecules internalized will be sufficient or adequate to kill a cell or inhibit its growth, especially an infected cell. Depending on the potency of the antibody or antibody conjugate, in some instances, the uptake of a single antibody molecule into the cell is sufficient to kill the target cell to which the antibody binds. For example, certain toxins are highly potent in killing such that internalization of one molecule of the toxin conjugated to the antibody is sufficient to kill the infected cell.

As used herein, an antibody is said to be "immunospecific," "specific for" or to "specifically bind" an antigen if it reacts at a detectable level with the antigen, preferably with an affinity constant, $K_a$, of greater than or equal to about $10^4$ M$^{-1}$, or greater than or equal to about $10^5$ M$^{-1}$, greater than or equal to about $10^6$ M$^{-1}$, greater than or equal to about $10^7$ M$^{-1}$, or greater than or equal to $10^8$ Affinity of an antibody for its cognate antigen is also commonly expressed as a dissociation constant $K_D$, and in certain embodiments, HuM2e antibody specifically binds to M2e if it binds with a $K_D$ of less than or equal to $10^{-4}$ M, less than or equal to about $10^{-5}$ M, less than or equal to about $10^{-6}$ M, less than or equal to $10^{-7}$ M, or less than or equal to $10^{-8}$ M. Affinities of antibodies can be readily determined using conventional techniques, for example, those described by Scatchard et al. (*Ann. N.Y. Acad. Sci. USA* 51:660 (1949)).

Binding properties of an antibody to antigens, cells or tissues thereof may generally be determined and assessed using immunodetection methods including, for example, immunofluorescence-based assays, such as immuno-histochemistry (IHC) and/or fluorescence-activated cell sorting (FACS).

An antibody having a "biological characteristic" of a designated antibody is one that possesses one or more of the biological characteristics of that antibody which distinguish it from other antibodies. For example, in certain embodiments, an antibody with a biological characteristic of a designated antibody will bind the same epitope as that bound by the designated antibody and/or have a common effector function as the designated antibody.

The term "antagonist" antibody is used in the broadest sense, and includes an antibody that partially or fully blocks, inhibits, or neutralizes a biological activity of an epitope, polypeptide, or cell that it specifically binds. Methods for identifying antagonist antibodies may comprise contacting a polypeptide or cell specifically bound by a candidate antagonist antibody with the candidate antagonist antibody and measuring a detectable change in one or more biological activities normally associated with the polypeptide or cell.

An "antibody that inhibits the growth of infected cells" or a "growth inhibitory" antibody is one that binds to and results in measurable growth inhibition of infected cells expressing or capable of expressing an M2e epitope bound by an antibody. Preferred growth inhibitory antibodies inhibit growth of infected cells by greater than 20%, preferably from about 20% to about 50%, and even more preferably, by greater than 50% (e.g., from about 50% to about 100%) as compared to the appropriate control, the control typically being infected cells not treated with the antibody being tested. Growth inhibition can be measured at an antibody concentration of about 0.1 to 30 µg/ml or about 0.5 nM to 200 nM in cell culture, where the growth inhibition is determined 1-10 days after exposure of the infected cells to the antibody. Growth inhibition of infected cells in vivo can be determined in various ways known in the art. The antibody is growth inhibitory in vivo if administration of the antibody at about 1 µg/kg to about 100 mg/kg body weight results in reduction the percent of infected cells or total number of infected cells within about 5 days to 3 months from the first administration of the antibody, preferably within about 5 to 30 days.

An antibody that "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). Preferably the cell is an infected cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody that induces apoptosis is one that results in about 2 to 50 fold, preferably about 5 to 50 fold, and most preferably about 10 to 50 fold, induction of annexin binding relative to untreated cell in an annexin binding assay.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound to Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. Nos. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al., PNAS (USA) 95:652-656 (1998).

"Fc receptor" or "FcR" describes a receptor that binds to the Fc region of an antibody. In certain embodiments, the FcR is a native sequence human FcR. Moreover, a preferred FcR is one that binds an IgG antibody (a gamma receptor) and includes receptors of the FcγRI, FcγRII, and FcγRIII subclasses, including allelic variants and alternatively spliced forms of these receptors. FCγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daeron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., J. Immunol. 24:249 (1994)).

"Human effector cells" are leukocytes that express one or more FcRs and perform effector functions. Preferably, the cells express at least FcγRIII and perform ADCC effector function. Examples of human leukocytes that mediate ADCC include PBMC, NK cells, monocytes, cytotoxic T cells and neutrophils; with PBMCs and NK cells being preferred. The effector cells may be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) that are bound to their cognate antigen. To assess complement activation, a CDC assay, e.g., as described in Gazzano-Santoro et al., J. Immunol. Methods 202:163 (1996), may be performed.

The terms "influenza A" and "Influenzavirus A" refer to a genus of the Orthomyxoviridae family of viruses. Influenzavirus A includes only one species: influenza A virus which cause influenza in birds, humans, pigs, and horses. Strains of all subtypes of influenza A virus have been isolated from wild birds, although disease is uncommon. Some isolates of influenza A virus cause severe disease both in domestic poultry and, rarely, in humans.

A "mammal" for purposes of treating n infection, refers to any mammal, including humans, domestic and farm animals, and zoo, sports, or pet animals, such as dogs, cats, cattle, horses, sheep, pigs, goats, rabbits, etc. Preferably, the mammal is human.

"Treating" or "treatment" or "alleviation" refers to both therapeutic treatment and prophylactic or preventative measures; wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for an infection if, after receiving a therapeutic amount of an antibody according to the methods of the present invention, the patient shows observable and/or measurable reduction in or absence of one or more of the following: reduction in the number of infected cells or absence of the infected cells; reduction in the percent of total cells that are infected; and/or relief to some extent, one or more of the symptoms associated with the specific infection; reduced morbidity and mortality, and improvement in quality of life issues. The above parameters for assessing successful treatment and improvement in the disease are readily measurable by routine procedures familiar to a physician.

The term "therapeutically effective amount" refers to an amount of an antibody or a drug effective to "treat" a disease or disorder in a subject or mammal. See preceding definition of "treating."

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

Administration "in combination with" one or more further therapeutic agents includes simultaneous (concurrent) and consecutive administration in any order.

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ polyethylene glycol (PEG), and PLURONICS™.

"Label" as used herein refers to a detectable compound or composition that is conjugated directly or indirectly to the antibody so as to generate a "labeled" antibody. The label may be detectable by itself (e.g., radioisotope labels or fluorescent labels) or, in the case of an enzymatic label, may catalyze chemical alteration of a substrate compound or composition that is detectable.

The term "epitope tagged" as used herein refers to a chimeric polypeptide comprising a polypeptide fused to a "tag polypeptide." The tag polypeptide has enough residues to provide an epitope against which an antibody can be made, yet is short enough such that it does not interfere with activity of the polypeptide to which it is fused. The tag polypeptide is also preferably fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

A "small molecule" is defined herein to have a molecular weight below about 500 Daltons.

The terms "nucleic acid" and "polynucleotide" are used interchangeably herein to refer to single- or double-stranded RNA, DNA, or mixed polymers. Polynucleotides may include genomic sequences, extra-genomic and plasmid sequences, and smaller engineered gene segments that express, or may be adapted to express polypeptides.

An "isolated nucleic acid" is a nucleic acid that is substantially separated from other genome DNA sequences as well as proteins or complexes such as ribosomes and polymerases, which naturally accompany a native sequence. The term embraces a nucleic acid sequence that has been removed from its naturally occurring environment, and includes recombinant or cloned DNA isolates and chemically synthesized analogues or analogues biologically synthesized by heterologous systems. A substantially pure nucleic acid includes isolated forms of the nucleic acid. Of course, this refers to the nucleic acid as originally isolated and does not exclude genes or sequences later added to the isolated nucleic acid by the hand of man.

The term "polypeptide" is used in its conventional meaning, i.e., as a sequence of amino acids. The polypeptides are not limited to a specific length of the product. Peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof. Particular polypeptides of interest in the context of this invention are amino acid subsequences comprising CDRs and being capable of binding an antigen or Influenza A-infected cell.

An "isolated polypeptide" is one that has been identified and separated and/or recovered from a component of its natural environment. In preferred embodiments, the isolated polypeptide will be purified (1) to greater than 95% by weight of polypeptide as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated polypeptide includes the polypeptide in situ within recombinant cells since at least one component of the polypeptide's natural environment will not be present. Ordinarily, however, isolated polypeptide will be prepared by at least one purification step.

A "native sequence" polynucleotide is one that has the same nucleotide sequence as a polynucleotide derived from nature. A "native sequence" polypeptide is one that has the same amino acid sequence as a polypeptide (e.g., antibody) derived from nature (e.g., from any species). Such native sequence polynucleotides and polypeptides can be isolated from nature or can be produced by recombinant or synthetic means.

A polynucleotide "variant," as the term is used herein, is a polynucleotide that typically differs from a polynucleotide specifically disclosed herein in one or more substitutions, deletions, additions and/or insertions. Such variants may be naturally occurring or may be synthetically generated, for example, by modifying one or more of the polynucleotide sequences of the invention and evaluating one or more biological activities of the encoded polypeptide as described herein and/or using any of a number of techniques well known in the art.

A polypeptide "variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences of the invention and evaluating one or more biological activities of the polypeptide as described herein and/or using any of a number of techniques well known in the art.

Modifications may be made in the structure of the polynucleotides and polypeptides of the present invention and still obtain a functional molecule that encodes a variant or derivative polypeptide with desirable characteristics. When it is desired to alter the amino acid sequence of a polypeptide to create an equivalent, or even an improved, variant or portion of a polypeptide of the invention, one skilled in the art will typically change one or more of the codons of the encoding DNA sequence.

For example, certain amino acids may be substituted for other amino acids in a protein structure without appreciable loss of its ability to bind other polypeptides (e.g., antigens) or cells. Since it is the binding capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences that encode said peptides without appreciable loss of their biological utility or activity.

In many instances, a polypeptide variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity. U.S. Pat. No. 4,554,101 states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

Polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

When comparing polynucleotide and polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 *Methods in Enzymology* vol. 183, Academic Press, Inc., San Diego, Calif.; Higgins, D. G. and Sharp, P. M. (1989) CABIOS 5:151-153; Myers, E. W. and Muller W. (1988) *CABIOS* 4:11-17; Robinson, E. D. (1971) *Comb. Theor* 11:105; Santou, N. Nes, M. (1987) *Mol. Biol. Evol.* 4:406-425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad., Sci. USA* 80:726-730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389-3402 and Altschul et al. (1990) *J. Mol. Biol.* 215:403-410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information.

In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) Proc. Natl. Acad. Sci. USA 89:10915) alignments, (B) of 50, expectation (E) of 10, M=5, N=−4 and a comparison of both strands.

For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one approach, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residues occur in both sequences to yield the number of matched positions, dividing the number of matched positions by the total number of positions in the reference sequence (i.e., the window size) and multiplying the results by 100 to yield the percentage of sequence identity.

"Homology" refers to the percentage of residues in the polynucleotide or polypeptide sequence variant that are identical to the non-variant sequence after aligning the sequences and introducing gaps, if necessary, to achieve the maximum percent homology. In particular embodiments, polynucleotide and polypeptide variants have at least 70%, at least 75%, at least 80%, at least 90%, at least 95%, at least 98%, or at least 99% polynucleotide or polypeptide homology with a polynucleotide or polypeptide described herein.

"Vector" includes shuttle and expression vectors. Typically, the plasmid construct will also include an origin of replication (e.g., the ColE1 origin of replication) and a selectable marker (e.g., ampicillin or tetracycline resistance), for replication and selection, respectively, of the plasmids in bacteria. An "expression vector" refers to a vector that contains the necessary control sequences or regulatory elements for expression of the antibodies including antibody fragment of the invention, in bacterial or eukaryotic cells. Suitable vectors are disclosed below.

As used in this specification and the appended claims, the singular forms "a," "an" and "the" include plural references unless the content clearly dictates otherwise.

Preferred methods for determining mAb specificity and affinity by competitive inhibition can be found in Harlow, et al., Antibodies: A Laboratory Manual, Cold Spring Harbor Laboratory Press, Cold Spring Harbor, N.Y., 1988), Colligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference.

The techniques to raise antibodies of the present invention to small peptide sequences that recognize and bind to those sequences in the free or conjugated form or when presented as a native sequence in the context of a large protein are well known in the art. Such antibodies include murine, murine-human and human-human antibodies produced by hybridoma or recombinant techniques known in the art.

Screening Peptide Immunogens for Specific Binding to 8i10, or 23K12.

The present invention relates to peptide immunogens that bind HuM2e antibodies. In one embodiment, the antibody is an antibody designated herein as 8i10, 21B15, or 23K12. These antibodies are known to display preferential or specific binding to influenza A infected cells as compared to uninfected control cells of the same cell type.

In particular embodiments, the HuM2e antibodies bind to epitopes within M2e that are only present in the native conformation, i.e., as expressed in cells. In particular embodiments, these antibodies fail to specifically bind to an isolated M2e polypeptide, e.g., the 23 amino acid residue M2e fragment. It is understood that these antibodies recognize non-linear (i.e. conformational) epitope(s) of the M2 peptide. M2 ectodomain (M2e) includes or consists of the amino acid sequence SLLTEVETPIRNEWGCRCNDSSD (SEQ ID NO: 326) and variants thereof (The Center for Disease Control (CDC) influenza A database at www.flu.lanl.gov/).

The specific conformational epitopes within the M2 protein, and particularly within M2e, were identified as peptide immunogens which can be used as vaccines to prevent the development of influenza infection within a subject.

The peptide immunogen sequences were identified by discontinuous epitope mapping using CLIPS™ (Chemically Linked Immunogenic Peptides on Scaffolds; PepScan) technology, which has been developed to improve the biological function of synthetic peptides. CLIPS uses small, chemical "scaffolds" onto which one or more peptides can be attached. In vaccine development, these are ideal for mapping conformational (or 'discontinuous') epitopes because they closely resemble the native structure of proteins.

Binding activity of anti-M2 antibodies to mutant M2 peptides was analyzed with an ELISA assay using different M2 peptides. Human anti-M2 antibody nos. Z3G1, 8I10 and 23K12 were used in the study. Peptides comprising M2e sequences were screened for the ability to specifically bind HuM2e antibodies 8I10 and 23K12 and distinguished from the ability to bind the anti-M2 human monoclonal antibody Z3G1 (ATCC Deposit No. PTA-5967) which has a broad M2 binding spectrum. 8I10 and 23K12 have been characterized for the ability to bind M2 and M2e under conditions resembling native conformation. The assays were performed at both 0.01 μg/mL and 0.001 μg/mL concentrations of peptides. At 0.01 μg/mL, signal levels of 1000 or greater were selected and at 0.001 μg/mL, signal levels of 300 or greater were selected as significant. Most peptides that bind strongly to 8I10 and 23K12 also bind Z3G1.

TABLE 2

Peptides that specifically bind for 23K21 and 8I10 (A numeral "1" in the peptide sequence indicates a differentially protected cystein allowing for selective CLIP attachment at certain residues)

| SEQ ID NO: | Peptides that bind to 23K21 and 8I10 | Signal |
|---|---|---|
| 116 | CLTEVETPIRNEWGSRCSLLTEVETPIRNEWGC | 1922 |
| 117 | CLLTEVETPIRNEWGSCSLLTEVETPIRC | 1865 |

TABLE 2-continued Peptides that specifically bind for 23K21 and 8I10 (A numeral "1" in the peptide sequence indicates a differentially protected cystein allowing for selective CLIP attachment at certain residues)

| SEQ ID NO: | Peptides that bind to 23K21 and 8I10 | Signal |
|---|---|---|
| 118 | CSLLTEVETPIRNECSLLTEVETC | 1829 |
| 119 | CLTEVETPIRNEWGSRCSLLTEVETPIRNC | 1825 |
| 120 | CSLLTEVETPIRNCSLLTEVETPIRC | 1781 |
| 121 | CSLLTEVETPIRCSLLTEVETPIRC | 1767 |
| 122 | CSLLTEVETPIRNEWCSLLTEVETC | 1752 |
| 123 | CSLLTEVETPIRNECLTEVETPIRNEWGSRC | 1702 |
| 124 | CSLLTEVETPCSLLTEVETPIRC | 1693 |
| 125 | CTEVETPIRNEWGSRSCSLLTEVETPIRNEWGC | 1659 |
| 126 | CETPIRNEWGSRSNDSCSLLTEVETPIRNC | 1650 |
| 127 | CSLLTEVETCSLLTEVETC | 1647 |
| 128 | CSLLTEVETCSLLTEVETPIC | 1638 |
| 129 | CSLLTEVETPIRNCSLLTEVETPIRNC | 1602 |
| 130 | CSLLTEVETPIRNECSLLTEVETPIRC | 1588 |
| 131 | CSLLTEVETPIRCSLLTEVETPIRNC | 1549 |
| 132 | CVETPIRNEWGSRSNDCSLLTEVETPIC | 1548 |
| 133 | CSLLTEVETPIRNECSLLTEVETPIRNC | 1534 |
| 134 | CSLLTEVETCSLLTEVETPIRNC | 1480 |
| 135 | CSLLTEVETPIRNCSLLTEVETPIRNEWC | 1476 |
| 136 | CLTEVETPIRNEWGSRCSLLTEVETC | 1470 |
| 137 | CSLLTEVETPCSLLTEVETPIC | 1458 |
| 138 | CSLLTEVETPIRNEWGCLLTEVETPIRNEWGSC | 1456 |
| 139 | CSLLTEVETPIRNCSLLTEVETPIC | 1449 |
| 140 | CSLLTEVETPIRNEWGCSLLTEVETPIRNEWGC | 1434 |
| 141 | CSLLTEVETPIRNEWCSLLTEVETPIRNEWGC | 1427 |
| 142 | CSLLTEVETCSLLTEVETPC | 1424 |
| 143 | CSLLTEVETPIRNEWGCSLLTEVETPIRNC | 1418 |
| 144 | CSLLTEVETPIRNCSLLTEVETPC | 1405 |
| 145 | CSLLTEVETPIRNECSLLTEVETPIC | 1395 |
| 146 | CSLLTEVETPIRNECSLLTEVETPIRNEWC | 1394 |
| 147 | CSLLTEVETPIRCSLLTEVETC | 1388 |
| 148 | CSLLTEVETPIRNCSLLTEVETPIRNEWGC | 1356 |
| 149 | CTEVETPIRNEWGSRSCLTEVETPIRNEWGSRC | 1348 |
| 150 | CSLLTEVETCSLLTEVETPIRNEWC | 1345 |
| 151 | CSLLTEVETPIRCSLLTEVETPIC | 1340 |
| 152 | CSLLTEVETPIRNECSLLTEVETPIRNEWGC | 1331 |
| 153 | CSLLTEVETPCSLLTEVETPIRNC | 1320 |
| 154 | CETPIRNEWGSRSNDSCSLLTEVETPIRNEC | 1313 |
| 155 | CSLLTEVETPIRNEWCSLLTEVETPIRC | 1293 |
| 156 | CSLLTEVETPCSLLTEVETPC | 1286 |
| 157 | CSLLTEVETPIRNEWGCSLLTEVETPIRC | 1278 |
| 158 | CSLLTEVETPCSLLTEVETPIRNEWC | 1269 |
| 159 | CSLLTEVETPIRNEWGCVETPIRNEWGSRSNDC | 1241 |
| 160 | CSLLTEVETPIRCLLTEVETPIRNEWGSC | 1211 |
| 161 | CPIRNEWGSRSNDSSDCSLLTEVETC | 1206 |
| 162 | CLTEVETPIRNEWGSRCSLLTEVETPIRC | 1203 |
| 163 | CSLLTEVETCSLLTEVETPIRC | 1200 |
| 164 | CSLLTEVETPIRNECSLLTEVETPC | 1194 |
| 165 | CSLLTEVETPIRCSLLTEVETPIRNEC | 1194 |
| 166 | CSLLTEVETPIRNCSLLTEVETC | 1192 |
| 167 | CSLLTEVETPIRCSLLTEVETPIRNEWGC | 1188 |
| 168 | CVETPIRNEWGSRSNDCSLLTEVETPIRC | 1186 |
| 169 | CTPIRNEWGSRSNDSSCSLLTEVETPIRC | 1180 |
| 170 | CSLLTEVETPIRCLTEVETPIRNEWGSRC | 1175 |
| 171 | CSLLTEVETCSLLTEVETPIRNEC | 1172 |
| 172 | CEVETPIRNEWGSRSNCSLLTEVETPIRC | 1168 |
| 173 | CSLLTEVETPIRCSLLTEVETPIRNEWC | 1167 |
| 174 | CSLLTEVETPIRNEWCSLLTEVETPIRNEWC | 1165 |
| 175 | CSLLTEVETPIRNEWGCLTEVETPIRNEWGSRC | 1148 |
| 176 | CPIRNEWGSRSNDSSDCSLLTEVETPIRC | 1146 |
| 177 | CSLLTEVETPIRNEWCSLLTEVETPIC | 1144 |
| 178 | CLLTEVETPIRNEWGSCSLLTEVETPIRNC | 1141 |
| 179 | CSLLTEVETCLLTEVETPIRNEWGSC | 1141 |
| 180 | CSLLTEVETPIRNEWCSLLTEVETPIRNC | 1138 |
| 181 | CSLLTEVETPIRCSLLTEVETPC | 1115 |
| 182 | CSLLTEVETPCLLTEVETPIRNEWGSC | 1111 |
| 183 | CSLLTEVETPIRNCSLLTEVETPIRNEC | 1110 |
| 184 | CTEVETPIRNEWGSRCSLLTEVETPIRC | 1104 |
| 185 | CTPIRNEWGSRSNDSSCSLLTEVETPIRNC | 1103 |
| 186 | CSLLTEVETPCSLLTEVETPIRNEWGC | 1103 |
| 187 | CSLLTEVETPICSLLTEVETC | 1089 |
| 188 | CLTEVETPIRNEWGSRCSLLTEVETPIRNEWC | 1079 |

TABLE 2-continued

Peptides that specifically bind for 23K21 and 8I10 (A numeral "1" in the peptide sequence indicates a differentially protected cystein allowing for selective CLIP attachment at certain residues)

| SEQ ID NO: | Peptides that bind to 23K21 and 8I10 | Signal |
|---|---|---|
| 189 | CSLLTEVETPIRNEWCSLLTEVETPC | 1074 |
| 190 | CETPIRNEWGSRSNDSCSLLTEVETPIRC | 1069 |
| 191 | CLTEVETPIRNEWGSRCSLLTEVETPIC | 1040 |
| 192 | CSLLTEVETPIRNCLLTEVETPIRNEWGSC | 1036 |
| 193 | CSLLTEVETPCSLLTEVETPIRNEC | 1032 |
| 194 | CVETPIRNEWGSRSNDCSLLTEVETPIRNC | 1028 |
| 195 | CSLLTEVETPIRNCLTEVETPIRNEWGSRC | 1027 |
| 196 | CEVETPIRNEWGSRSNCSLLTEVETPIRNC | 1026 |
| 197 | CSLLTEVETPIRNEWGCSLLTEVETPIC | 1023 |
| 198 | CSLLTEVETPCSLLTEVETC | 1018 |
| 199 | CSLLTEVETPIRCTEVETPIRNEWGSRSC | 1017 |
| 200 | CSLLTEVETPIRNEWGCSLLTEVETC | 1014 |
| 201 | CEVETPIRNEWGSRSNCSLLTEVETC | 1007 |
| 202 | CPIRNEWGSRSNDSSDCSLLTEVETPIRNC | 1004 |
| 203 | CSLLTEVETPICSLLTEVETPIRC | 1001 |
| 204 | CTEVETPIRNEWGSRSCSLLTEVETPIRNC | 1000 |
| 205 | CLLTEVETPIRNEWGSCSLLTEVETPIRNEWGC | 1000 |
| 206 | CSLLTEVETPIRNEWGCSLLTEVETPIRNEC | 994 |
| 207 | CSLLTEVETPICSLLTEVETPC | 986 |
| 208 | CSLLTEVETPICSLLTEVETPIRNC | 981 |
| 209 | CSLLTEVETPIRCEVETPIRNEWGSRSNC | 980 |
| 210 | CSLLTEVETPIRNCTEVETPIRNEWGSRSC | 977 |
| 211 | CSLLTEVETPICSLLTEVETPIRNEWC | 975 |
| 212 | CSLLTEVETPIRNEWGCSLLTEVETPIRNEWC | 972 |
| 213 | CETPIRNEWGSRSNDSCSLLTEVETC | 971 |
| 214 | CSLLTEVETPIRNEWCLLTEVETPIRNEWGSC | 961 |
| 215 | CSLLTEVETCLTEVETPIRNEWGSRC | 958 |
| 216 | CTEVETPIRNEWGSRSCSLLTEVETPIC | 957 |
| 217 | CSLLTEVETPIRNEWGCSLLTEVETPC | 955 |
| 218 | CLLTEVETPIRNEWGSCSLLTEVETPIRNEWC | 922 |
| 219 | CEVETPIRNEWGSRSNCSLLTEVETPIC | 912 |
| 220 | CSLLTEVETPIRNECSLLTEVETPIRNEC | 910 |
| 221 | CSLLTEVETPCLTEVETPIRNEWGSRC | 907 |
| 222 | CSLLTEVETPCTEVETPIRNEWGSRSC | 907 |
| 223 | CVETPIRNEWGSRSNDCSLLTEVETC | 905 |
| 224 | CSLLTEVETPICLLTEVETPIRNEWGSC | 901 |
| 225 | CTEVETPIRNEWGSRSCSLLTEVETPIRNEWC | 900 |
| 226 | CTEVETPIRNEWGSRSCSLLTEVETC | 891 |
| 227 | CSLLTEVETPIRNECLLTEVETPIRNEWGSC | 870 |
| 228 | CLTEVETPIRNEWGSRCSLLTEVETPC | 867 |
| 229 | CEVETPIRNEWGSRSNCSLLTEVETPC | 862 |
| 230 | CTPIRNEWGSRSNDSSCSLLTEVETC | 861 |
| 231 | CTPIRNEWGSRSNDSSCSLLTEVETPIC | 854 |
| 232 | CETPIRNEWGSRSNDSCSLLTEVETPC | 842 |
| 233 | CEVETPIRNEWGSRSNCSLLTEVETPIRNEWGC | 838 |
| 234 | CVETPIRNEWGSRSNDCSLLTEVETPIRNEWC | 837 |
| 235 | CSLLTEVETPICLTEVETPIRNEWGSRC | 835 |
| 236 | CSLLTEVETPICSLLTEVETPIRNEWGC | 826 |
| 237 | CETPIRNEWGSRSNDSCSLLTEVETPIC | 825 |
| 238 | CEVETPIRNEWGSRSNCSLLTEVETPIRNEWC | 825 |
| 239 | CSLLTEVETCEVETPIRNEWGSRSNC | 821 |
| 240 | CLTEVETPIRNEWGSRCSLLTEVETPIRNEC | 817 |
| 241 | CSLLTEVETPIRNEWCSLLTEVETPIRNEC | 815 |
| 242 | CVETPIRNEWGSRSNDCSLLTEVETPC | 814 |
| 243 | CTPIRNEWGSRSNDSSCSLLTEVETPIRNEWGC | 812 |
| 244 | CLLTEVETPIRNEWGSCSLLTEVETPIRNEC | 808 |
| 245 | CSLLTEVETPICSLLTEVETPIC | 797 |
| 246 | CTEVETPIRNEWGSRSCSLLTEVETPC | 796 |
| 247 | CTPIRNEWGSRSNDSSCSLLTEVETPC | 794 |
| 248 | CPIRNEWGSRSNDSSDCSLLTEVETPIRNEC | 787 |
| 249 | CPIRNEWGSRSNDSSDCSLLTEVETPIRNEWC | 786 |
| 250 | CSLLTEVETCTEVETPIRNEWGSRSC | 786 |
| 251 | CETPIRNEWGSRSNDSCSLLTEVETPIRNEWC | 784 |
| 252 | CLLTEVETPIRNEWGSCSLLTEVETPIC | 762 |
| 253 | CSLLTEVETPIRNCEVETPIRNEWGSRSNC | 761 |
| 254 | CLLTEVETPIRNEWGSCSLLTEVETC | 752 |
| 255 | CETPIRNEWGSRSNDSCSLLTEVETPIRNEWGC | 749 |
| 256 | CPIRNEWGSRSNDSSDCSLLTEVETPIRNEWGC | 742 |
| 257 | CVETPIRNEWGSRSNDCSLLTEVETPIRNEWGC | 737 |
| 258 | CSLLTEVETPIRNECTEVETPIRNEWGSRSC | 736 |
| 259 | CPIRNEWGSRSNDSSDCSLLTEVETPC | 733 |

TABLE 2-continued

Peptides that specifically bind for 23K21 and 8I10 (A numeral "1" in the peptide sequence indicates a differentially protected cystein allowing for selective CLIP attachment at certain residues)

| SEQ ID NO: | Peptides that bind to 23K21 and 8I10 | Signal |
|---|---|---|
| 260 | CSLLTEVETPICEVETPIRNEWGSRSNC | 731 |
| 261 | CTEVETPIRNEWGSRSCSLLTEVETPIRNEC | 721 |
| 262 | CSLLTEVETPIRNCVETPIRNEWGSRSNDC | 721 |
| 263 | CSLLTEVETPIRNEWGCTEVETPIRNEWGSRSC | 715 |
| 264 | CSLLTEVETCVETPIRNEWGSRSNDC | 707 |
| 265 | CSLLTEVETPCVETPIRNEWGSRSNDC | 704 |
| 266 | CTPIRNEWGSRSNDSSCSLLTEVETPIRNEC | 699 |
| 267 | CPIRNEWGSRSNDSSDCSLLTEVETPIC | 691 |
| 268 | SLLTEVETPIRNECGCRCNDSSD | 682 |
| 269 | CVETPIRNEWGSRSNDCSLLTEVETPIRNEC | 679 |
| 270 | CLLTEVETPIRNEWGSCSLLTEVETPC | 678 |
| 271 | CSLLTEVETPIRCVETPIRNEWGSRSNDC | 678 |
| 272 | CTPIRNEWGSRSNDSSCSLLTEVETPIRNEWC | 677 |
| 273 | CEVETPIRNEWGSRSNCSLLTEVETPIRNEC | 669 |
| 274 | CSLLTEVETPCEVETPIRNEWGSRSNC | 650 |
| 275 | CSLLTEVETPIRNEWGCEVETPIRNEWGSRSNC | 607 |
| 276 | CSLLTEVETPIRNECEVETPIRNEWGSRSNC | 591 |
| 277 | CSLLTEVETPIRNEWCTEVETPIRNEWGSRSC | 575 |
| 278 | CSLLTEVETPIRNEWCLTEVETPIRNEWGSRC | 561 |
| 279 | CSLLTEVETPIRNECVETPIRNEWGSRSNDC | 538 |
| 280 | CSLLTEVETPICTEVETPIRNEWGSRSC | 526 |
| 281 | CSLLTEVETCSLLTEVETPIRNEWGC | 328 |
| 282 | CSCLCEVGMSCLCEC | 2705 |
| 283 | CSLLTEVGSLLTEV | 2494 |
| 284 | ASLLTEVGSLLTCV | 2443 |
| 285 | MSLLTEVGMSLLTCV | 2389 |
| 286 | CSLLTEVGMSLLTCV | 2311 |
| 287 | MSLLTEVGMSLLTEV | 2267 |
| 288 | CSCLCEVGMSLLTEV | 2154 |
| 289 | MSLCTEVGMSLCTEV | 2153 |
| 290 | CSLLTEVGSLLTCV | 2142 |
| 291 | MSLLTEVGMCLCTCV | 2110 |
| 292 | CSLLTEVGSLLTEC | 2094 |
| 293 | CSLLTEVGMSLLTEV | 2039 |
| 294 | MSCLCEVGMSLLTEV | 2039 |
| 295 | MSLCTEVGMSCLTEV | 2026 |
| 296 | MSLLTEVGMCLLTEV | 2023 |
| 297 | CSLLTEVGMCLCTCV | 1972 |
| 298 | SLCTEVGSCLCEC | 1967 |
| 299 | SLLTEVGCLCTCV | 1963 |
| 300 | SLLTEVETKIRNEWGCRCNDSSD | 1960 |
| 301 | SLLCEVGCSLLTEC | 1959 |
| 302 | ASLLTEVGSCLTEV | 1944 |
| 303 | CSLLTEVGMCLLTEV | 1941 |
| 304 | MSLCTEVGMSLLCEV | 1935 |
| 305 | CSCLCEVGMSLLTEC | 1925 |
| 306 | CSLLTECGMSLLTCV | 1918 |
| 307 | SLCTEVGCLCTCV | 1907 |
| 308 | MSLCTEVGMCLCTCV | 1902 |
| 309 | CSLLTEVGMSLLCEV | 1891 |
| 310 | MSCLCECGMSLLTEC | 1887 |
| 311 | SLLTEVGCLLTEV | 1859 |
| 312 | TLLTEVETPIRNEWGCRCNDSSD | 1855 |
| 313 | SLLTEVETPIRNEWGCRCNDSGD | 1852 |
| 314 | SLLTEVGSLLCEV | 1834 |
| 315 | MCLCTCVGCSLLTEC | 1823 |
| 316 | MSLLTEVGCSLLTEV | 1809 |
| 317 | MSLLTEVGMSLCTEV | 1804 |
| 318 | SLLTEVETPIRNEWGCRCKDSSD | 1802 |
| 319 | SLLTECGSLLTCV | 1800 |
| 320 | SLLTEVGSLLTEV | 1794 |
| 321 | ALLTEVETPIRNEWGCRCNDSSD | 1794 |
| 322 | SKLTEVETPIRNEWGCRCNDSSD | 1784 |
| 323 | SLCTEVGSLLTCV | 1781 |
| 324 | SLCTEVGSLLTEV | 1772 |
| 325 | SLLTECGSLLTEV | 1770 |
| 326 | SLLTEVETPIRNEWGCRCNDSSD | 1749 |
| 327 | SLMTEVETPIRNEWGCRCNDSSD | 1729 |
| 328 | SLETEVETPIRNEWGCRCNDSSD | 1720 |
| 329 | SLLTEVGSCLCEC | 1708 |
| 330 | SLLTEVETPIRNEWGCRCNDYSD | 1694 |

TABLE 2-continued

Peptides that specifically bind for 23K21 and 8I10 (A numeral "1" in the peptide sequence indicates a differentially protected cystein allowing for selective CLIP attachment at certain residues)

| SEQ ID NO: | Peptides that bind to 23K21 and 8I10 | Signal |
|---|---|---|
| 331 | MSLLTECGMSLLTCV | 1690 |
| 332 | SALTEVETPIRNEWGCRCNDSSD | 1689 |
| 333 | SLLTCVGSLLTEC | 1683 |
| 334 | CSLLTEVGMSLCTEV | 1682 |
| 335 | CSCLCEVGCSLLTEC | 1677 |
| 336 | SLLCEVGSLLTEV | 1674 |
| 337 | SLLTEVETPIRNEWGCRCNYSSD | 1666 |
| 338 | SLLTEVETPIRNEWGCRCNDGSD | 1666 |
| 339 | MSLLTECGMSLLTEV | 1658 |
| 340 | MSCLCECGCSLLTEC | 1652 |
| 341 | CSLLTEVCSLLTEC | 1644 |
| 342 | SLLTEVETPIRNEWGCRCNSSSD | 1637 |
| 343 | MSLLTEVGMSLLTEC | 1630 |
| 344 | SMLTEVETPIRNEWGCRCNDSSD | 1622 |
| 345 | CSLLTEVGSCLTEV | 1616 |
| 346 | SLLMEVETPIRNEWGCRCNDSSD | 1616 |
| 347 | SLLTEVETPIRNEWICRCNDSSD | 1599 |
| 348 | SLLTECGCSLLTEV | 1597 |
| 349 | SLATEVETPIRNEWGCRCNDSSD | 1583 |
| 350 | SLLTEVETPIRNEWGCRCNDSND | 1577 |
| 351 | SLLCEVGSLLTEC | 1564 |
| 352 | SLQTEVETPIRNEWGCRCNDSSD | 1561 |
| 353 | SLLTEVGCSLLTEC | 1556 |
| 354 | SLLTEVGCSLLTEV | 1555 |
| 355 | SCLCECGCSLLTEV | 1555 |
| 356 | SLLTEVETPIRNEWGCRCNDSDD | 1553 |
| 357 | SLLTEVETPIPNEWGCRCNDSSD | 1548 |
| 358 | SFLTEVETPIRNEWGCRCNDSSD | 1546 |
| 359 | MSLLTEVGMSCLTEV | 1535 |
| 360 | CSLLTECGCSLLTEV | 1534 |
| 361 | SCLCECGCSLLTEC | 1520 |
| 362 | CSLLTECGMCLLTEV | 1517 |
| 363 | MSLLTECGCSLLTEV | 1500 |
| 364 | CSLLTEVGCSLLTEV | 1499 |
| 365 | CSLLTEVCMSLLTEC | 1498 |
| 366 | SLLTEVETPIRNEWWCRCNDSSD | 1498 |
| 367 | SLCTEVGSLLTEC | 1495 |
| 368 | SLLTEVETPIRNEWG | 1486 |
| 369 | SLLTEAETPIRNEWGCRCNDSSD | 1481 |
| 370 | SLLTEVETPIRNEWGERCNDSSD | 1474 |
| 371 | MSLCTEVGMSLLTEV | 1468 |
| 372 | CSLLTEVGMSCLTEV | 1466 |
| 373 | CSLLTECGMSLLTEV | 1458 |
| 374 | SLLTECGCSLLTEC | 1451 |
| 375 | SLLTEVETPIRNEWGCRVNDSSD | 1446 |
| 376 | CSLLTECGMSLLTEC | 1445 |
| 377 | SLKTEVETPIRNEWGCRCNDSSD | 1434 |
| 378 | SLLTECGSLLTEC | 1426 |
| 379 | SLCTEVGCSCLCEV | 1421 |
| 380 | SLLTEVETPIRNTWGCRCNDSSD | 1409 |
| 381 | SLLQEVETPIRNEWGCRCNDSSD | 1399 |
| 382 | CSLLTECGSLLTEV | 1393 |
| 383 | CSLLTEVGCSLLTEC | 1380 |
| 384 | SLLTEVETPIRNEYGCRCNDSSD | 1377 |
| 385 | CSLLTEVGCLCTCV | 1375 |
| 386 | SLLTEVETPIRNEVGCRCNDSSD | 1371 |
| 387 | SLLTEVETPIRTEWGCRCNDSSD | 1365 |
| 388 | CSLLTEVGCLLTEV | 1351 |
| 389 | SLLTEVETPYRNEWGCRCNDSSD | 1350 |
| 390 | CLLTEVGSLLTEV | 1349 |
| 391 | SNLTEVETPIRNEWGCRCNDSSD | 1345 |
| 392 | SLLTEVETPKRNEWGCRCNDSSD | 1342 |
| 393 | SLLTEVETPIRNEWGCRCNLSSD | 1334 |
| 449 | SLNTEVETPIRNEWGCRCNDSSD | 1333 |
| 450 | SLLTEVEHPIRNEWGCRCNDSSD | 1331 |
| 451 | CSLLTEVGMSLLTEC | 1326 |
| 452 | SLLTEVGSLLTEC | 1326 |
| 453 | SLLTEVETPIRNEAGCRCNDSSD | 1311 |
| 454 | SLLTEVETPIMNEWGCRCNDSSD | 1308 |
| 455 | CLCTCVGSLLTEC | 1303 |
| 456 | CSLLTECGMSLLCEV | 1294 |

TABLE 2-continued

Peptides that specifically bind for 23K21 and 8I10 (A numeral "1" in the peptide sequence indicates a differentially protected cystein allowing for selective CLIP attachment at certain residues)

| SEQ ID NO: | Peptides that bind to 23K21 and 8I10 | Signal |
|---|---|---|
| 457 | SLLTEVETPMRNEWGCRCNDSSD | 1281 |
| 458 | CSLLTECGSCLTEV | 1278 |
| 459 | SLITEVETPIRNEWGCRCNDSSD | 1277 |
| 460 | MSLLTECGMSLLCEV | 1268 |
| 461 | SLLTEVETPLRNEWGCRCNDSSD | 1268 |
| 462 | SLLTECGCLLTEV | 1259 |
| 463 | CSLLTECGSLLTCV | 1258 |
| 464 | SLLTEVGSLCTEV | 1256 |
| 465 | SLLTEVETPIRNEWGCRCNKSSD | 1254 |
| 466 | SCLTEVGCSLLTEV | 1250 |
| 467 | SLLTEVENPIRNEWGCRCNDSSD | 1245 |
| 468 | SCLCECGSLLTEC | 1244 |
| 469 | MSLLTECGMSLLTEC | 1236 |
| 470 | MSLLTEVGCSLLTEC | 1227 |
| 471 | SLLTEEETPIRNEWGCRCNDSSD | 1220 |
| 472 | SLLTECGSLCTEV | 1218 |
| 473 | SLSTEVETPIRNEWGCRCNDSSD | 1217 |
| 474 | SLLTECETPIRNEWGCRCNDSSD | 1214 |
| 475 | MSLLTECGMSLCTEV | 1212 |
| 476 | CSLLTEVGCSCLCEV | 1206 |
| 477 | SLLTECGSLLCEV | 1206 |
| 478 | SLTTEVETPIRNEWGCRCNDSSD | 1205 |
| 407 | SLLTEVETPIRNEWGCRCNDHSD | 1200 |
| 479 | SLLTEDETPIRNEWGCRCNDSSD | 1196 |
| 480 | SLLTECGCLCTCV | 1193 |
| 481 | CSLLTECGMSLCTEV | 1187 |
| 482 | CLCTCVGSLLTEV | 1178 |
| 483 | CSLLTECGCSLLTEC | 1177 |
| 484 | SLVTEVETPIRNEWGCRCNDSSD | 1175 |
| 485 | CSLLTECGMCLCTCV | 1168 |
| 486 | SLFTEVETPIRNEWGCRCNDSSD | 1156 |
| 487 | SLLTNVETPIRNEWGCRCNDSSD | 1142 |
| 394 | SLLTEVETPIRNEWGCRCNMSSD | 1133 |
| 488 | SLLTEVETPIHNEWGCRCNDSSD | 1112 |
| 489 | MSLLTECGMCLLTEV | 1111 |
| 490 | SVLTEVETPIRNEWGCRCNDSSD | 1109 |
| 491 | SLLTEVETLIRNEWGCRCNDSSD | 1109 |
| 492 | MSLLTECGMCLCTCV | 1107 |
| 493 | SLLTEVETMIRNEWGCRCNDSSD | 1104 |
| 494 | SLLTEQETPIRNEWGCRCNDSSD | 1102 |
| 495 | SLLTEVETPGRNEWGCRCNDSSD | 1097 |
| 496 | SCLTEVGSLLCEV | 1095 |
| 436 | SLLTEVETPI | 1084 |
| 497 | SLLTECGSCLCEC | 1077 |
| 498 | SLLTEMETPIRNEWGCRCNDSSD | 1076 |
| 499 | CSLLTEVGMSCLCEC | 1066 |
| 500 | SCLTEVGSLLTEV | 1066 |
| 501 | SLLTEVETPIRNEWGCCCNDSSD | 1065 |
| 502 | CSCLCEVGSLLTEC | 1064 |
| 503 | SLLTEVETPIRNEWGCWCNDSSD | 1061 |
| 504 | SLLTEVETPIRNEWGFRCNDSSD | 1057 |
| 505 | SLLTEKETPIRNEWGCRCNDSSD | 1055 |
| 506 | SLCTEVGSLLCEV | 1050 |
| 507 | SLCTEVETPIRNEWGCRCNDSSD | 1050 |
| 508 | MSLCTEVGCSLLTEV | 1049 |
| 509 | SLLTEVETPIYNEWGCRCNDSSD | 1049 |
| 510 | SLRTEVETPIRNEWGCRCNDSSD | 1047 |
| 511 | SLLCEVGCSLLTEV | 1044 |
| 512 | SLLTEVETPIRNQWGCRCNDSSD | 1039 |
| 513 | MCLLTEVGMSLLTEV | 1032 |
| 514 | SLLTEGETPIRNEWGCRCNDSSD | 1029 |
| 515 | SLLTEWETPIRNEWGCRCNDSSD | 1025 |
| 516 | SLLTEVETPIRNEWGCRCPDSSD | 1024 |
| 517 | SLLTEVETPIRNEMGCRCNDSSD | 1020 |
| 518 | SYLTEVETPIRNEWGCRCNDSSD | 1019 |
| 519 | SLLTEVETPIRNEWGCRSNDSSD | 1016 |
| 520 | VLLTEVETPIRNEWGCRCNDSSD | 1014 |
| 437 | SLLTEVETPIR | 1012 |
| 521 | SLLTAVETPIRNEWGCRCNDSSD | 1012 |
| 522 | SLLTMVETPIRNEWGCRCNDSSD | 1011 |
| 523 | SLLTEFETPIRNEWGCRCNDSSD | 1009 |

TABLE 2-continued

Peptides that specifically bind for 23K21 and 8I10 (A numeral "1" in the peptide sequence indicates a differentially protected cystein allowing for selective CLIP attachment at certain residues)

| SEQ ID NO: | Peptides that bind to 23K21 and 8I10 | Signal |
|---|---|---|
| 524 | SLLTEVETPIDNEWGCRCNDSSD | 1001 |
| 401 | SLLTEVETPIRNEWGCRCNWSSD | 999 |
| 525 | SLLTEVGCSCLCEV | 996 |
| 526 | MSLLTECGMSCLCEC | 992 |
| 527 | SLLTEVEQPIRNEWGCRCNDSSD | 986 |
| 528 | MSLLTCVGCSLLTEV | 978 |
| 529 | SLLTEVETNIRNEWGCRCNDSSD | 978 |
| 445 | SLLTEVETPIRNEWGCRCN | 977 |
| 530 | SLLTESETPIRNEWGCRCNDSSD | 974 |
| 433 | SLLTEVETPIRNEWGCRCNDSWD | 971 |
| 531 | MSLCTEVGMSLLTEC | 970 |
| 532 | MSCLTEVGMSLLTEV | 968 |
| 533 | CSLLTEVGSCLCEC | 963 |
| 534 | SLLTEVEKPIRNEWGCRCNDSSD | 963 |
| 535 | SLLTEVETPIRNEWGCRCNFSSD | 963 |
| 408 | SLLTEVETPIRNEWGCRCNDISD | 962 |
| 536 | MCLCTCVGCSLLTEV | 954 |
| 537 | SLLTEVEPPIRNEWGCRCNDSSD | 953 |
| 538 | LLLTEVETPIRNEWGCRCNDSSD | 950 |
| 539 | SLLTEYETPIRNEWGCRCNDSSD | 950 |
| 422 | SLLTEVETPIRNEWGCRCNDSFD | 947 |
| 421 | SLLTEVETPIRNEWGCRCNDSED | 944 |
| 540 | SLLTEHETPIRNEWGCRCNDSSD | 942 |
| 541 | SLLTEVETPIRNEWKCRCNDSSD | 932 |
| 418 | SLLTEVETPIRNEWGCRCNDWSD | 929 |
| 542 | MSLCTEVGMSLLTCV | 927 |
| 395 | SLLTEVETPIRNEWGCRCNNSSD | 926 |
| 543 | MSLLTCVGMSLLTEV | 925 |
| 544 | SLLTEVETPIRNEWGCRCRDSSD | 924 |
| 545 | SLLTEVSTPIRNEWGCRCNDSSD | 923 |
| 546 | SLLTEVETPIRNRWGCRCNDSSD | 921 |
| 547 | SLLTETETPIRNEWGCRCNDSSD | 919 |
| 548 | CSLLTECGSLCTEV | 917 |
| 549 | SLLTEVETFIRNEWGCRCNDSSD | 916 |
| 550 | SLLTENETPIRNEWGCRCNDSSD | 914 |
| 551 | SLLTEVATPIRNEWGCRCNDSSD | 914 |
| 552 | SLLTEVETPIRNEWGCYCNDSSD | 913 |
| 553 | SLLTEVTTPIRNEWGCRCNDSSD | 909 |
| 554 | CLLTEVGSLLTCV | 902 |
| 555 | SLLTEVETPIRNEWGCRCWDSSD | 901 |
| 556 | SLLTELETPIRNEWGCRCNDSSD | 900 |
| 557 | MSCLTEVGCSLLTEV | 899 |
| 435 | SLLTEVETP | 899 |
| 409 | SLLTEVETPIRNEWGCRCNDKSD | 898 |
| 444 | SLLTEVETPIRNEWGCRC | 898 |
| 558 | CSLLTECGMSCLCEC | 897 |
| 559 | SLLTEVETAIRNEWGCRCNDSSD | 895 |
| 560 | SLLTEVETPIRNEWGCRCFDSSD | 894 |
| 561 | SCLTEVETPIRNEWGCRCNDSSD | 892 |
| 562 | SLLTEVETPIRWEWGCRCNDSSD | 890 |
| 398 | SLLTEVETPIRNEWGCRCNRSSD | 890 |
| 563 | SLLTEVETPIRNEWGGRCNDSSD | 887 |
| 564 | SLLTEVLPIRNEWGCRCNDSSD | 886 |
| 565 | SLLTEVETPIRVEWGCRCNDSSD | 884 |
| 566 | SLLTEVCTPIRNEWGCRCNDSSD | 881 |
| 567 | SLLTECGCSCLCEV | 879 |
| 568 | SLLTEVETPIRNEWGCRCQDSSD | 877 |
| 569 | SLLTEVETPIRNEWLCRCNDSSD | 876 |
| 570 | MCLLTEVGCSLLTEV | 875 |
| 571 | SLLTEVETPIRNLWGCRCNDSSD | 870 |
| 572 | SLLTEVETPIRNEKGCRCNDSSD | 868 |
| 573 | SLLTEVETPIRNEWGCRTNDSSD | 867 |
| 574 | CLLTEVGSLLTEC | 866 |
| 575 | SLLTEVRTPIRNEWGCRCNDSSD | 866 |
| 400 | SLLTEVETPIRNEWGCRCNVSSD | 865 |
| 443 | SLLTEVETPIRNEWGCR | 864 |
| 576 | SLLTEVETPIFNEWGCRCNDSSD | 862 |
| 577 | SLLTEVETPIRNIWGCRCNDSSD | 862 |
| 434 | SLLTEVETPIRNEWGCRCNDSYD | 862 |
| 415 | SLLTEVETPIRNEWGCRCNDRSD | 860 |
| 578 | SLLTERETPIRNEWGCRCNDSSD | 859 |

TABLE 2-continued

Peptides that specifically bind for 23K21 and 8I10 (A numeral "1" in the peptide sequence indicates a differentially protected cystein allowing for selective CLIP attachment at certain residues)

| SEQ ID NO: | Peptides that bind to 23K21 and 8I10 | Signal |
|---|---|---|
| 579 | SLLTEVETPIRNEWGCRWNDSSD | 859 |
| 580 | SLCTEVGCSLLTEV | 858 |
| 581 | SLLTEVETYIRNEWGCRCNDSSD | 857 |
| 582 | SLLTEVETPIRAEWGCRCNDSSD | 856 |
| 583 | SLLTEVWTPIRNEWGCRCNDSSD | 855 |
| 584 | SLLTEVETPIRNEWGCRRNDSSD | 855 |
| 585 | SLLTEVETPIRLEWGCRCNDSSD | 853 |
| 586 | SLLTEVETPIRNEWGCRCNISSD | 851 |
| 587 | SLLTEVETPIRCEWGCRCNDSSD | 850 |
| 396 | SLLTEVETPIRNEWGCRCNPSSD | 849 |
| 588 | SLLTEVETPIRNEWGCRCNCSSD | 848 |
| 589 | CSLLTECGMSCLTEV | 846 |
| 590 | SLLTEVEMPIRNEWGCRCNDSSD | 845 |
| 591 | SLLTEVETPHRNEWGCRCNDSSD | 844 |
| 397 | SLLTEVETPIRNEWGCRCNQSSD | 842 |
| 592 | MSLCTEVGCSLLTEC | 840 |
| 593 | SLLTEVEIPIRNEWGCRCNDSSD | 839 |
| 594 | SLLTEVQTPIRNEWGCRCNDSSD | 838 |
| 595 | SLLTEVETPIRNEWGWRCNDSSD | 838 |
| 596 | SLLTEVETPIRNEWFCRCNDSSD | 837 |
| 597 | SLLTEVETGIRNEWGCRCNDSSD | 835 |
| 598 | SLLTEVETPIRNEWGCRKNDSSD | 835 |
| 599 | SLLTEVERPIRNEWGCRCNDSSD | 834 |
| 430 | SLLTEVETPIRNEWGCRCNDSRD | 833 |
| 448 | SLLTEVETPIRNEWGCRCNDSS | 833 |
| 600 | SLLTEVETPIRNEWGLRCNDSSD | 831 |
| 601 | SLLTECGSCLTEV | 830 |
| 602 | SLLTEVETEIRNEWGCRCNDSSD | 828 |
| 603 | SLLTEVETPIRNEWGCRCNGSSD | 828 |
| 604 | SLCTEVGSCLTEV | 824 |
| 605 | SLLTEVETPIRNMWGCRCNDSSD | 820 |
| 606 | SLLTEVETQIRNEWGCRCNDSSD | 819 |
| 607 | SLLTEVESPIRNEWGCRCNDSSD | 817 |
| 447 | SLLTEVETPIRNEWGCRCNDS | 817 |
| 608 | SLLTEIETPIRNEWGCRCNDSSD | 816 |
| 609 | SLLTEVETHIRNEWGCRCNDSSD | 816 |
| 610 | SLLTEVETDIRNEWGCRCNDSSD | 813 |
| 611 | SLLTEVETRIRNEWGCRCNDSSD | 813 |
| 612 | SLLTEVETPIRNEWGCRCIDSSD | 812 |
| 613 | SLLTEVETPIRNEWGCRCNHSSD | 812 |
| 614 | SLLTEVETVIRNEWGCRCNDSSD | 810 |
| 615 | SLLTEVETPIRNEWGCDCNDSSD | 810 |
| 616 | SLLTEVETPIRNPWGCRCNDSSD | 808 |
| 617 | SLLTEVETPIRNSWGCRCNDSSD | 807 |
| 618 | SLLTEVETPIRNEWGCRCLDSSD | 807 |
| 619 | SLLTEVETPIRNEWGCRCNASSD | 807 |
| 620 | SLLTEVETPIRFEWGCRCNDSSD | 806 |
| 621 | SLLTEVEFPIRNEWGCRCNDSSD | 805 |
| 622 | SLLTEVETPIRMEWGCRCNDSSD | 805 |
| 623 | SLLTEVETCIRNEWGCRCNDSSD | 800 |
| 624 | SLLTEVETPIRNEWVCRCNDSSD | 799 |
| 413 | SLLTEVETPIRNEWGCRCNDPSD | 797 |
| 399 | SLLTEVETPIRNEWGCRCNTSSD | 795 |
| 625 | SLLTEVETPIRNEWYCRCNDSSD | 794 |
| 416 | SLLTEVETPIRNEWGCRCNDTSD | 794 |
| 626 | SLLTEVETPIRNEWGCRCYDSSD | 791 |
| 627 | SLLTEVETPIRIEWGCRCNDSSD | 789 |
| 406 | SLLTEVETPIRNEWGCRCNDFSD | 788 |
| 628 | SLLTEVETPIRNEWGCRCMDSSD | 786 |
| 629 | SLLTEVMTPIRNEWGCRCNDSSD | 783 |
| 630 | SLLTEVETPERNEWGCRCNDSSD | 783 |
| 631 | SLLTEVETPIRKEWGCRCNDSSD | 782 |
| 423 | SLLTEVETPIRNEWGCRCNDSHD | 782 |
| 426 | SLLTEVETPIRNEWGCRCNDSLD | 779 |
| 632 | SLLTEVETPIRNEWGCRCVDSSD | 775 |
| 633 | SLLTEVETPIRNEWHCRCNDSSD | 772 |
| 403 | SLLTEVETPIRNEWGCRCNDCSD | 772 |
| 417 | SLLTEVETPIRNEWGCRCNDVSD | 772 |
| 428 | SLLTEVETPIRNEWGCRCNDSPD | 772 |
| 634 | SLLTEVETPIRNEWGCRANDSSD | 770 |
| 425 | SLLTEVETPIRNEWGCRCNDSKD | 770 |

TABLE 2-continued

Peptides that specifically bind for 23K21 and 8I10 (A numeral "1" in the peptide sequence indicates a differentially protected cystein allowing for selective CLIP attachment at certain residues)

| SEQ ID NO: | Peptides that bind to 23K21 and 8I10 | Signal |
| --- | --- | --- |
| 635 | SLLTEVEAPIRNEWGCRCNDSSD | 769 |
| 410 | SLLTEVETPIRNEWGCRCNDLSD | 769 |
| 636 | SLLTEVETPIRNEIGCRCNDSSD | 768 |
| 637 | SLLTEVETPIRNENGCRCNDSSD | 768 |
| 638 | SLLTEVETPIRNEWGTRCNDSSD | 767 |
| 639 | SLLTEVETPIRNEWGCFCNDSSD | 767 |
| 640 | SLLTEVETPIRNKWGCRCNDSSD | 765 |
| 641 | SLLTEVETPIRNELGCRCNDSSD | 765 |
| 642 | SLLTEVETPIRNEWMCRCNDSSD | 765 |
| 643 | SLLTEVETPIRNGWGCRCNDSSD | 764 |
| 644 | SLLTEVETPIRNEWGVRCNDSSD | 764 |
| 645 | SLLTEVVTPIRNEWGCRCNDSSD | 763 |
| 646 | SLLTEVEGPIRNEWGCRCNDSSD | 763 |
| 647 | SLLTEVETPIRNEWGHRCNDSSD | 763 |
| 648 | SLLTEVETPIRNEWGKRCNDSSD | 762 |
| 649 | SLLTEVETTIRNEWGCRCNDSSD | 760 |
| 650 | SLLTEVETPVRNEWGCRCNDSSD | 758 |
| 651 | SLLTEVETPIRNEWGCRCHDSSD | 758 |
| 652 | SLLTEVEEPIRNEWGCRCNDSSD | 757 |
| 653 | SLLTEVETIIRNEWGCRCNDSSD | 756 |
| 654 | SLLTEVETPIRYEWGCRCNDSSD | 755 |
| 655 | SLYTEVETPIRNEWGCRCNDSSD | 753 |
| 656 | SLLTEVETPIWNEWGCRCNDSSD | 753 |
| 657 | SLLTEVDTPIRNEWGCRCNDSSD | 751 |
| 658 | SLLTEVYTPIRNEWGCRCNDSSD | 751 |
| 438 | SLLTEVETPIRN | 751 |
| 659 | SLLTEVETPIRNEWGARCNDSSD | 750 |
| 440 | SLLTEVETPIRNEW | 750 |
| 660 | SLLTEVETPDRNEWGCRCNDSSD | 749 |
| 661 | SLLTEVETPIRQEWGCRCNDSSD | 748 |
| 662 | SLLTEVETPIRNFWGCRCNDSSD | 747 |
| 663 | MCLCTCVGMSLLTEV | 746 |
| 664 | SLLTEVETPIRNEWGNRCNDSSD | 746 |
| 665 | SLLTEVETPFRNEWGCRCNDSSD | 745 |
| 411 | SLLTEVETPIRNEWGCRCNDMSD | 744 |
| 666 | SLLTEVETPIRNAWGCRCNDSSD | 743 |
| 667 | SLLTEVETPIRNEWGIRCNDSSD | 739 |
| 668 | SLLTEVETPIRNEWGYRCNDSSD | 739 |
| 414 | SLLTEVETPIRNEWGCRCNDQSD | 739 |
| 669 | SLLTEVETPIRNEWTCRCNDSSD | 738 |
| 446 | SLLTEVETPIRNEWGCRCND | 738 |
| 670 | SLLTEVETWIRNEWGCRCNDSSD | 736 |
| 671 | SLLTEVETPIRNEPGCRCNDSSD | 735 |
| 672 | SLLTEVETPIRNEWGRRCNDSSD | 735 |
| 673 | SLLTEVETPSRNEWGCRCNDSSD | 733 |
| 674 | SLLTEVETPIRNEWGCRCTDSSD | 733 |
| 675 | SLLTEVNTPIRNEWGCRCNDSSD | 732 |
| 676 | SLLTEVETPIENEWGCRCNDSSD | 731 |
| 677 | SLLTEVETPIQNEWGCRCNDSSD | 731 |
| 678 | SLLTEVETPIRSEWGCRCNDSSD | 730 |
| 679 | SLLTEVETPIRNEWGCECNDSSD | 730 |
| 680 | SLLTEVETPIVNEWGCRCNDSSD | 729 |
| 681 | SLLTEVETPIRNEWACRCNDSSD | 729 |
| 682 | SLLTEVETPIRNEWGSRCNDSSD | 729 |
| 683 | SLLTEVETPIRNEWGCACNDSSD | 729 |
| 684 | SLLTEVETPIRNHWGCRCNDSSD | 728 |
| 685 | SLLTEVETPIRNVWGCRCNDSSD | 728 |
| 686 | SLLTEVETPIRNEWGCRLNDSSD | 728 |
| 432 | SLLTEVETPIRNEWGCRCNDSVD | 728 |
| 420 | SLLTEVETPIRNEWGCRCNDSCD | 725 |
| 687 | SLLTEVETPCRNEWGCRCNDSSD | 724 |
| 688 | SLLTEVETPIRNETGCRCNDSSD | 724 |
| 689 | SLLTEVETPIRNEWGCRCGDSSD | 724 |
| 690 | SLLTEVHTPIRNEWGCRCNDSSD | 722 |
| 691 | SLLTEVETPIRNEWGCRMNDSSD | 722 |
| 692 | SLLTEVETPILNEWGCRCNDSSD | 721 |
| 693 | SLLTEVETPWRNEWGCRCNDSSD | 720 |
| 694 | SLLTEVETPIRNEWGCRCNESSD | 720 |
| 695 | SLLTEVEVPIRNEWGCRCNDSSD | 719 |
| 696 | SLLTEVETPIRNEHGCRCNDSSD | 719 |
| 697 | SLLTEVETPIRNEWGCRINDSSD | 718 |

TABLE 2-continued

Peptides that specifically bind for 23K21 and 8I10 (A numeral "1" in the peptide sequence indicates a differentially protected cystein allowing for selective CLIP attachment at certain residues)

| SEQ ID NO: | Peptides that bind to 23K21 and 8I10 | Signal |
|---|---|---|
| 698 | SLLTEVETPIRDEWGCRCNDSSD | 716 |
| 699 | SLLTEVETPIRNEWGCRYNDSSD | 716 |
| 700 | SLLTEVETSIRNEWGCRCNDSSD | 715 |
| 701 | SLLTEVETPIRNEWGCKCNDSSD | 715 |
| 702 | SLLTEVETPIRNYWGCRCNDSSD | 714 |
| 703 | SLLTEVETPIRNWWGCRCNDSSD | 713 |
| 704 | SLLTEVETPIRNEWRCRCNDSSD | 713 |
| 705 | SLLTEVKTPIRNEWGCRCNDSSD | 712 |
| 706 | SLLTEVETPIRNEWGCRCADSSD | 712 |
| 707 | SLLTEVETPIANEWGCRCNDSSD | 708 |
| 708 | SLLTEVETPIRNEGGCRCNDSSD | 708 |
| 412 | SLLTEVETPIRNEWGCRCNDNSD | 708 |
| 709 | SLLTEVLTPIRNEWGCRCNDSSD | 707 |
| 710 | SLLTEVETPIRREWGCRCNDSSD | 707 |
| 711 | CSLLTEVGSLCTEV | 707 |
| 712 | SLLTEVETPIRNDWGCRCNDSSD | 706 |
| 713 | SLLTEVETPIRNEWGQRCNDSSD | 705 |
| 714 | SLLTEVETPIRNEWCCRCNDSSD | 704 |
| 715 | SLLTEVETPARNEWGCRCNDSSD | 702 |
| 716 | SLLTEVETPIRNEFGCRCNDSSD | 702 |
| 717 | SLLTEVETPIRNEWDCRCNDSSD | 701 |
| 431 | SLLTEVETPIRNEWGCRCNDSTD | 701 |
| 718 | SLLTEVECPIRNEWGCRCNDSSD | 700 |
| 719 | SLLTEVETPIRNEWGCTCNDSSD | 700 |
| 720 | SLLTEVETPIINEWGCRCNDSSD | 699 |
| 721 | SLLTEVETPIRHEWGCRCNDSSD | 699 |
| 722 | SLLTEVETPIRNEWGCICNDSSD | 699 |
| 723 | SLLTEVETPIRNEWGCRFNDSSD | 698 |
| 724 | MCLLTEVGMSLLTEC | 697 |
| 725 | SLLTEVETPICNEWGCRCNDSSD | 697 |
| 726 | SLLTEVETPIRNEWECRCNDSSD | 697 |
| 727 | SLLTEVETPIRNEWGPRCNDSSD | 696 |
| 728 | SLLTEVETPIRNEWGCRCCDSSD | 696 |
| 729 | SLLTEVETPIRNEWGCRCSDSSD | 696 |
| 730 | SLLTEVETPIRNEWGCMCNDSSD | 695 |
| 429 | SLLTEVETPIRNEWGCRCNDSQD | 695 |
| 731 | SLLTEVFTPIRNEWGCRCNDSSD | 694 |
| 732 | SLLTEVETPIRNEWGMRCNDSSD | 693 |
| 733 | SLLTEVETPIRNCWGCRCNDSSD | 692 |
| 734 | SLLTEVETPIRNEWGCRHNDSSD | 692 |
| 424 | SLLTEVETPIRNEWGCRCNDSID | 692 |
| 735 | SLLTEVETPIRNEWSCRCNDSSD | 691 |
| 736 | SLLTEVETPIRNEWGCSCNDSSD | 691 |
| 737 | SLLTEVETPIRNERGCRCNDSSD | 690 |
| 738 | SLLTEVETPPRNEWGCRCNDSSD | 689 |
| 739 | SLLTEVETPIRNEWGCRCEDSSD | 687 |
| 740 | SHLTEVETPIRNEWGCRCNDSSD | 686 |
| 741 | SLLTEVETPIRNNWGCRCNDSSD | 686 |
| 742 | SLLTEVETPIRNEWGCVCNDSSD | 684 |
| 404 | SLLTEVETPIRNEWGCRCNDDSD | 684 |
| 743 | SLLTEVETPIRNEWGCNCNDSSD | 683 |
| 402 | SLLTEVETPIRNEWGCRCNDASD | 683 |
| 744 | SLLTEVETPIGNEWGCRCNDSSD | 681 |
| 745 | SLLTEVETPIRNESGCRCNDSSD | 681 |
| 746 | SLLTEVETPIRNEWGCRNNDSSD | 681 |
| 747 | SLCTEVGCSLLTEC | 680 |
| 748 | SLLTEVETPIRNEWGCLCNDSSD | 680 |
| 442 | SLLTEVETPIRNEWGC | 680 |
| 749 | MSLLCEVGMSLLTEV | 677 |
| 750 | SLLTEVETPRRNEWGCRCNDSSD | 677 |
| 405 | SLLTEVETPIRNEWGCRCNDESD | 676 |
| 751 | SLLTEVETPIRNEDGCRCNDSSD | 675 |
| 752 | SLLTEVETPIRNEWGCRGNDSSD | 674 |
| 753 | SLLTEVETPIRPEWGCRCNDSSD | 673 |
| 754 | SLLTEVETPISNEWGCRCNDSSD | 672 |
| 755 | SLLTQVETPIRNEWGCRCNDSSD | 671 |
| 756 | SLLTEVETPIRNEWGCQCNDSSD | 671 |
| 757 | SLLTEVETPIRNEWGCRPNDSSD | 669 |
| 758 | SLLTEVETPTRNEWGCRCNDSSD | 668 |
| 427 | SLLTEVETPIRNEWGCRCNDSMD | 668 |
| 759 | SLHTEVETPIRNEWGCRCNDSSD | 667 |

TABLE 2-continued

Peptides that specifically bind for 23K21 and 8I10 (A numeral "1" in the peptide sequence indicates a differentially protected cystein allowing for selective CLIP attachment at certain residues)

| SEQ ID NO: | Peptides that bind to 23K21 and 8I10 | Signal |
|---|---|---|
| 760 | SLLTEVETPIRNEWQCRCNDSSD | 667 |
| 761 | MSLLTEVGCSCLCEV | 663 |
| 762 | SLLTEVETPIRNEWGCRCDDSSD | 662 |
| 763 | SLLTEVEWPIRNEWGCRCNDSSD | 660 |
| 764 | SLLTEPETPIRNEWGCRCNDSSD | 659 |
| 765 | SLLTEVETPIRNEQGCRCNDSSD | 657 |
| 766 | SLLTEVETPITNEWGCRCNDSSD | 653 |
| 767 | SLLTEVETPIRNEWGCPCNDSSD | 653 |
| 768 | MSCLTEVGMSLLTEC | 650 |
| 769 | MCLLTEVGCSLLTEC | 650 |
| 770 | SLLTEVETPNRNEWGCRCNDSSD | 649 |
| 771 | SLLTEVETPIREEWGCRCNDSSD | 648 |
| 772 | SLLTEVETPIRNEWGCRQNDSSD | 646 |
| 773 | SLLTEVETPIRGEWGCRCNDSSD | 644 |
| 774 | SLLTEVETPIRNEWPCRCNDSSD | 644 |
| 775 | SLLTEVETPIRNEWGCGCNDSSD | 644 |
| 776 | SLLTEVETPIRNEWGCHCNDSSD | 640 |
| 777 | SLLTEVPTPIRNEWGCRCNDSSD | 639 |
| 419 | SLLTEVETPIRNEWGCRCNDSAD | 639 |
| 778 | SLLTEVETPIKNEWGCRCNDSSD | 638 |
| 779 | SLLTEVEDPIRNEWGCRCNDSSD | 635 |
| 780 | SLLTEVETPINNEWGCRCNDSSD | 632 |
| 781 | MSLLCEVGCSLLTEV | 631 |
| 782 | SLLTEVETPQRNEWGCRCNDSSD | 630 |
| 783 | SLLTEVEYPIRNEWGCRCNDSSD | 628 |
| 784 | SLLTEVGTPIRNEWGCRCNDSSD | 627 |
| 785 | SLLTEVETPIRNEWNCRCNDSSD | 618 |
| 786 | SWLTEVETPIRNEWGCRCNDSSD | 615 |
| 787 | SLLTEVETPIRNEEGCRCNDSSD | 613 |
| 788 | SQLTEVETPIRNEWGCRCNDSSD | 609 |
| 789 | SLCTEVGSLCTEV | 607 |
| 790 | SLLTEVETPIRNEWGDRCNDSSD | 603 |
| 791 | MSLCTEVGMCLLTEV | 597 |
| 792 | CSLLTEVGSLLCEV | 593 |
| 793 | MSLLTEVGMSLLCEV | 591 |
| 794 | SLLTEVETPIRNEWGCRDNDSSD | 589 |
| 795 | SLLTEVITPIRNEWGCRCNDSSD | 587 |
| 796 | SLLTEVETPIRNEWGCRENDSSD | 579 |
| 797 | SCLTEVGSLLTCV | 573 |
| 798 | CLCTCVGCSLLTEV | 567 |
| 799 | MSCLTEVGCSLLTEC | 557 |
| 800 | MSLLTECGCSCLCEV | 556 |
| 801 | MSLLTECGMSCLTEV | 554 |
| 802 | SLGTEVETPIRNEWGCRCNDSSD | 542 |
| 803 | SLLSEVETPIRNEWGCRCNDSSD | 532 |
| 804 | SLWTEVETPIRNEWGCRCNDSSD | 525 |
| 805 | MSLLTCVGMSLLTEC | 524 |
| 806 | SLCTEVGCLLTEV | 522 |
| 807 | CLLTEVGCSLLTEV | 520 |
| 808 | SCLTEVGCSLLTEC | 514 |
| 809 | CSLLTECGCLLTEV | 507 |
| 810 | SLLTCVGCSLLTEV | 504 |
| 811 | CSLLTECGCLCTCV | 458 |
| 812 | SLLTCVGCSLLTEC | 447 |
| 813 | CSLLTECGSLLTEC | 441 |
| 814 | CSLLTECGSLLCEV | 430 |
| 815 | CSLLTECGSCLCEC | 419 |
| 816 | CLLTEVGCSLLTEC | 409 |
| 817 | CSLLTECGCSCLCEV | 404 |
| 818 | MSLLTECGCSLLTEC | 386 |
| 819 | CLCTCVGCSLLTEC | 340 |
| 820 | MSLLTCVGCSLLTEC | 330 |
| 821 | CSCLCEVGCSLLTEV | 325 |
| 822 | SLLTDVETPIRNEWGCRCNDSSD | 324 |
| 823 | SCLTEVGSLLTEC | 321 |
| 824 | SLLTCVGSLLTEV | 320 |
| 825 | MSLLCEVGMSLLTEC | 314 |
| 826 | MSLLCEVGCSLLTEC | 312 |
| 827 | MSCLCECGCSLLTEV | 306 |
| 828 | MCLCTCVGMSLLTEC | 306 |
| 829 | MSLLTEVGMSCLCEC | 304 |

TABLE 2-continued

Peptides that specifically bind for 23K21 and 8I10 (A numeral "1" in the peptide sequence indicates a differentially protected cystein allowing for selective CLIP attachment at certain residues)

| SEQ ID NO: | Peptides that bind to 23K21 and 8I10 | Signal |
|---|---|---|
| 830 | 1CSLLTEVETP1SLLTEVETPCLLTEVETPI1 | 2303 |
| 831 | 1CSLLTEVETP1SLLTEVETPCSLLTEVETP1 | 2147 |
| 832 | 1CLTEVETPIR1SLLTEVETPCLLTEVETPI1 | 2145 |
| 833 | SLLTEVETCSLLTEVETATPIRNEWGCRC | 2133 |
| 834 | SLLTEVET1CSLLTEVET1SLLTEVETCEWG1R | 2107 |
| 835 | SLLTEVET1CSLLTEVET1SLLTEVETAWGCR1 | 2103 |
| 836 | 1CLTEVETPIR1SLLTEVETPCSLLTEVETP1 | 1936 |
| 837 | 1CETPIRNEWG1SLLTEVETPCLLTEVETPI1 | 1912 |
| 838 | 1CTEVETPIRN1SLLTEVETPCLLTEVETPI1 | 1887 |
| 839 | 1CTEVETPIRN1SLLTEVETPCSLLTEVETP1 | 1796 |
| 840 | SLLTEVET1CSLLTEVET1SLLTEVETCEWGSR1 | 1765 |
| 841 | 1CSLLTEVETP1LTEVETPIRCSLLTEVETP1 | 1732 |
| 842 | 1CSLLTEVETP1TEVETPIRNCSLLTEVETP1 | 1717 |
| 843 | 1CVETPIRNEW1SLLTEVETPCLTEVETPIR1 | 1715 |
| 844 | SLLTEVET1CSLLTEVET1SLLTEVETAGCR1N | 1712 |
| 845 | 1CSLLTEVETP1SLLTEVETPCETPIRNEWG1 | 1704 |
| 846 | SLLTEVETCSLLTEVETCNEWGSRSNDSSC | 1697 |
| 847 | 1CLLTEVETPI1SLLTEVETPCLLTEVETPI1 | 1665 |
| 848 | 1CEVETPIRNE1SLLTEVETPCSLLTEVETP1 | 1655 |
| 849 | 1CLLTEVETPI1LTEVETPIRCSLLTEVETP1 | 1651 |
| 850 | 1CSLLTEVETP1SLLTEVETPCVETPIRNEW1 | 1649 |
| 851 | 1CSLLTEVETP1VETPIRNEWCSLLTEVETP1 | 1634 |
| 852 | SLLTEVET1CSLLTEVET1SLLTEVETCIRNEW1 | 1598 |
| 853 | SLLTEVET1CSLLTEVET1SLLTEVETCLLTEV1 | 1592 |
| 854 | 1CTEVETPIRN1LTEVETPIRCSLLTEVETP1 | 1590 |
| 855 | 1CEVETPIRNE1SLLTEVETPCLLTEVETPI1 | 1584 |
| 856 | SLLTEVETCSLLTEVETCVETPIRNEWGC | 1584 |
| 857 | 1CLTEVETPIR1SLLTEVETPCLTEVETPIR1 | 1576 |
| 858 | 1CETPIRNEWG1SLLTEVETPCSLLTEVETP1 | 1559 |
| 859 | 1CSLLTEVETP1SLLTEVETPCLTEVETPIR1 | 1552 |
| 860 | 1CVETPIRNEW1SLLTEVETPCSLLTEVETP1 | 1531 |
| 861 | SLLTEVET1CSLLTEVET1SLLTEVETCSLLTE1 | 1490 |
| 862 | SLLTEVET1CSLLTEVET1SLLTEVETCTPIRN1 | 1481 |
| 863 | 1CLTEVETPIR1LTEVETPIRCSLLTEVETP1 | 1458 |
| 864 | 1CTEVETPIRN1SLLTEVETPCLTEVETPIR1 | 1452 |
| 865 | SLLTEVETCSLLTEVETAEWGCRCNDSSD | 1451 |
| 866 | 1CVETPIRNEW1SLLTEVETPCETPIRNEWG1 | 1446 |
| 867 | 1CLLTEVETPI1SLLTEVETPCSLLTEVETP1 | 1438 |
| 868 | 1CEVETPIRNE1SLLTEVETPCETPIRNEWG1 | 1425 |
| 869 | 1CSLLTEVETP1EVETPIRNECSLLTEVETP1 | 1405 |
| 870 | 1CEVETPIRNE1EVETPIRNECSLLTEVETP1 | 1400 |
| 871 | 1CVETPIRNEW1SLLTEVETPCLLTEVETPI1 | 1396 |
| 872 | 1CEVETPIRNE1LTEVETPIRCSLLTEVETP1 | 1382 |
| 873 | 1CSLLTEVETP1VETPIRNEWCLLTEVETPI1 | 1382 |
| 874 | SLLTEVETCSLLTEVETCEWGSRSNDSSDC | 1375 |
| 875 | SLLTEVETCSLLTEVETCSLLTEVETPIRC | 1369 |
| 876 | 1CVETPIRNEW1LTEVETPIRCSLLTEVETP1 | 1327 |
| 877 | 1CVETPIRNEW1ETPIRNEWGCSLLTEVETP1 | 1317 |
| 878 | 1CSLLTEVETP1TEVETPIRNCLLTEVETPI1 | 1313 |
| 879 | SLLTEVETCSLLTEVETCETPIRNEWGCR | 1306 |
| 880 | 1CLTEVETPIR1TEVETPIRNCSLLTEVETP1 | 1290 |
| 881 | CSLLTEVETPIRNEWGCETPIRNEWGSRSNDSC | 1289 |
| 882 | 1CETPIRNEWG1LTEVETPIRCSLLTEVETP1 | 1286 |
| 883 | 1CLLTEVETPI1TEVETPIRNCSLLTEVETP1 | 1270 |
| 884 | SLLTEVETCSLLTEVETCRNEWGSRSNDSC | 1255 |
| 885 | 1CSLLTEVETP1ETPIRNEWGCSLLTEVETP1 | 1250 |
| 886 | 1CSLLTEVETP1LTEVETPIRCLTEVETPIR1 | 1241 |
| 887 | 1CTEVETPIRN1TEVETPIRNCSLLTEVETP1 | 1229 |
| 888 | CSLLTEVETCPIRNEWGSRSNDSSDC | 1224 |
| 889 | 1CSLLTEVETP1EVETPIRNECLLTEVETPI1 | 1221 |
| 890 | SLLTEVET1CSLLTEVET1SLLTEVETCETPIR1 | 1208 |
| 891 | CSLLTEVETPIRNCETPIRNEWGSRSNDSC | 1204 |
| 892 | 1CSLLTEVETP1LLTEVETPICLTEVETPIR1 | 1203 |
| 893 | SLLTEVET1CSLLTEVET1SLLTEVETCVETPI1 | 1200 |
| 894 | CSLLTEVETCTPIRNEWGSRSNDSSC | 1196 |
| 895 | SLLTEVET1CSLLTEVET1SLLTEVETCRNEWG1 | 1195 |
| 896 | 1CETPIRNEWG1ETPIRNEWGCSLLTEVETP1 | 1180 |
| 897 | 1CEVETPIRNE1SLLTEVETPCLTEVETPIR1 | 1169 |
| 898 | SLLTEVET1CSLLTEVET1SLLTEVETACR1ND | 1169 |
| 899 | SLLTEVETCSLLTEVETAPIRNEWGCRCN | 1165 |
| 900 | 1CSLLTEVETP1LLTEVETPICSLLTEVETP1 | 1157 |

TABLE 2-continued

Peptides that specifically bind for 23K21 and 8I10 (A numeral "1" in the peptide sequence indicates a differentially protected cystein allowing for selective CLIP attachment at certain residues)

| SEQ ID NO: | Peptides that bind to 23K21 and 8I10 | Signal |
|---|---|---|
| 901 | SLLTEVET1CSLLTEVET1SLLTEVETCLTEVE1 | 1144 |
| 902 | 1CLTEVETPIR1ETPIRNEWGCSLLTEVETP1 | 1125 |
| 903 | 1CEVETPIRNE1ETPIRNEWGCSLLTEVETP1 | 1124 |
| 904 | SLLTEVETCSLLTEVETAIRNEWGCRCND | 1120 |
| 905 | CSLLTEVETPICETPIRNEWGSRSNDSC | 1120 |
| 906 | CSLLTEVETPIRNEWGCPIRNEWGSRSNDSSDC | 1118 |
| 907 | SLLTEVET1CSLLTEVET1SLLTEVETCPIRNE1 | 1104 |
| 908 | SLLTEVET1CSLLTEVET1SLLTEVETCNEWG1 | 1103 |
| 909 | SLLTEVETCSLLTEVETCLLTEVETPIRNC | 1101 |
| 910 | 1CETPIRNEWG1SLLTEVETPCLTEVETPIR1 | 1099 |
| 911 | CSLLTEVETPIRCETPIRNEWGSRSNDSC | 1087 |
| 912 | SLLTEVETCSLLTEVETCTPIRNEWGSRSC | 1081 |
| 913 | 1CTEVETPIRN1SLLTEVETPCEVETPIRNE1 | 1079 |
| 914 | SLLTEVET1CSLLTEVET1SLLTEVETCEVETP1 | 1062 |
| 915 | SLLTEVET1CSLLTEVET1SLLTEVETCTEVET1 | 1053 |
| 916 | 1CSLLTEVETP1LTEVETPIRCLLTEVETPI1 | 1048 |
| 917 | CSLLTEVETPIRNECETPIRNEWGSRSNDSC | 1037 |
| 918 | 1CSLLTEVETP1SLLTEVETPCTEVETPIRN1 | 1022 |
| 919 | 1CETPIRNEWG1TEVETPIRNCSLLTEVETP1 | 1021 |
| 920 | CSLLTEVETPIRNECTPIRNEWGSRSNDSSC | 1019 |
| 921 | 1CEVETPIRNE1TEVETPIRNCSLLTEVETP1 | 1014 |
| 922 | CSLLTEVETPCETPIRNEWGSRSNDSC | 1010 |
| 923 | 1CSLLTEVETP1LLTEVETPICLLTEVETPI1 | 1009 |
| 924 | CSLLTEVETPIRCTPIRNEWGSRSNDSSC | 1000 |
| 925 | SLLTEVETCSLLTEVETCVETPIRNEWGSC | 979 |
| 926 | SLLTEVETCSLLTEVETARNEWGCRCNDS | 963 |
| 927 | SLLTEVETCSLLTEVETCETPIRNEWGSRC | 935 |
| 928 | SLLTEVETCSLLTEVETANEWGCRCNDSS | 897 |
| 929 | 1CETPIRNEWG1VETPIRNEWCSLLTEVETP1 | 890 |
| 930 | SLLTEVETCSLLTEVETCEVETPIRNEWGC | 867 |
| 931 | CSLLTEVETPCPIRNEWGSRSNDSSDC | 853 |
| 932 | 1CLTEVETPIR1VETPIRNEWCSLLTEVETP1 | 852 |
| 933 | SLLTEVETCSLLTEVETCPIRNEWGSRSNC | 840 |
| 934 | 1CEVETPIRNE1VETPIRNEWCSLLTEVETP1 | 834 |
| 935 | 1CVETPIRNEW1SLLTEVETPCVETPIRNEW1 | 815 |
| 936 | 1CETPIRNEWG1EVETPIRNECSLLTEVETP1 | 809 |
| 937 | 1CSLLTEVETP1ETPIRNEWGCLLTEVETPI1 | 805 |
| 938 | CSLLTEVETCETPIRNEWGSRSNDSC | 796 |
| 939 | 1CSLLTEVETP1LLTEVETPICETPIRNEWG1 | 777 |
| 940 | SLLTEVETCSLLTEVETCTEVETPIRNEWC | 775 |
| 941 | 1CEVETPIRNE1SLLTEVETPCTEVETPIRN1 | 772 |
| 942 | 1CETPIRNEWG1SLLTEVETPCTEVETPIRN1 | 749 |
| 943 | 1CLLTEVETPI1VETPIRNEWCSLLTEVETP1 | 743 |
| 944 | 1CSLLTEVETP1TEVETPIRNCLTEVETPIR1 | 740 |
| 945 | 1CLTEVETPIR1SLLTEVETPCVETPIRNEW1 | 733 |
| 946 | 1CLTEVETPIR1SLLTEVETPCTEVETPIRN1 | 729 |
| 947 | 1CVETPIRNEW1SLLTEVETPCTEVETPIRN1 | 724 |
| 948 | SLLTEVETCSLLTEVETCIRNEWGSRSNDC | 721 |
| 949 | 1CLLTEVETPI1SLLTEVETPCLTEVETPIR1 | 717 |
| 950 | 1CETPIRNEWG1SLLTEVETPCVETPIRNEW1 | 715 |
| 951 | 1CTEVETPIRN1SLLTEVETPCVETPIRNEW1 | 711 |
| 952 | 1CTEVETPIRN1VETPIRNEWCSLLTEVETP1 | 710 |
| 953 | 1CVETPIRNEW1TEVETPIRNCSLLTEVETP1 | 708 |
| 954 | CSLLTEVETPICPIRNEWGSRSNDSSDC | 700 |
| 955 | 1CVETPIRNEW1VETPIRNEWCSLLTEVETP1 | 699 |
| 956 | 1CTEVETPIRN1SLLTEVETPCETPIRNEWG1 | 691 |
| 957 | 1CTEVETPIRN1SLLTEVETPCTEVETPIRN1 | 684 |
| 958 | 1CSLLTEVETP1SLLTEVETPCEVETPIRNE1 | 684 |
| 959 | 1CEVETPIRNE1SLLTEVETPCVETPIRNEW1 | 674 |
| 960 | SLLTEVETCSLLTEVETCLTEVETPIRNEC | 666 |
| 961 | 1CLTEVETPIR1EVETPIRNECSLLTEVETP1 | 665 |
| 962 | 1CLTEVETPIR1SLLTEVETPCETPIRNEWG1 | 657 |
| 963 | 1CVETPIRNEW1EVETPIRNECSLLTEVETP1 | 652 |
| 964 | 1CETPIRNEWG1SLLTEVETPCETPIRNEWG1 | 645 |
| 965 | CSLLTEVETPCTPIRNEWGSRSNDSSC | 645 |
| 966 | CSLLTEVETPICTPIRNEWGSRSNDSSC | 622 |
| 967 | 1CLLTEVETPI1EVETPIRNECSLLTEVETP1 | 617 |
| 968 | 1CLLTEVETPI1ETPIRNEWGCSLLTEVETP1 | 608 |
| 969 | CSLLTEVETPIRCPIRNEWGSRSNDSSDC | 606 |
| 970 | CSLLTEVETPIRNCPIRNEWGSRSNDSSDC | 589 |
| 971 | 1CSLLTEVETP1LTEVETPIRCTEVETPIRN1 | 571 |

TABLE 2-continued

Peptides that specifically bind for 23K21 and 8I10 (A numeral "1" in the peptide sequence indicates a differentially protected cystein allowing for selective CLIP attachment at certain residues)

| SEQ ID NO: | Peptides that bind to 23K21 and 8I10 | Signal |
|---|---|---|
| 972 | 1CSLLTEVETP1LTEVETPIRCETPIRNEWG1 | 564 |
| 973 | CSLLTEVETPIRNECPIRNEWGSRSNDSSDC | 553 |
| 974 | 1CSLLTEVETP1LLTEVETPICVETPIRNEW1 | 551 |
| 975 | 1CLLTEVETPI1SLLTEVETPCVETPIRNEW1 | 539 |
| 976 | 1CLTEVETPIR1SLLTEVETPCEVETPIRNE1 | 538 |
| 977 | 1CVETPIRNEW1LLTEVETPICSLLTEVETP1 | 537 |
| 978 | 1CTEVETPIRN1EVETPIRNECSLLTEVETP1 | 535 |
| 979 | CSLLTEVETPIRNCTPIRNEWGSRSNDSSC | 532 |
| 980 | CSLLTEVETPIRNEWGCTPIRNEWGSRSNDSSC | 508 |
| 981 | 1CSLLTEVETP1TEVETPIRNCTEVETPIRN1 | 505 |
| 982 | 1CTEVETPIRN1ETPIRNEWGCSLLTEVETP1 | 504 |
| 983 | SLLTEVET1CSLLTEVET1SLLTEVETCNEWGS1 | 346 |
| 984 | CSLLTEVETPIRNC | 2154 |
| 985 | SLLTEVCTCIRNEWG | 2047 |
| 986 | SLLTEVETCSLLTEVETPIRNEWGSRC | 1883 |
| 987 | SLLTEVCTPICNEWG | 1857 |
| 988 | SLLTEVCTPIRCEWG | 1853 |
| 989 | SLLTEVECPIRCEWG | 1849 |
| 990 | CSLLTEVCTPIRNE | 1721 |
| 991 | SLLTEVETCIRNEWGC | 1707 |
| 992 | SLLTEVETCIRNCWG | 1691 |
| 993 | SLLTEVETCCRNEWG | 1675 |
| 994 | SLLTEVETPIRCCWG | 1674 |
| 995 | SLLTEVETSLLTEVETPIRNEWGCRCND | 1663 |
| 996 | SLLTEVCTPCRNEWG | 1551 |
| 997 | CSLLTEVETPIRCE | 1512 |
| 998 | SLLTEVETCIRCEWG | 1495 |
| 999 | SLLTEVETCSLLTEVETPIRNEWGSRSC | 1488 |
| 1000 | SLLTEVCTPIRNCWG | 1440 |
| 1001 | SLLTEVECPIRNCWG | 1438 |
| 1002 | SLCTEVETCIRNEWG | 1385 |
| 1003 | SLLTECETCIRNEWG | 1384 |
| 1004 | SLLTEVECCIRNEWG | 1377 |
| 1005 | SLLTEVETPCRNCWG | 1377 |
| 1006 | SLLTEVETCICNEWG | 1360 |
| 1007 | SLLTEVECPIRNC | 1341 |
| 1008 | SLLTECETPIRNCWG | 1298 |
| 1009 | SLLTEVETCIRNEWG | 1286 |
| 1010 | SLLTEVETPICNCWG | 1255 |
| 1011 | SLLTEVETCSLLTEVETPIRNEWGSRSNC | 1239 |
| 1012 | CSLLTEVETPICNE | 1232 |
| 1013 | CSLLTEVETCIRNE | 1220 |
| 1014 | SLLTEVCCPIRNEWG | 1195 |
| 1015 | SLLTEVETPIRNCWGC | 1177 |
| 1016 | SLLTEVCTPIRNC | 1163 |
| 1017 | SLLTEVECPIRNEWC | 1161 |
| 1018 | CSLLTEVETPIRNE | 1159 |
| 1019 | SLLTEVCTPIRNEWG | 1156 |
| 1020 | CSLLTEVETPCRNE | 1148 |
| 1021 | SLLTEVETPIRCEWGC | 1135 |
| 1022 | SLLTEVETCIRNC | 1134 |
| 1023 | SLLTEVETPIRCECG | 1121 |
| 1024 | CSLLTEVECPIRNE | 1116 |
| 1025 | SLLTEVECPCRNEWG | 1110 |
| 1026 | SCLTEVETPCRNEWG | 1083 |
| 1027 | CSLLTECETPIRNE | 1082 |
| 1028 | SLLTEVECPICNEWG | 1079 |
| 1029 | SLLTECETPIRCEWG | 1052 |
| 1030 | SLLTEVETCIRNEWC | 1049 |
| 1031 | SLCTEVETPIRNC | 1035 |
| 1032 | SLLTEVETCSLLTEVETPIRNEWGCR | 1032 |
| 1033 | SLLTECECPIRNEWG | 1031 |
| 1034 | SLLTEVETPICCEWG | 1029 |
| 1035 | SLLTEVECPIRCE | 1027 |
| 1036 | SLLTEVETPIRNCWG | 1021 |
| 1037 | SCLTEVCTPIRNE | 1019 |
| 1038 | SCLTEVETCIRNEWG | 1015 |
| 1039 | SLLTEVETPIRNCWC | 1002 |
| 1040 | SLLTEVETCSLLTEVETPIRC | 995 |
| 1041 | SLLTEVECPIRNEWG | 980 |
| 1042 | SLLTEVETSLLTEVETPIRNEWGCRC | 979 |

TABLE 2-continued

Peptides that specifically bind for 23K21 and 8I10 (A numeral "1" in the peptide sequence indicates a differentially protected cystein allowing for selective CLIP attachment at certain residues)

| SEQ ID NO: | Peptides that bind to 23K21 and 8I10 | Signal |
|---|---|---|
| 1043 | SLLTEVETSLLTEVETPIRNEWGCRCN | 970 |
| 1044 | SLLTEVCTCIRNE | 949 |
| 1045 | SLCTEVETPIRCE | 945 |
| 1046 | SLLTEVETCIRNECG | 941 |
| 1047 | SCLTEVETPIRNC | 940 |
| 1048 | SLLTEVETCSLLTEVETPIRNEWGC | 938 |
| 1049 | SLLTEVCTPIRNEWC | 937 |
| 1050 | SLLTEVECPIRNE | 927 |
| 1051 | SLLTEVETPICNEWGC | 923 |
| 1052 | SLLTEVETCSLLTEVETPIRNEWGSRSNDSSC | 916 |
| 1053 | SLLTEVETPIRCEWG | 902 |
| 1054 | SLCTEVETPIRNCWG | 899 |
| 1055 | SLLTEVETCIRCE | 898 |
| 1056 | SLLTECETPCRNEWG | 897 |
| 1057 | SLLTEVETPICNEWG | 890 |
| 1058 | SLLTEVETCSLLTEVETPIRNC | 890 |
| 1059 | SLLTECETPICNEWG | 885 |
| 1060 | SLLTECETPIRNEWG | 880 |
| 1061 | SLLTEVETPCRCEWG | 875 |
| 1062 | SLLTEVETCSLLTEVETPIRNEWGSRSNDC | 874 |
| 1063 | SLLTECCTPIRNEWG | 866 |
| 1064 | SLLTEVETCSLLTEVETPIRNEWGSRSNDSC | 861 |
| 1065 | SLLTEVCTPCRNE | 853 |
| 1066 | SCLTECETPIRNEWG | 847 |
| 1067 | SLLTEVETCSLLTEVETPC | 844 |
| 995 | SLLTEVETSLLTEVETPIRNEWGCRCNDS | 836 |
| 1068 | SLLTEVETCSLLTEVETPIRNEWGSRSNDSSDC | 831 |
| 1069 | SLLTEVETCSLLTEVETPIC | 830 |
| 1070 | SLLTEVETCSLLTEVETC | 820 |
| 1071 | SLLTEVETPCRNEWG | 813 |
| 1072 | CSLLTEVETPIRNEWGC | 798 |
| 1073 | SLLTEVCTPIRCE | 789 |
| 1074 | SLLTECETCIRNE | 785 |
| 1075 | SCLTECETPIRNE | 780 |
| 1076 | SLLTEVETCSLLTEVETPIRNEWC | 768 |
| 1077 | SLLTEVETPCCNEWG | 766 |
| 1078 | SLCTEVECPIRNEWG | 750 |
| 1079 | SLCTEVETPIRCEWG | 750 |
| 1080 | SLLTECETPIRNEWC | 741 |
| 1081 | SLLTEVCTPIRNEWGC | 739 |
| 1082 | SLLTEVETPIRCEWC | 732 |
| 1083 | SCLTEVETCIRNE | 727 |
| 1084 | SLLTEVETCICNE | 727 |
| 1085 | SLLTEVETPICNEWC | 724 |
| 1086 | SLLTEVECPIRNEWGC | 715 |
| 1087 | SLCTEVETCIRNE | 712 |
| 1088 | SLLTEVETCSLLTEVETPIRNEWGSC | 712 |
| 1089 | SLLTEVETSLLTEVETPIRNEWGCRCNDSS | 711 |
| 1090 | SCLTEVECPIRNE | 705 |
| 1091 | SLLTEVCTPICNE | 699 |
| 1092 | SLLTEVETPCRNEWGC | 696 |
| 1093 | SLLTEVETCIRNE | 675 |
| 1094 | SLLTEVCTPIRNECG | 674 |
| 1095 | SLLTEVETSLLTEVETPIRNEWGCRCNDSSD | 669 |
| 1096 | SLLTEVETPICNC | 665 |
| 1097 | SCLTEVETPIRNCWG | 662 |
| 1098 | SLLTEVETPICNECG | 660 |
| 1099 | SLLTEVECPIRNECG | 656 |
| 1100 | SLCTEVCTPIRNE | 653 |
| 1101 | SLLTECETPIRCE | 648 |
| 1102 | SLCTECETPIRNEWG | 648 |
| 1103 | SLCTEVECPIRNE | 645 |
| 1104 | SLLTECETPIRNC | 643 |
| 1105 | SLCTEVCTPIRNEWG | 641 |
| 1106 | SLLTEVETPIRNCCG | 638 |
| 1107 | SLLTEVETCSLLTEVETPIRNEC | 629 |
| 1108 | SLLTECETPIRNEWGC | 607 |
| 1109 | SLCTEVETPCRNEWG | 607 |
| 1110 | SLLTEVETPCRNEWC | 589 |
| 1111 | SLLTEVETPCRNECG | 587 |
| 1112 | SLLTEVECPICNE | 582 |

TABLE 2-continued

Peptides that specifically bind for 23K21 and 8I10 (A numeral "1" in the peptide sequence indicates a differentially protected cystein allowing for selective CLIP attachment at certain residues)

| SEQ ID NO: | Peptides that bind to 23K21 and 8I10 | Signal |
|---|---|---|
| 1113 | SLLTECETPIRNE | 578 |
| 1114 | SLCTEVETPICNEWG | 578 |
| 1115 | SLLTEVETPCRNC | 571 |
| 1116 | SLLTEVCTPIRNE | 568 |
| 1117 | SLLTEVETPIRNEWC | 558 |
| 1118 | SCLTEVECPIRNEWG | 542 |
| 1119 | SLLTEVECPCRNE | 538 |
| 1120 | SLCTEVETPCRNE | 535 |
| 1121 | SLCTEVETPIRNEWC | 535 |
| 1122 | SLLTECETPICNE | 531 |
| 1123 | SLLTECETPIRNECG | 528 |
| 1124 | SLCTEVETPIRNEWG | 510 |
| 1125 | SLLTECECPIRNE | 507 |
| 1126 | CMSLLTEVETPIRNC | 1864 |
| 1127 | MSLLTEVEKPIRNEWGCRCN | 1854 |
| 1128 | MSLLTEVETPCRNC | 1834 |
| 1129 | MSLLTEVECPIRNC | 1752 |
| 1130 | MSLLTEVCTPIRNC | 1738 |
| 1131 | DSLLTEVETPIRNEWGCRCN | 1713 |
| 1132 | MSLLTEVETPIRNEAGCRCN | 1700 |
| 1133 | MSLLTEVETPCRCE | 1651 |
| 1134 | MSLLTEVETPCRNE | 1638 |
| 1135 | MSLLTEVEMPIRNEWGCRCN | 1580 |
| 1136 | MSLLTEVEAPIRNEWGCRCN | 1544 |
| 1137 | MSLLTEVELPIRNEWGCRCN | 1521 |
| 1138 | MSLLTELETPIRNEWGCRCN | 1497 |
| 1139 | MSLLTEVETPIRNAWGCRCN | 1480 |
| 1140 | MSLTTEVETPIRNEWGCRCN | 1474 |
| 1141 | MTLLTEVETPIRNEWGCRCN | 1470 |
| 1142 | MSLLTEVETPICNC | 1451 |
| 1143 | MSLLTEVCTPIRCE | 1428 |
| 1144 | MSLLTEVETAIRNEWGCRCN | 1398 |
| 1145 | MSLCTEVETPIRNC | 1395 |
| 1146 | MSLLTEVETCIRNE | 1387 |
| 1147 | MSLLTEVETCICNE | 1378 |
| 1148 | MSLLTEVEEPIRNEWGCRCN | 1361 |
| 1149 | MSLLTEVETPIRNEWGCRCN | 1360 |
| 1150 | MSLLTEVEQPIRNEWGCRCN | 1345 |
| 1151 | MSLLTEVECPIRCE | 1336 |
| 1152 | MSLLTEKETPIRNEWGCRCN | 1324 |
| 1153 | ESLLTEVETPIRNEWGCRCN | 1310 |
| 1154 | MSLCTEVETCIRNE | 1305 |
| 1155 | MSLLTETETPIRNEWGCRCN | 1279 |
| 1156 | MSLLTEIETPIRNEWGCRCN | 1255 |
| 1157 | MSLLTEVETPIRNEWGCRAN | 1252 |
| 1158 | MSLLTEVCTPCRNE | 1244 |
| 1159 | TSLLTEVETPIRNEWGCRCN | 1243 |
| 1160 | MSLCTEVCTPIRNE | 1243 |
| 1161 | MSLLTEVETPIRNEWGCRCA | 1233 |
| 1162 | MSLVTEVETPIRNEWGCRCN | 1202 |
| 1163 | MSCLTEVETPIRCE | 1192 |
| 1164 | MSLATEVETPIRNEWGCRCN | 1188 |
| 1165 | MSLLTEVVTPIRNEWGCRCN | 1183 |
| 1166 | MSLLTEVQTPIRNEWGCRCN | 1172 |
| 1167 | MSLITEVETPIRNEWGCRCN | 1167 |
| 1168 | MSLLTEVECPIRNE | 1158 |
| 1169 | MSLLTEVCTPICNE | 1157 |
| 1170 | MSLLTEPETPIRNEWGCRCN | 1153 |
| 1171 | MSLLTEVEFPIRNEWGCRCN | 1149 |
| 1172 | MSLLTEVETPARNEWGCRCN | 1149 |
| 1173 | MSLLTEVETPIRNEWGARCN | 1149 |
| 1174 | MSLLTEVMTPIRNEWGCRCN | 1133 |
| 1175 | MSLLTECETPIRCE | 1131 |
| 1176 | CMSLLTEVECPIRNE | 1122 |
| 1177 | ASLLTEVETPIRNEWGCRCN | 1111 |
| 1178 | MSLLTEVETCIRCE | 1105 |
| 1179 | MSCLTEVETPIRNC | 1102 |
| 1180 | MSLLTEVEGPIRNEWGCRCN | 1099 |
| 1181 | MSLLTEVETPIRNEWACRCN | 1087 |
| 1182 | MSLLTEMETPIRNEWGCRCN | 1075 |
| 1183 | KSLLTEVETPIRNEWGCRCN | 1068 |

TABLE 2-continued

Peptides that specifically bind for 23K21 and 8I10 (A numeral "1" in the peptide sequence indicates a differentially protected cystein allowing for selective CLIP attachment at certain residues)

| SEQ ID NO: | Peptides that bind to 23K21 and 8I10 | Signal |
|---|---|---|
| 1184 | MSLLTEVEVPIRNEWGCRCN | 1064 |
| 1185 | MSLCTEVETPCRNE | 1064 |
| 1186 | MSCLTEVCTPIRNE | 1055 |
| 1187 | CMSLLTEVCTPIRNE | 1054 |
| 1188 | VSLLTEVETPIRNEWGCRCN | 1054 |
| 1189 | MSLLTEVESPIRNEWGCRCN | 1051 |
| 1190 | MSLLTEVSTPIRNEWGCRCN | 1045 |
| 1191 | MSLLTEFETPIRNEWGCRCN | 1044 |
| 1192 | CMSLLTEVETPIRCE | 1034 |
| 1193 | MSLCTEVECPIRNE | 1023 |
| 1194 | MSLLTECETPICNE | 1016 |
| 1195 | MSLLTEVTTPIRNEWGCRCN | 1013 |
| 1196 | RSLLTEVETPIRNEWGCRCN | 1012 |
| 1197 | MSLLTEVEDPIRNEWGCRCN | 1004 |
| 1198 | MSLLTEAETPIRNEWGCRCN | 1003 |
| 1199 | CMSLLTEVETPCRNE | 992 |
| 1200 | MSLLTEVETPIRAEWGCRCN | 978 |
| 1201 | MSLLTEVCTCIRNE | 959 |
| 1202 | MSLLTECECPIRNE | 958 |
| 1203 | HSLLTEVETPIRNEWGCRCN | 956 |
| 1204 | CMSLLTECETPIRNE | 937 |
| 1205 | MSLLTEVENPIRNEWGCRCN | 936 |
| 1206 | MSLLTECETPCRNE | 932 |
| 1207 | MSLLTEVERPIRNEWGCRCN | 926 |
| 1208 | MSLLTEQETPIRNEWGCRCN | 913 |
| 1209 | MSLLTEVETCIRNC | 908 |
| 1210 | MSFLTEVETPIRNEWGCRCN | 907 |
| 1211 | CMSLLTEVETCIRNE | 896 |
| 1212 | PSLLTEVETPIRNEWGCRCN | 841 |
| 1213 | MSLETEVETPIRNEWGCRCN | 838 |
| 1214 | MSLLTEVEHPIRNEWGCRCN | 838 |
| 1215 | YSLLTEVETPIRNEWGCRCN | 835 |
| 1216 | MSLLTEVCTPIRNE | 824 |
| 1217 | MSLLTEVECPICNE | 821 |
| 1218 | MSLLTEVETPIANEWGCRCN | 814 |
| 1219 | LSLLTEVETPIRNEWGCRCN | 801 |
| 1220 | WSLLTEVETPIRNEWGCRCN | 742 |
| 1221 | MSLLTEVETPIRNEWGCACN | 739 |
| 1222 | MSLLTEVECPCRNE | 736 |
| 1223 | MSCLTEVECPIRNE | 730 |
| 1224 | FSLLTEVETPIRNEWGCRCN | 707 |
| 1225 | NSLLTEVETPIRNEWGCRCN | 706 |
| 1226 | MSLLTEVEYPIRNEWGCRCN | 685 |
| 1227 | MSLLTDVETPIRNEWGCRCN | 679 |
| 1228 | MSKLTEVETPIRNEWGCRCN | 672 |
| 1229 | MSCLTEVETCIRNE | 649 |
| 1230 | MSLSTEVETPIRNEWGCRCN | 648 |
| 1231 | MSLLTECETPIRNE | 630 |
| 1232 | ISLLTEVETPIRNEWGCRCN | 629 |
| 1233 | MSCLTEVETPCRNE | 625 |
| 1234 | MSLCTEVETPIRNE | 618 |
| 1235 | CMSLLTEVETPICNE | 615 |
| 1236 | MSLLTEVEPPIRNEWGCRCN | 610 |
| 1237 | MSCLTEVETPIRNE | 602 |
| 1238 | GSLLTEVETPIRNEWGCRCN | 584 |
| 1239 | MSLCTEVETPIRCE | 568 |
| 1240 | MSLKTEVETPIRNEWGCRCN | 567 |
| 1241 | MSLLTEEETPIRNEWGCRCN | 545 |
| 1242 | CSLCTEVETPIRNE | 518 |
| 1243 | QSLLTEVETPIRNEWGCRCN | 440 |
| 1244 | MSLLTEVEIPIRNEWGCRCN | 409 |
| 1245 | MSLLTESETPIRNEWGCRCN | 369 |
| 1246 | MSLLTEGETPIRNEWGCRCN | 357 |
| 1247 | MSLLTECETPIRNC | 344 |
| 1248 | MSLLTECETCIRNE | 312 |
| 1249 | SSLLTEVETPIRNEWGCRCN | 303 |

TABLE 3

Peptides that show specific binding to Z3G1 (A numeral "1" in the peptide sequence indicates a differentially protected cystein allowing for selective CLIP attachment at certain residues)

| SEQ ID NO: | Peptides that bind to Z3G1 | Signal |
| --- | --- | --- |
| 1177 | ASLLTEVETPIRNEWGCRCN | 2816 |
| 1131 | DSLLTEVETPIRNEWGCRCN | 2814 |
| 1153 | ESLLTEVETPIRNEWGCRCN | 2816 |
| 1224 | FSLLTEVETPIRNEWGCRCN | 2665 |
| 1238 | GSLLTEVETPIRNEWGCRCN | 2635 |
| 1203 | HSLLTEVETPIRNEWGCRCN | 2490 |
| 1232 | ISLLTEVETPIRNEWGCRCN | 2438 |
| 1183 | KSLLTEVETPIRNEWGCRCN | 2618 |
| 1219 | LSLLTEVETPIRNEWGCRCN | 2506 |
| 1149 | MSLLTEVETPIRNEWGCRCN | 2711 |
| 1225 | NSLLTEVETPIRNEWGCRCN | 2485 |
| 1212 | PSLLTEVETPIRNEWGCRCN | 2694 |
| 1243 | QSLLTEVETPIRNEWGCRCN | 2619 |
| 1196 | RSLLTEVETPIRNEWGCRCN | 2550 |
| 1249 | SSLLTEVETPIRNEWGCRCN | 2404 |
| 1159 | TSLLTEVETPIRNEWGCRCN | 2834 |
| 1188 | VSLLTEVETPIRNEWGCRCN | 2816 |
| 1220 | WSLLTEVETPIRNEWGCRCN | 2693 |
| 1215 | YSLLTEVETPIRNEWGCRCN | 2650 |
| 1250 | MALLTEVETPIRNEWGCRCN | 2604 |
| 1251 | MDLLTEVETPIRNEWGCRCN | 2726 |
| 1252 | MELLTEVETPIRNEWGCRCN | 2679 |
| 1253 | MFLLTEVETPIRNEWGCRCN | 1707 |
| 1254 | MGLLTEVETPIRNEWGCRCN | 2635 |
| 1255 | MHLLTEVETPIRNEWGCRCN | 2449 |
| 1256 | MILLTEVETPIRNEWGCRCN | 1634 |
| 1257 | MKLLTEVETPIRNEWGCRCN | 2629 |
| 1258 | MLLLTEVETPIRNEWGCRCN | 2091 |
| 1259 | MMLLTEVETPIRNEWGCRCN | 2666 |
| 1260 | MNLLTEVETPIRNEWGCRCN | 2733 |
| 1261 | MPLLTEVETPIRNEWGCRCN | 2521 |
| 1262 | MQLLTEVETPIRNEWGCRCN | 2526 |
| 1263 | MRLLTEVETPIRNEWGCRCN | 2519 |
| 1141 | MTLLTEVETPIRNEWGCRCN | 2809 |
| 1264 | MVLLTEVETPIRNEWGCRCN | 2465 |
| 1265 | MWLLTEVETPIRNEWGCRCN | 2615 |
| 1266 | MYLLTEVETPIRNEWGCRCN | 1960 |
| 1210 | MSFLTEVETPIRNEWGCRCN | 1087 |
| 1267 | MSILTEVETPIRNEWGCRCN | 2582 |
| 1268 | MSMLTEVETPIRNEWGCRCN | 1329 |
| 1269 | MSVLTEVETPIRNEWGCRCN | 2111 |
| 1164 | MSLATEVETPIRNEWGCRCN | 2747 |
| 1270 | MSLDTEVETPIRNEWGCRCN | 2594 |
| 1213 | MSLETEVETPIRNEWGCRCN | 2768 |
| 1271 | MSLFTEVETPIRNEWGCRCN | 2115 |
| 1272 | MSLHTEVETPIRNEWGCRCN | 2058 |
| 1167 | MSLITEVETPIRNEWGCRCN | 2684 |
| 1240 | MSLKTEVETPIRNEWGCRCN | 2691 |
| 1273 | MSLMTEVETPIRNEWGCRCN | 2804 |
| 1274 | MSLNTEVETPIRNEWGCRCN | 2787 |
| 1275 | MSLPTEVETPIRNEWGCRCN | 2007 |
| 1276 | MSLQTEVETPIRNEWGCRCN | 2792 |
| 1277 | MSLRTEVETPIRNEWGCRCN | 2554 |
| 1230 | MSLSTEVETPIRNEWGCRCN | 2768 |
| 1140 | MSLTTEVETPIRNEWGCRCN | 2742 |
| 1162 | MSLVTEVETPIRNEWGCRCN | 2776 |
| 1278 | MSLYTEVETPIRNEWGCRCN | 1313 |
| 1279 | MSLLAEVETPIRNEWGCRCN | 2807 |
| 1280 | MSLLDEVETPIRNEWGCRCN | 2763 |
| 1281 | MSLLEEVETPIRNEWGCRCN | 2805 |
| 1282 | MSLLFEVETPIRNEWGCRCN | 2581 |
| 1283 | MSLLGEVETPIRNEWGCRCN | 2717 |
| 1284 | MSLLHEVETPIRNEWGCRCN | 2691 |
| 1285 | MSLLIEVETPIRNEWGCRCN | 2371 |
| 1286 | MSLLKEVETPIRNEWGCRCN | 2825 |
| 1287 | MSLLLEVETPIRNEWGCRCN | 2804 |
| 1288 | MSLLMEVETPIRNEWGCRCN | 2847 |
| 1289 | MSLLNEVETPIRNEWGCRCN | 2824 |
| 1290 | MSLLPEVETPIRNEWGCRCN | 2728 |
| 1291 | MSLLQEVETPIRNEWGCRCN | 2792 |
| 1292 | MSLLREVETPIRNEWGCRCN | 2699 |

TABLE 3-continued

Peptides that show specific binding to Z3G1 (A numeral "1" in the peptide sequence indicates a differentially protected cystein allowing for selective CLIP attachment at certain residues)

| SEQ ID NO: | Peptides that bind to Z3G1 | Signal |
|---|---|---|
| 1293 | MSLLSEVETPIRNEWGCRCN | 2790 |
| 1294 | MSLLVEVETPIRNEWGCRCN | 2732 |
| 1295 | MSLLWEVETPIRNEWGCRCN | 2531 |
| 1296 | MSLLYEVETPIRNEWGCRCN | 2464 |
| 1227 | MSLLTDVETPIRNEWGCRCN | 2476 |
| 1297 | MSLLTQVETPIRNEWGCRCN | 1697 |
| 1298 | MSLLTTVETPIRNEWGCRCN | 2699 |
| 1156 | MSLLTEIETPIRNEWGCRCN | 2799 |
| 1138 | MSLLTELETPIRNEWGCRCN | 2589 |
| 1155 | MSLLTETETPIRNEWGCRCN | 2641 |
| 1299 | MSLLTEVATPIRNEWGCRCN | 2633 |
| 1300 | MSLLTEVDTPIRNEWGCRCN | 2856 |
| 1301 | MSLLTEVFTPIRNEWGCRCN | 1858 |
| 1302 | MSLLTEVGTPIRNEWGCRCN | 2789 |
| 1303 | MSLLTEVHTPIRNEWGCRCN | 2751 |
| 1304 | MSLLTEVITPIRNEWGCRCN | 2668 |
| 1305 | MSLLTEVKTPIRNEWGCRCN | 2708 |
| 1306 | MSLLTEVLTPIRNEWGCRCN | 2714 |
| 1174 | MSLLTEVMTPIRNEWGCRCN | 2813 |
| 1307 | MSLLTEVNTPIRNEWGCRCN | 2807 |
| 1308 | MSLLTEVPTPIRNEWGCRCN | 2380 |
| 1166 | MSLLTEVQTPIRNEWGCRCN | 2813 |
| 1309 | MSLLTEVRTPIRNEWGCRCN | 2668 |
| 1190 | MSLLTEVSTPIRNEWGCRCN | 2783 |
| 1195 | MSLLTEVTTPIRNEWGCRCN | 2791 |
| 1165 | MSLLTEVVTPIRNEWGCRCN | 2732 |
| 1310 | MSLLTEVWTPIRNEWGCRCN | 2546 |
| 1311 | MSLLTEVYTPIRNEWGCRCN | 2181 |
| 1136 | MSLLTEVEAPIRNEWGCRCN | 2833 |
| 1197 | MSLLTEVEDPIRNEWGCRCN | 2826 |
| 1148 | MSLLTEVEEPIRNEWGCRCN | 2835 |
| 1171 | MSLLTEVFPIRNEWGCRCN | 2728 |
| 1180 | MSLLTEVEGPIRNEWGCRCN | 2802 |
| 1214 | MSLLTEVEHPIRNEWGCRCN | 2753 |
| 1244 | MSLLTEVEIPIRNEWGCRCN | 2742 |
| 1127 | MSLLTEVEKPIRNEWGCRCN | 2837 |
| 1137 | MSLLTEVELPIRNEWGCRCN | 2797 |
| 1135 | MSLLTEVEMPIRNEWGCRCN | 2839 |
| 1205 | MSLLTEVENPIRNEWGCRCN | 2805 |
| 1236 | MSLLTEVEPPIRNEWGCRCN | 2797 |
| 1150 | MSLLTEVEQPIRNEWGCRCN | 2826 |
| 1207 | MSLLTEVERPIRNEWGCRCN | 2753 |
| 1189 | MSLLTEVESPIRNEWGCRCN | 2712 |
| 1184 | MSLLTEVEVPIRNEWGCRCN | 2768 |
| 1312 | MSLLTEVEWPIRNEWGCRCN | 2541 |
| 1226 | MSLLTEVEYPIRNEWGCRCN | 2571 |
| 1144 | MSLLTEVETAIRNEWGCRCN | 2722 |
| 1172 | MSLLTEVETPARNEWGCRCN | 2774 |
| 1218 | MSLLTEVETPIANEWGCRCN | 2683 |
| 1200 | MSLLTEVETPIRAEWGCRCN | 2742 |
| 1139 | MSLLTEVETPIRNAWGCRCN | 2803 |
| 1132 | MSLLTEVETPIRNEAGCRCN | 2831 |
| 1181 | MSLLTEVETPIRNEWACRCN | 2732 |
| 1173 | MSLLTEVETPIRNEWGARCN | 2760 |
| 1221 | MSLLTEVETPIRNEWGCACN | 2662 |
| 1157 | MSLLTEVETPIRNEWGCRAN | 2769 |
| 1161 | MSLLTEVETPIRNEWGCRCA | 2770 |
| 1126 | CMSLLTEVETPIRNC | 2767 |
| 1192 | CMSLLTEVETPIRCE | 2453 |
| 1235 | CMSLLTEVETPICNE | 2331 |
| 1199 | CMSLLTEVETPCRNE | 2789 |
| 1211 | CMSLLTEVETCIRNE | 2713 |
| 1176 | CMSLLTEVECPIRNE | 2730 |
| 1187 | CMSLLTEVCTPIRNE | 2633 |
| 1313 | CMSLLCEVETPIRNE | 2582 |
| 1314 | CMSLCTEVETPIRNE | 1705 |
| 1315 | CMCLLTEVETPIRNE | 2347 |
| 984 | CSLLTEVETPIRNC | 2782 |
| 997 | CSLLTEVETPIRCE | 2516 |
| 1012 | CSLLTEVETPICNE | 2444 |
| 1020 | CSLLTEVETPCRNE | 2470 |

TABLE 3-continued

Peptides that show specific binding to Z3G1 (A numeral "1" in the peptide sequence indicates a differentially protected cystein allowing for selective CLIP attachment at certain residues)

| SEQ ID NO: | Peptides that bind to Z3G1 | Signal |
|---|---|---|
| 1013 | CSLLTEVETCIRNE | 2301 |
| 1024 | CSLLTEVECPIRNE | 2226 |
| 990 | CSLLTEVCTPIRNE | 1942 |
| 1316 | CSLLCEVETPIRNE | 2527 |
| 1242 | CSLCTEVETPIRNE | 1832 |
| 1317 | MCLLTEVETPIRNC | 2743 |
| 1318 | MCLLTEVETPIRCE | 2307 |
| 1319 | MCLLTEVETPICNE | 2379 |
| 1320 | MCLLTEVETPCRNE | 2404 |
| 1321 | MCLLTEVETCIRNE | 1948 |
| 1322 | MCLLTEVECPIRNE | 2421 |
| 1323 | MCLLTEVCTPIRNE | 1407 |
| 1324 | MCLLCEVETPIRNE | 2038 |
| 1145 | MSLCTEVETPIRNC | 2601 |
| 1239 | MSLCTEVETPIRCE | 1555 |
| 1185 | MSLCTEVETPCRNE | 1673 |
| 1193 | MSLCTEVECPIRNE | 1538 |
| 1160 | MSLCTEVCTPIRNE | 1906 |
| 1325 | MSLLCEVETPIRNC | 2823 |
| 1326 | MSLLCEVETPIRCE | 2772 |
| 1327 | MSLLCEVETPICNE | 2704 |
| 1328 | MSLLCEVETPCRNE | 2652 |
| 1329 | MSLLCEVETCIRNE | 2589 |
| 1330 | MSLLCEVECPIRNE | 2606 |
| 1331 | MSLLCEVCTPIRNE | 2601 |
| 1130 | MSLLTEVCTPIRNC | 2787 |
| 1143 | MSLLTEVCTPIRCE | 2667 |
| 1169 | MSLLTEVCTPICNE | 2526 |
| 1158 | MSLLTEVCTPCRNE | 2572 |
| 1201 | MSLLTEVCTCIRNE | 2143 |
| 1168 | MSLLTEVECPIRNE | 2613 |
| 1129 | MSLLTEVECPIRNC | 2755 |
| 1151 | MSLLTEVECPIRCE | 2675 |
| 1217 | MSLLTEVECPICNE | 2440 |
| 1222 | MSLLTEVECPCRNE | 2361 |
| 1146 | MSLLTEVETCIRNE | 2129 |
| 1209 | MSLLTEVETCIRNC | 2309 |
| 1178 | MSLLTEVETCIRCE | 2739 |
| 1147 | MSLLTEVETCICNE | 2721 |
| 1134 | MSLLTEVETPCRNE | 2695 |
| 1128 | MSLLTEVETPCRNC | 2810 |
| 1133 | MSLLTEVETPCRCE | 2597 |
| 1142 | MSLLTEVETPICNC | 2758 |
| 1018 | CSLLTEVETPIRNE | 2211 |
| 1332 | MCLLTEVETPIRNE | 2364 |
| 1234 | MSLCTEVETPIRNE | 2054 |
| 1333 | MSLLCEVETPIRNE | 2454 |
| 1216 | MSLLTEVCTPIRNE | 2529 |
| 287 | MSLLTEVGMSLLTEV | 2878 |
| 293 | CSLLTEVGMSLLTEV | 2827 |
| 513 | MCLLTEVGMSLLTEV | 2697 |
| 532 | MSCLTEVGMSLLTEV | 2336 |
| 371 | MSLCTEVGMSLLTEV | 2691 |
| 749 | MSLLCEVGMSLLTEV | 2786 |
| 543 | MSLLTCVGMSLLTEV | 2627 |
| 339 | MSLLTECGMSLLTEV | 2170 |
| 288 | CSCLCEVGMSLLTEV | 1812 |
| 663 | MCLCTCVGMSLLTEV | 2509 |
| 294 | MSCLCECGMSLLTEV | 1006 |
| 373 | CSLLTECGMSLLTEV | 1235 |
| 316 | MSLLTEVGCSLLTEV | 2650 |
| 364 | CSLLTEVGCSLLTEV | 2503 |
| 570 | MCLLTEVGCSLLTEV | 2717 |
| 557 | MSCLTEVGCSLLTEV | 2506 |
| 508 | MSLCTEVGCSLLTEV | 2832 |
| 781 | MSLLCEVGCSLLTEV | 2761 |
| 528 | MSLLTCVGCSLLTEV | 2467 |
| 363 | MSLLTECGCSLLTEV | 1235 |
| 536 | MCLCTCVGCSLLTEV | 2241 |
| 360 | CSLLTECGCSLLTEV | 1427 |
| 296 | MSLLTEVGMCLLTEV | 2809 |

TABLE 3-continued

Peptides that show specific binding to Z3G1 (A numeral "1" in the peptide sequence indicates a differentially protected cystein allowing for selective CLIP attachment at certain residues)

| SEQ ID NO: | Peptides that bind to Z3G1 | Signal |
|---|---|---|
| 303 | CSLLTEVGMCLLTEV | 2618 |
| 1334 | MSLLCEVGMCLLTEV | 2676 |
| 359 | MSLLTEVGMSCLTEV | 2793 |
| 372 | CSLLTEVGMSCLTEV | 2554 |
| 1335 | MCLLTEVGMSCLTEV | 1869 |
| 1336 | MSLLCEVGMSCLTEV | 2846 |
| 317 | MSLLTEVGMSLCTEV | 2895 |
| 334 | CSLLTEVGMSLCTEV | 2857 |
| 1337 | MCLLTEVGMSLCTEV | 2513 |
| 289 | MSLCTEVGMSLCTEV | 1093 |
| 1338 | MSLLCEVGMSLCTEV | 2595 |
| 793 | MSLLTEVGMSLLCEV | 2819 |
| 309 | CSLLTEVGMSLLCEV | 2734 |
| 1339 | MCLLTEVGMSLLCEV | 2234 |
| 1340 | MSCLTEVGMSLLCEV | 2341 |
| 304 | MSLCTEVGMSLLCEV | 2616 |
| 1341 | MSLLCEVGMSLLCEV | 2851 |
| 1342 | MSLLTCVGMSLLCEV | 2712 |
| 460 | MSLLTECGMSLLCEV | 2373 |
| 1343 | CSCLCEVGMSLLCEV | 1945 |
| 1344 | MCLCTCVGMSLLCEV | 2431 |
| 1345 | MSCLCECGMSLLCEV | 1307 |
| 456 | CSLLTECGMSLLCEV | 1640 |
| 285 | MSLLTEVGMSLLTCV | 2872 |
| 286 | CSLLTEVGMSLLTCV | 2768 |
| 1346 | MCLLTEVGMSLLTCV | 1098 |
| 542 | MSLCTEVGMSLLTCV | 2722 |
| 1347 | MSLLCEVGMSLLTCV | 2784 |
| 343 | MSLLTEVGMSLLTEC | 2831 |
| 451 | CSLLTEVGMSLLTEC | 2613 |
| 825 | MSLLCEVGMSLLTEC | 2617 |
| 761 | MSLLTEVGCSCLCEV | 2053 |
| 476 | CSLLTEVGCSCLCEV | 1680 |
| 1348 | MSLCTEVGCSCLCEV | 2001 |
| 1349 | MSLLCEVGCSCLCEV | 2586 |
| 291 | MSLLTEVGMCLCTCV | 2842 |
| 297 | CSLLTEVGMCLCTCV | 2649 |
| 1350 | MSLLCEVGMCLCTCV | 2664 |
| 829 | MSLLTEVGMSCLCEC | 2444 |
| 499 | CSLLTEVGMSCLCEC | 2101 |
| 1351 | MSLLCEVGMSCLCEC | 2492 |
| 470 | MSLLTEVGCSLLTEC | 2349 |
| 383 | CSLLTEVGCSLLTEC | 2486 |
| 592 | MSLCTEVGCSLLTEC | 1971 |
| 826 | MSLLCEVGCSLLTEC | 2573 |
| 365 | CSLLTEVCMSLLTEC | 1891 |
| 1352 | CCLLTEVETPIRNE | 2155 |
| 1353 | CLLTEVETPIRNC | 1996 |
| 1354 | CLLTEVETPIRCE | 1813 |
| 1355 | CLLTEVETPICNE | 1647 |
| 1356 | CLLTEVETPCRNE | 1991 |
| 1357 | CLLTEVETCIRNE | 1661 |
| 1358 | CLLTEVECPIRNE | 2326 |
| 1359 | CLLTEVCTPIRNE | 1585 |
| 1360 | CLLCEVETPIRNE | 2314 |
| 1100 | SLCTEVCTPIRNE | 1674 |
| 1361 | SLLCEVETPIRNC | 2460 |
| 1362 | SLLCEVETPIRCE | 2307 |
| 1363 | SLLCEVETPICNE | 1921 |
| 1364 | SLLCEVETPCRNE | 2035 |
| 1365 | SLLCEVETCIRNE | 2305 |
| 1366 | SLLCEVECPIRNE | 2377 |
| 1367 | SLLCEVCTPIRNE | 2283 |
| 1016 | SLLTEVCTPIRNC | 2308 |
| 1073 | SLLTEVCTPIRCE | 1873 |
| 1091 | SLLTEVCTPICNE | 1659 |
| 1065 | SLLTEVCTPCRNE | 2016 |
| 1044 | SLLTEVCTCIRNE | 1695 |
| 1050 | SLLTEVCPIRNE | 2469 |
| 1007 | SLLTEVECPIRNC | 2635 |
| 1035 | SLLTEVECPIRCE | 2426 |

TABLE 3-continued

Peptides that show specific binding to Z3G1 (A numeral "1" in the peptide sequence indicates a differentially protected cystein allowing for selective CLIP attachment at certain residues)

| SEQ ID NO: | Peptides that bind to Z3G1 | Signal |
|---|---|---|
| 1112 | SLLTEVECPICNE | 2022 |
| 1119 | SLLTEVECPCRNE | 1840 |
| 1093 | SLLTEVETCIRNE | 1792 |
| 1022 | SLLTEVETCIRNC | 2289 |
| 1055 | SLLTEVETCIRCE | 2161 |
| 1084 | SLLTEVETCICNE | 1953 |
| 1368 | SLLTEVETPCRNE | 1665 |
| 1115 | SLLTEVETPCRNC | 1816 |
| 1369 | SLLTEVETPCRCE | 1546 |
| 1096 | SLLTEVETPICNC | 2075 |
| 1370 | CLLTEVETPIRNE | 1524 |
| 1371 | SLLCEVETPIRNE | 2511 |
| 1116 | SLLTEVCTPIRNE | 1854 |
| 1072 | CSLLTEVETPIRNEWGC | 2232 |
| 1372 | CLLTEVETPIRNEWGC | 1866 |
| 1373 | SLLCEVETPIRNEWGC | 2281 |
| 1081 | SLLTEVCTPIRNEWGC | 1866 |
| 1086 | SLLTEVECPIRNEWGC | 2142 |
| 991 | SLLTEVETCIRNEWGC | 2284 |
| 1092 | SLLTEVETPCRNEWGC | 1873 |
| 1051 | SLLTEVETPICNEWGC | 2101 |
| 1021 | SLLTEVETPIRCEWGC | 2435 |
| 1015 | SLLTEVETPIRNCWGC | 2513 |
| 1374 | SLLTEVETPIRNECGC | 1660 |
| 1375 | SLLTEVETPIRNEWCC | 1813 |
| 1376 | CLLTEVETPIRNEWC | 1743 |
| 1377 | CLLTEVETPIRNECG | 1501 |
| 1378 | CLLTEVETPIRNCWG | 2388 |
| 1379 | CLLTEVETPIRCEWG | 2169 |
| 1380 | CLLTEVETPICNEWG | 2120 |
| 1381 | CLLTEVETPCRNEWG | 2074 |
| 1382 | CLLTEVETCIRNEWG | 2296 |
| 1383 | CLLTEVECPIRNEWG | 2157 |
| 1384 | CLLCEVETPIRNEWG | 2388 |
| 1385 | CLLTEVETPIRNEWG | 2142 |
| 1105 | SLCTEVCTPIRNEWG | 1477 |
| 1386 | SLCCEVETPIRNEWG | 1603 |
| 1387 | SLLCEVETPIRNEWC | 2406 |
| 1388 | SLLCEVETPIRNECG | 2107 |
| 1389 | SLLCEVETPIRNCWG | 2789 |
| 1390 | SLLCEVETPIRCEWG | 2601 |
| 1391 | SLLCEVETPICNEWG | 2536 |
| 1392 | SLLCEVETPCRNEWG | 2465 |
| 1393 | SLLCEVETCIRNEWG | 2531 |
| 1394 | SLLCEVECPIRNEWG | 2529 |
| 1395 | SLLCEVCTPIRNEWG | 2384 |
| 1396 | SLLCEVETPIRNEWG | 2384 |
| 1049 | SLLTEVCTPIRNEWC | 1883 |
| 1094 | SLLTEVCTPIRNECG | 1782 |
| 1000 | SLLTEVCTPIRNCWG | 2420 |
| 988 | SLLTEVCTPIRCEWG | 2090 |
| 987 | SLLTEVCTPICNEWG | 1883 |
| 996 | SLLTEVCTPCRNEWG | 1841 |
| 985 | SLLTEVCTCIRNEWG | 1546 |
| 1014 | SLLTEVCCPIRNEWG | 2253 |
| 1019 | SLLTEVCTPIRNEWG | 2692 |
| 1397 | CLLTEVCTPIRNEWG | 1634 |
| 1017 | SLLTEVECPIRNEWC | 2141 |
| 1099 | SLLTEVECPIRNECG | 2001 |
| 1001 | SLLTEVECPIRNCWG | 2589 |
| 989 | SLLTEVECPIRCEWG | 2509 |
| 1028 | SLLTEVECPICNEWG | 2449 |
| 1025 | SLLTEVECPCRNEWG | 2303 |
| 1004 | SLLTEVECCIRNEWG | 2507 |
| 1041 | SLLTEVECPIRNEWG | 2267 |
| 1030 | SLLTEVETCIRNEWC | 2337 |
| 1046 | SLLTEVETCIRNECG | 2018 |
| 992 | SLLTEVETCIRNCWG | 2616 |
| 998 | SLLTEVETCIRCEWG | 2566 |
| 1006 | SLLTEVETCICNEWG | 2498 |
| 993 | SLLTEVETCCRNEWG | 2389 |

TABLE 3-continued

Peptides that show specific binding to Z3G1 (A numeral "1" in the peptide sequence indicates a differentially protected cystein allowing for selective CLIP attachment at certain residues)

| SEQ ID NO: | Peptides that bind to Z3G1 | Signal |
|---|---|---|
| 1009 | SLLTEVETCIRNEWG | 2462 |
| 1110 | SLLTEVETPCRNEWC | 1867 |
| 1111 | SLLTEVETPCRNECG | 1470 |
| 1005 | SLLTEVETPCRNCWG | 2602 |
| 1061 | SLLTEVETPCRCEWG | 2155 |
| 1077 | SLLTEVETPCCNEWG | 2208 |
| 1071 | SLLTEVETPCRNEWG | 2167 |
| 1085 | SLLTEVETPICNEWC | 2488 |
| 1098 | SLLTEVETPICNECG | 2041 |
| 1010 | SLLTEVETPICNCWG | 2624 |
| 1034 | SLLTEVETPICCEWG | 2525 |
| 1057 | SLLTEVETPICNEWG | 2395 |
| 1082 | SLLTEVETPIRCEWC | 2255 |
| 1023 | SLLTEVETPIRCECG | 2464 |
| 994 | SLLTEVETPIRCCWG | 2755 |
| 1053 | SLLTEVETPIRCEWG | 2365 |
| 1039 | SLLTEVETPIRNCWC | 2321 |
| 1106 | SLLTEVETPIRNCCG | 1923 |
| 1036 | SLLTEVETPIRNCWG | 2350 |
| 1398 | SLLTEVETPIRNECC | 1493 |
| 1399 | SLLTEVETPIRNECG | 1545 |
| 1117 | SLLTEVETPIRNEWC | 1856 |
| 1070 | SLLTEVETCSLLTEVETC | 2104 |
| 1067 | SLLTEVETCSLLTEVETPC | 2082 |
| 1069 | SLLTEVETCSLLTEVETPIC | 2169 |
| 1040 | SLLTEVETCSLLTEVETPIRC | 2402 |
| 1058 | SLLTEVETCSLLTEVETPIRNC | 2295 |
| 1107 | SLLTEVETCSLLTEVETPIRNEC | 2025 |
| 1076 | SLLTEVETCSLLTEVETPIRNEWC | 2169 |
| 1048 | SLLTEVETCSLLTEVETPIRNEWGC | 2010 |
| 1088 | SLLTEVETCSLLTEVETPIRNEWGSC | 2180 |
| 986 | SLLTEVETCSLLTEVETPIRNEWGSRC | 2757 |
| 999 | SLLTEVETCSLLTEVETPIRNEWGSRSC | 2792 |
| 1011 | SLLTEVETCSLLTEVETPIRNEWGSRSNC | 2673 |
| 1062 | SLLTEVETCSLLTEVETPIRNEWGSRSNDC | 2483 |
| 1064 | SLLTEVETCSLLTEVETPIRNEWGSRSNDSC | 2335 |
| 1052 | SLLTEVETCSLLTEVETPIRNEWGSRSNDSSC | 2404 |
| 1068 | SLLTEVETCSLLTEVETPIRNEWGSRSNDSSDC | 2294 |
| 1032 | SLLTEVETCSLLTEVETPIRNEWGCR | 2395 |
| 1042 | SLLTEVETSLLTEVETPIRNEWGCRC | 2324 |
| 1043 | SLLTEVETSLLTEVETPIRNEWGCRCN | 2390 |
| 995 | SLLTEVETSLLTEVETPIRNEWGCRCND | 2393 |
| 995 | SLLTEVETSLLTEVETPIRNEWGCRCNDS | 2260 |
| 1089 | SLLTEVETSLLTEVETPIRNEWGCRCNDSS | 2212 |
| 1095 | SLLTEVETSLLTEVETPIRNEWGCRCNDSSD | 1980 |
| 831 | 1CSLLTEVETP1SLLTEVETPCSLLTEVETP1 | 2714 |
| 867 | 1CLLTEVETPI1SLLTEVETPCSLLTEVETP1 | 2593 |
| 836 | 1CLTEVETPIR1SLLTEVETPCSLLTEVETP1 | 2645 |
| 839 | 1CTEVETPIRN1SLLTEVETPCSLLTEVETP1 | 2420 |
| 848 | 1CEVETPIRNE1SLLTEVETPCSLLTEVETP1 | 2460 |
| 860 | 1CVETPIRNEW1SLLTEVETPCSLLTEVETP1 | 2474 |
| 858 | 1CETPIRNEWG1SLLTEVETPCSLLTEVETP1 | 2566 |
| 900 | 1CSLLTEVETP1LLTEVETPICSLLTEVETP1 | 2437 |
| 1400 | 1CLLTEVETPI1LLTEVETPICSLLTEVETP1 | 2220 |
| 1401 | 1CLTEVETPIR1LLTEVETPICSLLTEVETP1 | 2316 |
| 1402 | 1CTEVETPIRN1LLTEVETPICSLLTEVETP1 | 2258 |
| 1403 | 1CEVETPIRNE1LLTEVETPICSLLTEVETP1 | 2133 |
| 977 | 1CVETPIRNEW1LLTEVETPICSLLTEVETP1 | 1946 |
| 1404 | 1CETPIRNEWG1LLTEVETPICSLLTEVETP1 | 2288 |
| 841 | 1CSLLTEVETP1LTEVETPIRCSLLTEVETP1 | 2521 |
| 849 | 1CLLTEVETPI1LTEVETPIRCSLLTEVETP1 | 2601 |
| 863 | 1CLTEVETPIR1LTEVETPIRCSLLTEVETP1 | 2476 |
| 854 | 1CTEVETPIRN1LTEVETPIRCSLLTEVETP1 | 2469 |
| 872 | 1CEVETPIRNE1LTEVETPIRCSLLTEVETP1 | 2304 |
| 876 | 1CVETPIRNEW1LTEVETPIRCSLLTEVETP1 | 2350 |
| 882 | 1CETPIRNEWG1LTEVETPIRCSLLTEVETP1 | 2282 |
| 842 | 1CSLLTEVETP1TEVETPIRNCSLLTEVETP1 | 2591 |
| 883 | 1CLLTEVETPI1TEVETPIRNCSLLTEVETP1 | 2492 |
| 880 | 1CLTEVETPIR1TEVETPIRNCSLLTEVETP1 | 2396 |
| 887 | 1CTEVETPIRN1TEVETPIRNCSLLTEVETP1 | 2405 |
| 921 | 1CEVETPIRNE1TEVETPIRNCSLLTEVETP1 | 2272 |

TABLE 3-continued

Peptides that show specific binding to Z3G1 (A numeral "1" in the peptide sequence indicates a differentially protected cystein allowing for selective CLIP attachment at certain residues)

| SEQ ID NO: | Peptides that bind to Z3G1 | Signal |
|---|---|---|
| 953 | 1CVETPIRNEW1TEVETPIRNCSLLTEVETP1 | 2118 |
| 919 | 1CETPIRNEWG1TEVETPIRNCSLLTEVETP1 | 2223 |
| 869 | 1CSLLTEVETP1EVETPIRNECSLLTEVETP1 | 2582 |
| 967 | 1CLLTEVETPI1EVETPIRNECSLLTEVETP1 | 2220 |
| 961 | 1CLTEVETPIR1EVETPIRNECSLLTEVETP1 | 2331 |
| 978 | 1CTEVETPIRN1EVETPIRNECSLLTEVETP1 | 2295 |
| 870 | 1CEVETPIRNE1EVETPIRNECSLLTEVETP1 | 2618 |
| 963 | 1CVETPIRNEW1EVETPIRNECSLLTEVETP1 | 2365 |
| 936 | 1CETPIRNEWG1EVETPIRNECSLLTEVETP1 | 2368 |
| 851 | 1CSLLTEVETP1VETPIRNEWCSLLTEVETP1 | 2708 |
| 943 | 1CLLTEVETPI1VETPIRNEWCSLLTEVETP1 | 2422 |
| 932 | 1CLTEVETPIR1VETPIRNEWCSLLTEVETP1 | 2344 |
| 952 | 1CTEVETPIRN1VETPIRNEWCSLLTEVETP1 | 2380 |
| 934 | 1CEVETPIRNE1VETPIRNEWCSLLTEVETP1 | 2448 |
| 955 | 1CVETPIRNEW1VETPIRNEWCSLLTEVETP1 | 2307 |
| 929 | 1CETPIRNEWG1VETPIRNEWCSLLTEVETP1 | 2419 |
| 885 | 1CSLLTEVETP1ETPIRNEWGCSLLTEVETP1 | 2591 |
| 968 | 1CLLTEVETPI1ETPIRNEWGCSLLTEVETP1 | 2377 |
| 902 | 1CLTEVETPIR1ETPIRNEWGCSLLTEVETP1 | 2296 |
| 1405 | 1CTEVETPIRN1ETPIRNEWGCSLLTEVETP1 | 2268 |
| 903 | 1CEVETPIRNE1ETPIRNEWGCSLLTEVETP1 | 2140 |
| 877 | 1CVETPIRNEW1ETPIRNEWGCSLLTEVETP1 | 2349 |
| 896 | 1CETPIRNEWG1ETPIRNEWGCSLLTEVETP1 | 2425 |
| 830 | 1CSLLTEVETP1SLLTEVETPCLLTEVETPI1 | 2786 |
| 847 | 1CLLTEVETPI1SLLTEVETPCLLTEVETPI1 | 2722 |
| 832 | 1CLTEVETPIR1SLLTEVETPCLLTEVETPI1 | 2711 |
| 838 | 1CTEVETPIRN1SLLTEVETPCLLTEVETPI1 | 2616 |
| 855 | 1CEVETPIRNE1SLLTEVETPCLLTEVETPI1 | 2576 |
| 871 | 1CVETPIRNEW1SLLTEVETPCLLTEVETPI1 | 2544 |
| 837 | 1CETPIRNEWG1SLLTEVETPCLLTEVETPI1 | 2653 |
| 923 | 1CSLLTEVETP1LLTEVETPICLLTEVETPI1 | 2534 |
| 1406 | 1CLLTEVETPI1LLTEVETPICLLTEVETPI1 | 2350 |
| 1407 | 1CLTEVETPIR1LLTEVETPICLLTEVETPI1 | 2316 |
| 1408 | 1CTEVETPIRN1LLTEVETPICLLTEVETPI1 | 2446 |
| 1409 | 1CEVETPIRNE1LLTEVETPICLLTEVETPI1 | 2194 |
| 1410 | 1CVETPIRNEW1LLTEVETPICLLTEVETPI1 | 2331 |
| 1411 | 1CETPIRNEWG1LLTEVETPICLLTEVETPI1 | 2405 |
| 916 | 1CSLLTEVETP1LTEVETPIRCLLTEVETPI1 | 2722 |
| 1412 | 1CLLTEVETPI1LTEVETPIRCLLTEVETPI1 | 2436 |
| 1413 | 1CLTEVETPIR1LTEVETPIRCLLTEVETPI1 | 1445 |
| 1414 | 1CTEVETPIRN1LTEVETPIRCLLTEVETPI1 | 1793 |
| 1415 | 1CEVETPIRNE1LTEVETPIRCLLTEVETPI1 | 1407 |
| 1416 | 1CVETPIRNEW1LTEVETPIRCLLTEVETPI1 | 1369 |
| 1417 | 1CETPIRNEWG1LTEVETPIRCLLTEVETPI1 | 1474 |
| 878 | 1CSLLTEVETP1TEVETPIRNCLLTEVETPI1 | 2664 |
| 1418 | 1CLLTEVETPI1TEVETPIRNCLLTEVETPI1 | 2371 |
| 1419 | 1CLTEVETPIR1TEVETPIRNCLLTEVETPI1 | 1907 |
| 1420 | 1CTEVETPIRN1TEVETPIRNCLLTEVETPI1 | 1905 |
| 1421 | 1CEVETPIRNE1TEVETPIRNCLLTEVETPI1 | 1469 |
| 1422 | 1CVETPIRNEW1TEVETPIRNCLLTEVETPI1 | 1452 |
| 1423 | 1CETPIRNEWG1TEVETPIRNCLLTEVETPI1 | 1735 |
| 889 | 1CSLLTEVETP1EVETPIRNECLLTEVETPI1 | 2595 |
| 1424 | 1CLLTEVETPI1EVETPIRNECLLTEVETPI1 | 2331 |
| 1425 | 1CLTEVETPIR1EVETPIRNECLLTEVETPI1 | 1049 |
| 1426 | 1CTEVETPIRN1EVETPIRNECLLTEVETPI1 | 1107 |
| 873 | 1CSLLTEVETP1VETPIRNEWCLLTEVETPI1 | 2767 |
| 1427 | 1CLLTEVETPI1VETPIRNEWCLLTEVETPI1 | 2410 |
| 1428 | 1CLTEVETPIR1VETPIRNEWCLLTEVETPI1 | 1465 |
| 1429 | 1CTEVETPIRN1VETPIRNEWCLLTEVETPI1 | 1559 |
| 1430 | 1CEVETPIRNE1VETPIRNEWCLLTEVETPI1 | 1477 |
| 1431 | 1CVETPIRNEW1VETPIRNEWCLLTEVETPI1 | 1588 |
| 1432 | 1CETPIRNEWG1VETPIRNEWCLLTEVETPI1 | 1453 |
| 937 | 1CSLLTEVETP1ETPIRNEWGCLLTEVETPI1 | 2646 |
| 1433 | 1CLLTEVETPI1ETPIRNEWGCLLTEVETPI1 | 2361 |
| 1434 | 1CLTEVETPIR1ETPIRNEWGCLLTEVETPI1 | 1699 |
| 1435 | 1CTEVETPIRN1ETPIRNEWGCLLTEVETPI1 | 1573 |
| 1436 | 1CEVETPIRNE1ETPIRNEWGCLLTEVETPI1 | 1434 |
| 1437 | 1CVETPIRNEW1ETPIRNEWGCLLTEVETPI1 | 1582 |
| 1438 | 1CETPIRNEWG1ETPIRNEWGCLLTEVETPI1 | 1968 |
| 1439 | 1CSLLTEVETP1SLLTEVETPCLTEVETPIR1 | 2738 |
| 949 | 1CLLTEVETPI1SLLTEVETPCLTEVETPIR1 | 2403 |

TABLE 3-continued

Peptides that show specific binding to Z3G1 (A numeral "1" in the peptide sequence indicates a differentially protected cystein allowing for selective CLIP attachment at certain residues)

| SEQ ID NO: | Peptides that bind to Z3G1 | Signal |
|---|---|---|
| 857 | 1CLTEVETPIR1SLLTEVETPCLTEVETPIR1 | 2755 |
| 1440 | 1CTEVETPIRN1SLLTEVETPCLTEVETPIR1 | 2705 |
| 897 | 1CEVETPIRNE1SLLTEVETPCLTEVETPIR1 | 2565 |
| 843 | 1CVETPIRNEW1SLLTEVETPCLTEVETPIR1 | 2498 |
| 910 | 1CETPIRNEWG1SLLTEVETPCLTEVETPIR1 | 2473 |
| 892 | 1CSLLTEVETP1LLTEVETPICLTEVETPIR1 | 2546 |
| 1441 | 1CLLTEVETPI1LLTEVETPICLTEVETPIR1 | 2288 |
| 1442 | 1CLTEVETPIR1LLTEVETPICLTEVETPIR1 | 2057 |
| 1443 | 1CTEVETPIRN1LLTEVETPICLTEVETPIR1 | 2213 |
| 1444 | 1CEVETPIRNE1LLTEVETPICLTEVETPIR1 | 2000 |
| 1445 | 1CVETPIRNEW1LLTEVETPICLTEVETPIR1 | 2280 |
| 1446 | 1CETPIRNEWG1LLTEVETPICLTEVETPIR1 | 2367 |
| 886 | 1CSLLTEVETP1LTEVETPIRCLTEVETPIR1 | 2623 |
| 1447 | 1CLLTEVETPI1LTEVETPIRCLTEVETPIR1 | 2283 |
| 944 | 1CSLLTEVETP1TEVETPIRNCLTEVETPIR1 | 2646 |
| 1448 | 1CLLTEVETPI1TEVETPIRNCLTEVETPIR1 | 2440 |
| 1449 | 1CSLLTEVETP1EVETPIRNECLTEVETPIR1 | 2404 |
| 1450 | 1CLLTEVETPI1EVETPIRNECLTEVETPIR1 | 2188 |
| 1451 | 1CSLLTEVETP1VETPIRNEWCLTEVETPIR1 | 2549 |
| 1452 | 1CLLTEVETPI1VETPIRNEWCLTEVETPIR1 | 2607 |
| 1453 | 1CSLLTEVETP1ETPIRNEWGCLTEVETPIR1 | 2465 |
| 1454 | 1CLLTEVETPI1ETPIRNEWGCLTEVETPIR1 | 2218 |
| 918 | 1CSLLTEVETP1SLLTEVETPCTEVETPIRN1 | 2618 |
| 1455 | 1CLLTEVETPI1SLLTEVETPCTEVETPIRN1 | 2283 |
| 946 | 1CLTEVETPIR1SLLTEVETPCTEVETPIRN1 | 2434 |
| 957 | 1CTEVETPIRN1SLLTEVETPCTEVETPIRN1 | 2402 |
| 941 | 1CEVETPIRNE1SLLTEVETPCTEVETPIRN1 | 2692 |
| 947 | 1CVETPIRNEW1SLLTEVETPCTEVETPIRN1 | 2733 |
| 942 | 1CETPIRNEWG1SLLTEVETPCTEVETPIRN1 | 2601 |
| 1456 | 1CSLLTEVETP1LLTEVETPICTEVETPIRN1 | 2103 |
| 1457 | 1CLLTEVETPI1LLTEVETPICTEVETPIRN1 | 1884 |
| 1458 | 1CLTEVETPIR1LLTEVETPICTEVETPIRN1 | 1756 |
| 1459 | 1CTEVETPIRN1LLTEVETPICTEVETPIRN1 | 1749 |
| 1460 | 1CEVETPIRNE1LLTEVETPICTEVETPIRN1 | 1620 |
| 1461 | 1CVETPIRNEW1LLTEVETPICTEVETPIRN1 | 1835 |
| 1462 | 1CETPIRNEWG1LLTEVETPICTEVETPIRN1 | 1710 |
| 971 | 1CSLLTEVETP1LTEVETPIRCTEVETPIRN1 | 2360 |
| 1463 | 1CLLTEVETPI1LTEVETPIRCTEVETPIRN1 | 2188 |
| 1464 | 1CSLLTEVETP1TEVETPIRNCTEVETPIRN1 | 2755 |
| 1465 | 1CLLTEVETPI1TEVETPIRNCTEVETPIRN1 | 2488 |
| 1466 | 1CSLLTEVETP1EVETPIRNECTEVETPIRN1 | 2134 |
| 1467 | 1CLLTEVETPI1EVETPIRNECTEVETPIRN1 | 1851 |
| 1468 | 1CSLLTEVETP1VETPIRNEWCTEVETPIRN1 | 2301 |
| 1469 | 1CLLTEVETPI1VETPIRNEWCTEVETPIRN1 | 1713 |
| 1470 | 1CSLLTEVETP1ETPIRNEWGCTEVETPIRN1 | 2331 |
| 1471 | 1CLLTEVETPI1ETPIRNEWGCTEVETPIRN1 | 1983 |
| 958 | 1CSLLTEVETP1SLLTEVETPCEVETPIRNE1 | 2203 |
| 1472 | 1CLLTEVETPI1SLLTEVETPCEVETPIRNE1 | 2057 |
| 976 | 1CLTEVETPIR1SLLTEVETPCEVETPIRNE1 | 2216 |
| 913 | 1CTEVETPIRN1SLLTEVETPCEVETPIRNE1 | 2139 |
| 1473 | 1CEVETPIRNE1SLLTEVETPCEVETPIRNE1 | 2006 |
| 1474 | 1CVETPIRNEW1SLLTEVETPCEVETPIRNE1 | 1986 |
| 1475 | 1CETPIRNEWG1SLLTEVETPCEVETPIRNE1 | 2642 |
| 1476 | 1CSLLTEVETP1LLTEVETPICEVETPIRNE1 | 2472 |
| 1477 | 1CLLTEVETPI1LLTEVETPICEVETPIRNE1 | 2022 |
| 1478 | 1CLTEVETPIR1LLTEVETPICEVETPIRNE1 | 1681 |
| 1479 | 1CTEVETPIRN1LLTEVETPICEVETPIRNE1 | 1627 |
| 1480 | 1CEVETPIRNE1LLTEVETPICEVETPIRNE1 | 1394 |
| 1481 | 1CVETPIRNEW1LLTEVETPICEVETPIRNE1 | 1592 |
| 1482 | 1CETPIRNEWG1LLTEVETPICEVETPIRNE1 | 1648 |
| 1483 | 1CSLLTEVETP1LTEVETPIRCEVETPIRNE1 | 2040 |
| 1484 | 1CLLTEVETPI1LTEVETPIRCEVETPIRNE1 | 1777 |
| 1485 | 1CSLLTEVETP1TEVETPIRNCEVETPIRNE1 | 2036 |
| 1486 | 1CLLTEVETPI1TEVETPIRNCEVETPIRNE1 | 1798 |
| 1487 | 1CSLLTEVETP1EVETPIRNECEVETPIRNE1 | 1917 |
| 1488 | 1CLLTEVETPI1EVETPIRNECEVETPIRNE1 | 1631 |
| 1489 | 1CSLLTEVETP1VETPIRNEWCEVETPIRNE1 | 2359 |
| 1490 | 1CLLTEVETPI1VETPIRNEWCEVETPIRNE1 | 1730 |
| 1491 | 1CSLLTEVETP1ETPIRNEWGCEVETPIRNE1 | 2338 |
| 1492 | 1CLLTEVETPI1ETPIRNEWGCEVETPIRNE1 | 1781 |
| 850 | 1CSLLTEVETP1SLLTEVETPCVETPIRNEW1 | 2491 |

TABLE 3-continued

Peptides that show specific binding to Z3G1 (A numeral "1" in the peptide sequence indicates a differentially protected cystein allowing for selective CLIP attachment at certain residues)

| SEQ ID NO: | Peptides that bind to Z3G1 | Signal |
|---|---|---|
| 975 | 1CLLTEVETPI1SLLTEVETPCVETPIRNEW1 | 2316 |
| 945 | 1CLTEVETPIR1SLLTEVETPCVETPIRNEW1 | 2366 |
| 951 | 1CTEVETPIRN1SLLTEVETPCVETPIRNEW1 | 2460 |
| 959 | 1CEVETPIRNE1SLLTEVETPCVETPIRNEW1 | 2441 |
| 935 | 1CVETPIRNEW1SLLTEVETPCVETPIRNEW1 | 2470 |
| 950 | 1CETPIRNEWG1SLLTEVETPCVETPIRNEW1 | 2465 |
| 974 | 1CSLLTEVETP1LLTEVETPICVETPIRNEW1 | 2285 |
| 1493 | 1CLLTEVETPI1LLTEVETPICVETPIRNEW1 | 2661 |
| 1494 | 1CLTEVETPIR1LLTEVETPICVETPIRNEW1 | 2443 |
| 1495 | 1CTEVETPIRN1LLTEVETPICVETPIRNEW1 | 2088 |
| 1496 | 1CEVETPIRNE1LLTEVETPICVETPIRNEW1 | 1625 |
| 1497 | 1CVETPIRNEW1LLTEVETPICVETPIRNEW1 | 1817 |
| 1498 | 1CETPIRNEWG1LLTEVETPICVETPIRNEW1 | 1817 |
| 1499 | 1CSLLTEVETP1LTEVETPIRCVETPIRNEW1 | 2319 |
| 1500 | 1CLLTEVETPI1LTEVETPIRCVETPIRNEW1 | 2171 |
| 1501 | 1CSLLTEVETP1TEVETPIRNCVETPIRNEW1 | 2497 |
| 1502 | 1CLLTEVETPI1TEVETPIRNCVETPIRNEW1 | 2229 |
| 1503 | 1CSLLTEVETP1EVETPIRNECVETPIRNEW1 | 2469 |
| 1504 | 1CLLTEVETPI1EVETPIRNECVETPIRNEW1 | 2081 |
| 1505 | 1CSLLTEVETP1VETPIRNEWCVETPIRNEW1 | 2398 |
| 1506 | 1CLLTEVETPI1VETPIRNEWCVETPIRNEW1 | 2074 |
| 1507 | 1CSLLTEVETP1ETPIRNEWGCVETPIRNEW1 | 2778 |
| 1508 | 1CLLTEVETPI1ETPIRNEWGCVETPIRNEW1 | 2495 |
| 845 | 1CSLLTEVETP1SLLTEVETPCETPIRNEWG1 | 2417 |
| 1509 | 1CLLTEVETPI1SLLTEVETPCETPIRNEWG1 | 2057 |
| 962 | 1CLTEVETPIR1SLLTEVETPCETPIRNEWG1 | 2230 |
| 956 | 1CTEVETPIRN1SLLTEVETPCETPIRNEWG1 | 2352 |
| 868 | 1CEVETPIRNE1SLLTEVETPCETPIRNEWG1 | 2326 |
| 866 | 1CVETPIRNEW1SLLTEVETPCETPIRNEWG1 | 2328 |
| 964 | 1CETPIRNEWG1SLLTEVETPCETPIRNEWG1 | 2357 |
| 939 | 1CSLLTEVETP1LLTEVETPICETPIRNEWG1 | 2446 |
| 1510 | 1CLLTEVETPI1LLTEVETPICETPIRNEWG1 | 1999 |
| 1511 | 1CLTEVETPIR1LLTEVETPICETPIRNEWG1 | 2175 |
| 1512 | 1CTEVETPIRN1LLTEVETPICETPIRNEWG1 | 2645 |
| 1513 | 1CEVETPIRNE1LLTEVETPICETPIRNEWG1 | 2466 |
| 1514 | 1CVETPIRNEW1LLTEVETPICETPIRNEWG1 | 2575 |
| 1515 | 1CETPIRNEWG1LLTEVETPICETPIRNEWG1 | 2427 |
| 972 | 1CSLLTEVETP1LTEVETPIRCETPIRNEWG1 | 2583 |
| 1516 | 1CLLTEVETPI1LTEVETPIRCETPIRNEWG1 | 2320 |
| 1517 | 1CSLLTEVETP1TEVETPIRNCETPIRNEWG1 | 2299 |
| 1518 | 1CLLTEVETPI1TEVETPIRNCETPIRNEWG1 | 1972 |
| 1519 | 1CSLLTEVETP1EVETPIRNECETPIRNEWG1 | 2692 |
| 1520 | 1CLLTEVETPI1EVETPIRNECETPIRNEWG1 | 2433 |
| 1521 | 1CSLLTEVETP1VETPIRNEWCETPIRNEWG1 | 2569 |
| 1522 | 1CLLTEVETPI1VETPIRNEWCETPIRNEWG1 | 1931 |
| 1523 | 1CSLLTEVETP1ETPIRNEWGCETPIRNEWG1 | 2340 |
| 1524 | 1CLLTEVETPI1ETPIRNEWGCETPIRNEWG1 | 2007 |
| 861 | SLLTEVET1CSLLTEVET1SLLTEVETCSLLTE1 | 2691 |
| 853 | SLLTEVET1CSLLTEVET1SLLTEVETCLLTEV1 | 2690 |
| 901 | SLLTEVET1CSLLTEVET1SLLTEVETCLTEVE1 | 2396 |
| 915 | SLLTEVET1CSLLTEVET1SLLTEVETCTEVET1 | 2218 |
| 914 | SLLTEVET1CSLLTEVET1SLLTEVETCEVETP1 | 2268 |
| 893 | SLLTEVET1CSLLTEVET1SLLTEVETCVETPI1 | 2422 |
| 890 | SLLTEVET1CSLLTEVET1SLLTEVETCETPIR1 | 2507 |
| 862 | SLLTEVET1CSLLTEVET1SLLTEVETCTPIRN1 | 2690 |
| 907 | SLLTEVET1CSLLTEVET1SLLTEVETCPIRNE1 | 2435 |
| 852 | SLLTEVET1CSLLTEVET1SLLTEVETCIRNEW1 | 2663 |
| 895 | SLLTEVET1CSLLTEVET1SLLTEVETCRNEWG1 | 2476 |
| 908 | SLLTEVET1CSLLTEVET1SLLTEVETCNEWG1 | 2461 |
| 834 | SLLTEVET1CSLLTEVET1SLLTEVETCEWG1R | 2855 |
| 835 | SLLTEVET1CSLLTEVET1SLLTEVETAWGCR1 | 2870 |
| 844 | SLLTEVET1CSLLTEVET1SLLTEVETAGCR1N | 2814 |
| 898 | SLLTEVET1CSLLTEVET1SLLTEVETACR1ND | 2686 |
| 908 | SLLTEVET1CSLLTEVET1SLLTEVETCNEWGS1 | 2726 |
| 840 | SLLTEVET1CSLLTEVET1SLLTEVETCEWGSR1 | 2730 |
| 1525 | CLLTEVETPIRNEWGSCVETPIRNEWGSRSNDC | 2278 |
| 938 | CSLLTEVETCETPIRNEWGSRSNDSC | 1916 |
| 922 | CSLLTEVETPCETPIRNEWGSRSNDSC | 2170 |
| 905 | CSLLTEVETPICETPIRNEWGSRSNDSC | 2041 |
| 911 | CSLLTEVETPIRCETPIRNEWGSRSNDSC | 2024 |
| 891 | CSLLTEVETPIRNCETPIRNEWGSRSNDSC | 1931 |

TABLE 3-continued

Peptides that show specific binding to Z3G1 (A numeral "1" in the peptide sequence indicates a differentially protected cystein allowing for selective CLIP attachment at certain residues)

| SEQ ID NO: | Peptides that bind to Z3G1 | Signal |
|---|---|---|
| 917 | CSLLTEVETPIRNECETPIRNEWGSRSNDSC | 1808 |
| 1526 | CSLLTEVETPIRNEWCETPIRNEWGSRSNDSC | 2012 |
| 881 | CSLLTEVETPIRNEWGCETPIRNEWGSRSNDSC | 2501 |
| 1527 | CLLTEVETPIRNEWGSCETPIRNEWGSRSNDSC | 2414 |
| 894 | CSLLTEVETCTPIRNEWGSRSNDSSC | 2068 |
| 965 | CSLLTEVETPCTPIRNEWGSRSNDSSC | 2351 |
| 966 | CSLLTEVETPICTPIRNEWGSRSNDSSC | 2125 |
| 924 | CSLLTEVETPIRCTPIRNEWGSRSNDSSC | 2162 |
| 979 | CSLLTEVETPIRNCTPIRNEWGSRSNDSSC | 1927 |
| 920 | CSLLTEVETPIRNECTPIRNEWGSRSNDSSC | 1988 |
| 1528 | CSLLTEVETPIRNEWCTPIRNEWGSRSNDSSC | 1959 |
| 980 | CSLLTEVETPIRNEWGCTPIRNEWGSRSNDSSC | 2116 |
| 1529 | CLLTEVETPIRNEWGSCTPIRNEWGSRSNDSSC | 2268 |
| 888 | CSLLTEVETCPIRNEWGSRSNDSSDC | 2246 |
| 931 | CSLLTEVETPCPIRNEWGSRSNDSSDC | 2377 |
| 954 | CSLLTEVETPICPIRNEWGSRSNDSSDC | 2267 |
| 969 | CSLLTEVETPIRCPIRNEWGSRSNDSSDC | 2228 |
| 970 | CSLLTEVETPIRNCPIRNEWGSRSNDSSDC | 2089 |
| 973 | CSLLTEVETPIRNECPIRNEWGSRSNDSSDC | 1955 |
| 1530 | CSLLTEVETPIRNEWCPIRNEWGSRSNDSSDC | 1983 |
| 906 | CSLLTEVETPIRNEWGCPIRNEWGSRSNDSSDC | 1954 |
| 1531 | CLLTEVETPIRNEWGSCPIRNEWGSRSNDSSDC | 1420 |
| 875 | SLLTEVETCSLLTEVETCSLLTEVETPIRC | 2643 |
| 909 | SLLTEVETCSLLTEVETCLLTEVETPIRNC | 2618 |
| 960 | SLLTEVETCSLLTEVETCLTEVETPIRNEC | 2157 |
| 940 | SLLTEVETCSLLTEVETCTEVETPIRNEWC | 2302 |
| 930 | SLLTEVETCSLLTEVETCEVETPIRNEWGC | 2300 |
| 925 | SLLTEVETCSLLTEVETCVETPIRNEWGSC | 2347 |
| 927 | SLLTEVETCSLLTEVETCETPIRNEWGSRC | 2311 |
| 912 | SLLTEVETCSLLTEVETCTPIRNEWGSRSC | 2434 |
| 933 | SLLTEVETCSLLTEVETCPIRNEWGSRSNC | 2192 |
| 948 | SLLTEVETCSLLTEVETCIRNEWGSRSNDC | 1961 |
| 884 | SLLTEVETCSLLTEVETCRNEWGSRSNDSC | 2620 |
| 846 | SLLTEVETCSLLTEVETCNEWGSRSNDSSC | 2640 |
| 874 | SLLTEVETCSLLTEVETCEWGSRSNDSSDC | 2509 |
| 856 | SLLTEVETCSLLTEVETCVETPIRNEWGC | 2671 |
| 879 | SLLTEVETCSLLTEVETCETPIRNEWGCR | 2631 |
| 833 | SLLTEVETCSLLTEVETATPIRNEWGCRC | 2640 |
| 899 | SLLTEVETCSLLTEVETAPIRNEWGCRCN | 2576 |
| 904 | SLLTEVETCSLLTEVETAIRNEWGCRCND | 2538 |
| 926 | SLLTEVETCSLLTEVETARNEWGCRCNDS | 2463 |
| 928 | SLLTEVETCSLLTEVETANEWGCRCNDSS | 2358 |
| 865 | SLLTEVETCSLLTEVETAEWGCRCNDSSD | 2254 |
| 1532 | CSLLTEVETPIRNEWGCRCNDSSD | 2284 |
| 1533 | CLLTEVETPIRNEWGCRCNDSSD | 1979 |
| 1534 | SLLCEVETPIRNEWGCRCNDSSD | 2161 |
| 566 | SLLTEVCTPIRNEWGCRCNDSSD | 1210 |
| 718 | SLLTEVECPIRNEWGCRCNDSSD | 1974 |
| 623 | SLLTEVETCIRNEWGCRCNDSSD | 1992 |
| 687 | SLLTEVETPCRNEWGCRCNDSSD | 2050 |
| 725 | SLLTEVETPICNEWGCRCNDSSD | 2005 |
| 587 | SLLTEVETPIRCEWGCRCNDSSD | 1956 |
| 733 | SLLTEVETPIRNCWGCRCNDSSD | 2006 |
| 268 | SLLTEVETPIRNECGCRCNDSSD | 2554 |
| 714 | SLLTEVETPIRNEWCCRCNDSSD | 2388 |
| 127 | CSLLTEVETCSLLTEVETC | 2555 |
| 198 | CSLLTEVETPCSLLTEVETC | 2341 |
| 187 | CSLLTEVETPICSLLTEVETC | 2554 |
| 147 | CSLLTEVETPIRCSLLTEVETC | 2662 |
| 166 | CSLLTEVETPIRNCSLLTEVETC | 2538 |
| 118 | CSLLTEVETPIRNECSLLTEVETC | 2489 |
| 122 | CSLLTEVETPIRNEWCSLLTEVETC | 2454 |
| 200 | CSLLTEVETPIRNEWGCSLLTEVETC | 2371 |
| 254 | CLLTEVETPIRNEWGCSLLTEVETC | 2177 |
| 136 | CLTEVETPIRNEWGSRCSLLTEVETC | 2026 |
| 226 | CTEVETPIRNEWGSRSCSLLTEVETC | 2140 |
| 201 | CEVETPIRNEWGSRSNCSLLTEVETC | 2288 |
| 223 | CVETPIRNEWGSRSNDCSLLTEVETC | 2233 |
| 213 | CETPIRNEWGSRSNDCSLLTEVETC | 1997 |
| 230 | CTPIRNEWGSRSNDSSCSLLTEVETC | 2168 |
| 161 | CPIRNEWGSRSNDSSDCSLLTEVETC | 2759 |

TABLE 3-continued

Peptides that show specific binding to Z3G1 (A numeral "1" in the peptide sequence indicates a differentially protected cystein allowing for selective CLIP attachment at certain residues)

| SEQ ID NO: | Peptides that bind to Z3G1 | Signal |
|---|---|---|
| 142 | CSLLTEVETCSLLTEVETPC | 2716 |
| 156 | CSLLTEVETPCSLLTEVETPC | 2673 |
| 207 | CSLLTEVETPICSLLTEVETPC | 2440 |
| 181 | CSLLTEVETPIRCSLLTEVETPC | 2448 |
| 144 | CSLLTEVETPIRNCSLLTEVETPC | 2673 |
| 164 | CSLLTEVETPIRNECSLLTEVETPC | 2582 |
| 189 | CSLLTEVETPIRNEWCSLLTEVETPC | 2505 |
| 217 | CSLLTEVETPIRNEWGCSLLTEVETPC | 2445 |
| 270 | CLLTEVETPIRNEWGSCSLLTEVETPC | 2307 |
| 228 | CLTEVETPIRNEWGSRCSLLTEVETPC | 2237 |
| 246 | CTEVETPIRNEWGSRSCSLLTEVETPC | 2182 |
| 229 | CEVETPIRNEWGSRSNCSLLTEVETPC | 2290 |
| 242 | CVETPIRNEWGSRSNDCSLLTEVETPC | 2379 |
| 232 | CETPIRNEWGSRSNDSCSLLTEVETPC | 2425 |
| 247 | CTPIRNEWGSRSNDSSCSLLTEVETPC | 2249 |
| 259 | CPIRNEWGSRSNDSSDCSLLTEVETPC | 2441 |
| 128 | CSLLTEVETCSLLTEVETPIC | 2876 |
| 137 | CSLLTEVETPCSLLTEVETPIC | 2815 |
| 245 | CSLLTEVETPICSLLTEVETPIC | 2492 |
| 151 | CSLLTEVETPIRCSLLTEVETPIC | 2561 |
| 139 | CSLLTEVETPIRNCSLLTEVETPIC | 2666 |
| 145 | CSLLTEVETPIRNECSLLTEVETPIC | 2684 |
| 177 | CSLLTEVETPIRNEWCSLLTEVETPIC | 2548 |
| 197 | CSLLTEVETPIRNEWGCSLLTEVETPIC | 2481 |
| 252 | CLLTEVETPIRNEWGSCSLLTEVETPIC | 2333 |
| 191 | CLTEVETPIRNEWGSRCSLLTEVETPIC | 2405 |
| 216 | CTEVETPIRNEWGSRSCSLLTEVETPIC | 2308 |
| 219 | CEVETPIRNEWGSRSNCSLLTEVETPIC | 2363 |
| 132 | CVETPIRNEWGSRSNDCSLLTEVETPIC | 2372 |
| 237 | CETPIRNEWGSRSNDSCSLLTEVETPIC | 2436 |
| 231 | CTPIRNEWGSRSNDSSCSLLTEVETPIC | 2460 |
| 267 | CPIRNEWGSRSNDSSDCSLLTEVETPIC | 2227 |
| 163 | CSLLTEVETCSLLTEVETPIRC | 2531 |
| 124 | CSLLTEVETPCSLLTEVETPIRC | 2839 |
| 203 | CSLLTEVETPICSLLTEVETPIRC | 2628 |
| 121 | CSLLTEVETPIRCSLLTEVETPIRC | 2767 |
| 120 | CSLLTEVETPIRNCSLLTEVETPIRC | 2751 |
| 130 | CSLLTEVETPIRNECSLLTEVETPIRC | 2751 |
| 155 | CSLLTEVETPIRNEWCSLLTEVETPIRC | 2646 |
| 157 | CSLLTEVETPIRNEWGCSLLTEVETPIRC | 2619 |
| 117 | CLLTEVETPIRNEWGSCSLLTEVETPIRC | 2622 |
| 162 | CLTEVETPIRNEWGSRCSLLTEVETPIRC | 2476 |
| 184 | CTEVETPIRNEWGSRSCSLLTEVETPIRC | 2419 |
| 172 | CEVETPIRNEWGSRSNCSLLTEVETPIRC | 2467 |
| 168 | CVETPIRNEWGSRSNDCSLLTEVETPIRC | 2484 |
| 190 | CETPIRNEWGSRSNDSCSLLTEVETPIRC | 2514 |
| 169 | CTPIRNEWGSRSNDSSCSLLTEVETPIRC | 2518 |
| 176 | CPIRNEWGSRSNDSSDCSLLTEVETPIRC | 2586 |
| 134 | CSLLTEVETCSLLTEVETPIRNC | 2633 |
| 153 | CSLLTEVETPCSLLTEVETPIRNC | 2691 |
| 208 | CSLLTEVETPICSLLTEVETPIRNC | 2548 |
| 131 | CSLLTEVETPIRCSLLTEVETPIRNC | 2753 |
| 129 | CSLLTEVETPIRNCSLLTEVETPIRNC | 2748 |
| 133 | CSLLTEVETPIRNECSLLTEVETPIRNC | 2724 |
| 180 | CSLLTEVETPIRNEWCSLLTEVETPIRNC | 2538 |
| 143 | CSLLTEVETPIRNEWGCSLLTEVETPIRNC | 2657 |
| 178 | CLLTEVETPIRNEWGSCSLLTEVETPIRNC | 2574 |
| 119 | CLTEVETPIRNEWGSRCSLLTEVETPIRNC | 2459 |
| 204 | CTEVETPIRNEWGSRSCSLLTEVETPIRNC | 2358 |
| 196 | CEVETPIRNEWGSRSNCSLLTEVETPIRNC | 2429 |
| 194 | CVETPIRNEWGSRSNDCSLLTEVETPIRNC | 2440 |
| 126 | CETPIRNEWGSRSNDSCSLLTEVETPIRNC | 2440 |
| 185 | CTPIRNEWGSRSNDSSCSLLTEVETPIRNC | 2492 |
| 202 | CPIRNEWGSRSNDSSDCSLLTEVETPIRNC | 2500 |
| 171 | CSLLTEVETCSLLTEVETPIRNEC | 2424 |
| 193 | CSLLTEVETPCSLLTEVETPIRNEC | 2387 |
| 1535 | CSLLTEVETPICSLLTEVETPIRNEC | 1851 |
| 165 | CSLLTEVETPIRCSLLTEVETPIRNEC | 2648 |
| 183 | CSLLTEVETPIRNCSLLTEVETPIRNEC | 2580 |
| 220 | CSLLTEVETPIRNECSLLTEVETPIRNEC | 2522 |
| 241 | CSLLTEVETPIRNEWCSLLTEVETPIRNEC | 2349 |

TABLE 3-continued

Peptides that show specific binding to Z3G1 (A numeral "1" in the peptide sequence indicates a differentially protected cystein allowing for selective CLIP attachment at certain residues)

| SEQ ID NO: | Peptides that bind to Z3G1 | Signal |
| --- | --- | --- |
| 206 | CSLLTEVETPIRNEWGCSLLTEVETPIRNEC | 2419 |
| 244 | CLLTEVETPIRNEWGSCSLLTEVETPIRNEC | 2327 |
| 240 | CLTEVETPIRNEWGSRCSLLTEVETPIRNEC | 2221 |
| 261 | CTEVETPIRNEWGSRSCSLLTEVETPIRNEC | 2074 |
| 273 | CEVETPIRNEWGSRSNCSLLTEVETPIRNEC | 2008 |
| 269 | CVETPIRNEWGSRSNDCSLLTEVETPIRNEC | 2140 |
| 154 | CETPIRNEWGSRSNDSCSLLTEVETPIRNEC | 2122 |
| 266 | CTPIRNEWGSRSNDSSCSLLTEVETPIRNEC | 2080 |
| 248 | CPIRNEWGSRSNDSSDCSLLTEVETPIRNEC | 2249 |
| 150 | CSLLTEVETCSLLTEVETPIRNEWC | 2577 |
| 158 | CSLLTEVETPCSLLTEVETPIRNEWC | 2567 |
| 211 | CSLLTEVETPICSLLTEVETPIRNEWC | 2423 |
| 173 | CSLLTEVETPIRCSLLTEVETPIRNEWC | 2566 |
| 135 | CSLLTEVETPIRNCSLLTEVETPIRNEWC | 2820 |
| 146 | CSLLTEVETPIRNECSLLTEVETPIRNEWC | 2720 |
| 174 | CSLLTEVETPIRNEWCSLLTEVETPIRNEWC | 2647 |
| 212 | CSLLTEVETPIRNEWGCSLLTEVETPIRNEWC | 2545 |
| 218 | CLLTEVETPIRNEWGSCSLLTEVETPIRNEWC | 2541 |
| 188 | CLTEVETPIRNEWGSRCSLLTEVETPIRNEWC | 2522 |
| 225 | CTEVETPIRNEWGSRSCSLLTEVETPIRNEWC | 2482 |
| 238 | CEVETPIRNEWGSRSNCSLLTEVETPIRNEWC | 2391 |
| 234 | CVETPIRNEWGSRSNDCSLLTEVETPIRNEWC | 2412 |
| 251 | CETPIRNEWGSRSNDSCSLLTEVETPIRNEWC | 2374 |
| 272 | CTPIRNEWGSRSNDSSCSLLTEVETPIRNEWC | 2313 |
| 249 | CPIRNEWGSRSNDSSDCSLLTEVETPIRNEWC | 2397 |
| 281 | CSLLTEVETCSLLTEVETPIRNEWGC | 2479 |
| 186 | CSLLTEVETPCSLLTEVETPIRNEWGC | 2523 |
| 236 | CSLLTEVETPICSLLTEVETPIRNEWGC | 2345 |
| 167 | CSLLTEVETPIRCSLLTEVETPIRNEWGC | 2600 |
| 148 | CSLLTEVETPIRNCSLLTEVETPIRNEWGC | 2553 |
| 152 | CSLLTEVETPIRNECSLLTEVETPIRNEWGC | 2732 |
| 141 | CSLLTEVETPIRNEWCSLLTEVETPIRNEWGC | 2669 |
| 140 | CSLLTEVETPIRNEWGCSLLTEVETPIRNEWGC | 2678 |
| 205 | CLLTEVETPIRNEWGSCSLLTEVETPIRNEWGC | 2593 |
| 116 | CLTEVETPIRNEWGSRCSLLTEVETPIRNEWGC | 2492 |
| 125 | CTEVETPIRNEWGSRSCSLLTEVETPIRNEWGC | 2449 |
| 233 | CEVETPIRNEWGSRSNCSLLTEVETPIRNEWGC | 2442 |
| 257 | CVETPIRNEWGSRSNDCSLLTEVETPIRNEWGC | 2400 |
| 255 | CETPIRNEWGSRSNDSCSLLTEVETPIRNEWGC | 2414 |
| 243 | CTPIRNEWGSRSNDSSCSLLTEVETPIRNEWGC | 2466 |
| 256 | CPIRNEWGSRSNDSSDCSLLTEVETPIRNEWGC | 2460 |
| 179 | CSLLTEVETCLLTEVETPIRNEWGSC | 2416 |
| 182 | CSLLTEVETPCLLTEVETPIRNEWGSC | 2540 |
| 224 | CSLLTEVETPICLLTEVETPIRNEWGSC | 2388 |
| 160 | CSLLTEVETPIRCLLTEVETPIRNEWGSC | 2520 |
| 192 | CSLLTEVETPIRNCLLTEVETPIRNEWGSC | 2519 |
| 227 | CSLLTEVETPIRNECLLTEVETPIRNEWGSC | 2484 |
| 214 | CSLLTEVETPIRNEWCLLTEVETPIRNEWGSC | 2661 |
| 138 | CSLLTEVETPIRNEWGCLLTEVETPIRNEWGSC | 2624 |
| 1536 | CLLTEVETPIRNEWGSCLLTEVETPIRNEWGSC | 2616 |
| 1537 | CLTEVETPIRNEWGSRCLLTEVETPIRNEWGSC | 2667 |
| 1538 | CTEVETPIRNEWGSRSCLLTEVETPIRNEWGSC | 2425 |
| 1539 | CEVETPIRNEWGSRSNCLLTEVETPIRNEWGSC | 2461 |
| 1540 | CVETPIRNEWGSRSNDCLLTEVETPIRNEWGSC | 2218 |
| 1541 | CETPIRNEWGSRSNDSCLLTEVETPIRNEWGSC | 2255 |
| 1542 | CTPIRNEWGSRSNDSSCLLTEVETPIRNEWGSC | 2363 |
| 1543 | CPIRNEWGSRSNDSSDCLLTEVETPIRNEWGSC | 2260 |
| 215 | CSLLTEVETCLTEVETPIRNEWGSRC | 2328 |
| 221 | CSLLTEVETPCLTEVETPIRNEWGSRC | 2513 |
| 235 | CSLLTEVETPICLTEVETPIRNEWGSRC | 2351 |
| 170 | CSLLTEVETPIRCLTEVETPIRNEWGSRC | 2587 |
| 195 | CSLLTEVETPIRNCLTEVETPIRNEWGSRC | 2585 |
| 123 | CSLLTEVETPIRNECLTEVETPIRNEWGSRC | 2496 |
| 278 | CSLLTEVETPIRNEWCLTEVETPIRNEWGSRC | 2429 |
| 175 | CSLLTEVETPIRNEWGCLTEVETPIRNEWGSRC | 2641 |
| 1544 | CLLTEVETPIRNEWGSCLTEVETPIRNEWGSRC | 2500 |
| 250 | CSLLTEVETCTEVETPIRNEWGSRSC | 2474 |
| 222 | CSLLTEVETPCTEVETPIRNEWGSRSC | 2703 |
| 280 | CSLLTEVETPICTEVETPIRNEWGSRSC | 2241 |
| 199 | CSLLTEVETPIRCTEVETPIRNEWGSRSC | 2623 |
| 210 | CSLLTEVETPIRNCTEVETPIRNEWGSRSC | 2643 |

TABLE 3-continued

Peptides that show specific binding to Z3G1 (A numeral "1" in the peptide sequence indicates a differentially protected cystein allowing for selective CLIP attachment at certain residues)

| SEQ ID NO: | Peptides that bind to Z3G1 | Signal |
|---|---|---|
| 258 | CSLLTEVETPIRNECTEVETPIRNEWGSRSC | 2553 |
| 277 | CSLLTEVETPIRNEWCTEVETPIRNEWGSRSC | 2388 |
| 263 | CSLLTEVETPIRNEWGCTEVETPIRNEWGSRSC | 2496 |
| 1545 | CLLTEVETPIRNEWGSCTEVETPIRNEWGSRSC | 2592 |
| 239 | CSLLTEVETCEVETPIRNEWGSRSNC | 2549 |
| 274 | CSLLTEVETPCEVETPIRNEWGSRSNC | 2701 |
| 260 | CSLLTEVETPICEVETPIRNEWGSRSNC | 2680 |
| 209 | CSLLTEVETPIRCEVETPIRNEWGSRSNC | 2699 |
| 253 | CSLLTEVETPIRNCEVETPIRNEWGSRSNC | 2699 |
| 276 | CSLLTEVETPIRNECEVETPIRNEWGSRSNC | 2620 |
| 1546 | CSLLTEVETPIRNEWCEVETPIRNEWGSRSNC | 2519 |
| 275 | CSLLTEVETPIRNEWGCEVETPIRNEWGSRSNC | 2397 |
| 1547 | CLLTEVETPIRNEWGSCEVETPIRNEWGSRSNC | 2074 |
| 264 | CSLLTEVETCVETPIRNEWGSRSNDC | 2374 |
| 265 | CSLLTEVETPCVETPIRNEWGSRSNDC | 2484 |
| 1548 | CSLLTEVETPICVETPIRNEWGSRSNDC | 2174 |
| 271 | CSLLTEVETPIRCVETPIRNEWGSRSNDC | 2480 |
| 262 | CSLLTEVETPIRNCVETPIRNEWGSRSNDC | 2566 |
| 279 | CSLLTEVETPIRNECVETPIRNEWGSRSNDC | 2465 |
| 1549 | CSLLTEVETPIRNEWCVETPIRNEWGSRSNDC | 2433 |
| 159 | CSLLTEVETPIRNEWGCVETPIRNEWGSRSNDC | 2415 |
| 320 | SLLTEVGSLLTEV | 2530 |
| 283 | CSLLTEVGSLLTEV | 2903 |
| 390 | CLLTEVGSLLTEV | 2494 |
| 500 | SCLTEVGSLLTEV | 1610 |
| 324 | SLCTEVGSLLTEV | 1780 |
| 336 | SLLCEVGSLLTEV | 2475 |
| 824 | SLLTCVGSLLTEV | 1772 |
| 482 | CLCTCVGSLLTEV | 1953 |
| 354 | SLLTEVGCSLLTEV | 2511 |
| 807 | CLLTEVGCSLLTEV | 1558 |
| 580 | SLCTEVGCSLLTEV | 2382 |
| 511 | SLLCEVGCSLLTEV | 2562 |
| 810 | SLLTCVGCSLLTEV | 1992 |
| 798 | CLCTCVGCSLLTEV | 1489 |
| 311 | SLLTEVGCLLTEV | 1924 |
| 388 | CSLLTEVGCLLTEV | 2427 |
| 1550 | SLLCEVGCLLTEV | 1997 |
| 302 | ASLLTEVGSCLTEV | 2770 |
| 345 | CSLLTEVGSCLTEV | 2703 |
| 1551 | SLLCEVGSCLTEV | 2499 |
| 464 | SLLTEVGSLCTEV | 2219 |
| 711 | CSLLTEVGSLCTEV | 2409 |
| 1552 | SLLCEVGSLCTEV | 2722 |
| 314 | SLLTEVGSLLCEV | 2392 |
| 792 | CSLLTEVGSLLCEV | 2594 |
| 1553 | CLLTEVGSLLCEV | 2168 |
| 496 | SCLTEVGSLLCEV | 1896 |
| 506 | SLCTEVGSLLCEV | 1863 |
| 1554 | SLLCEVGSLLCEV | 2399 |
| 1555 | SLLTCVGSLLCEV | 2264 |
| 477 | SLLTECGSLLCEV | 2403 |
| 1556 | CSCLCEVGSLLCEV | 1583 |
| 1557 | CLCTCVGSLLCEV | 2246 |
| 1558 | SCLCECGSLLCEV | 1747 |
| 814 | CSLLTECGSLLCEV | 2256 |
| 284 | ASLLTEVGSLLTCV | 2358 |
| 290 | CSLLTEVGSLLTCV | 2503 |
| 1559 | SLLCEVGSLLTCV | 1972 |
| 452 | SLLTEVGSLLTEC | 1862 |
| 292 | CSLLTEVGSLLTEC | 2213 |
| 351 | SLLCEVGSLLTEC | 2438 |
| 525 | SLLTEVGCSCLCEV | 1829 |
| 379 | SLCTEVGCSCLCEV | 1500 |
| 1560 | SLLCEVGCSCLCEV | 2112 |
| 299 | SLLTEVGCLCTCV | 2346 |
| 385 | CSLLTEVGCLCTCV | 2474 |
| 1561 | SLLCEVGCLCTCV | 2331 |
| 329 | SLLTEVGSCLCEC | 2558 |
| 533 | CSLLTEVGSCLCEC | 2625 |
| 1562 | SLLCEVGSCLCEC | 2614 |

TABLE 3-continued

Peptides that show specific binding to Z3G1 (A numeral "1" in the peptide sequence indicates a differentially protected cystein allowing for selective CLIP attachment at certain residues)

| SEQ ID NO: | Peptides that bind to Z3G1 | Signal |
|---|---|---|
| 353 | SLLTEVGCSLLTEC | 2380 |
| 747 | SLCTEVGCSLLTEC | 2050 |
| 301 | SLLCEVGCSLLTEC | 2637 |
| 341 | CSLLTEVCSLLTEC | 1122 |
| 321 | ALLTEVETPIRNEWGCRCNDSSD | 2225 |
| 1563 | DLLTEVETPIRNEWGCRCNDSSD | 2320 |
| 1564 | ELLTEVETPIRNEWGCRCNDSSD | 2201 |
| 1565 | FLLTEVETPIRNEWGCRCNDSSD | 1018 |
| 1566 | GLLTEVETPIRNEWGCRCNDSSD | 2321 |
| 1567 | HLLTEVETPIRNEWGCRCNDSSD | 1946 |
| 1568 | ILLTEVETPIRNEWGCRCNDSSD | 1044 |
| 1569 | KLLTEVETPIRNEWGCRCNDSSD | 1826 |
| 538 | LLLTEVETPIRNEWGCRCNDSSD | 1399 |
| 1570 | MLLTEVETPIRNEWGCRCNDSSD | 2126 |
| 1571 | NLLTEVETPIRNEWGCRCNDSSD | 2135 |
| 1572 | PLLTEVETPIRNEWGCRCNDSSD | 1641 |
| 1573 | QLLTEVETPIRNEWGCRCNDSSD | 1627 |
| 1574 | RLLTEVETPIRNEWGCRCNDSSD | 1338 |
| 326 | SLLTEVETPIRNEWGCRCNDSSD | 2476 |
| 312 | TLLTEVETPIRNEWGCRCNDSSD | 2510 |
| 520 | VLLTEVETPIRNEWGCRCNDSSD | 1758 |
| 1575 | WLLTEVETPIRNEWGCRCNDSSD | 2180 |
| 1576 | YLLTEVETPIRNEWGCRCNDSSD | 1882 |
| 349 | SLATEVETPIRNEWGCRCNDSSD | 2145 |
| 1577 | SLDTEVETPIRNEWGCRCNDSSD | 1505 |
| 328 | SLETEVETPIRNEWGCRCNDSSD | 1963 |
| 459 | SLITEVETPIRNEWGCRCNDSSD | 1996 |
| 377 | SLKTEVETPIRNEWGCRCNDSSD | 1453 |
| 327 | SLMTEVETPIRNEWGCRCNDSSD | 2149 |
| 449 | SLNTEVETPIRNEWGCRCNDSSD | 1908 |
| 352 | SLQTEVETPIRNEWGCRCNDSSD | 2025 |
| 510 | SLRTEVETPIRNEWGCRCNDSSD | 1034 |
| 473 | SLSTEVETPIRNEWGCRCNDSSD | 2052 |
| 478 | SLTTEVETPIRNEWGCRCNDSSD | 1804 |
| 484 | SLVTEVETPIRNEWGCRCNDSSD | 2029 |
| 1578 | SLLAEVETPIRNEWGCRCNDSSD | 2356 |
| 1579 | SLLDEVETPIRNEWGCRCNDSSD | 2276 |
| 1580 | SLLEEVETPIRNEWGCRCNDSSD | 2420 |
| 1581 | SLLFEVETPIRNEWGCRCNDSSD | 2137 |
| 1582 | SLLGEVETPIRNEWGCRCNDSSD | 2301 |
| 1583 | SLLHEVETPIRNEWGCRCNDSSD | 2462 |
| 1584 | SLLIEVETPIRNEWGCRCNDSSD | 1899 |
| 1585 | SLLKEVETPIRNEWGCRCNDSSD | 2611 |
| 1586 | SLLLEVETPIRNEWGCRCNDSSD | 2344 |
| 346 | SLLMEVETPIRNEWGCRCNDSSD | 2477 |
| 1587 | SLLNEVETPIRNEWGCRCNDSSD | 2425 |
| 381 | SLLQEVETPIRNEWGCRCNDSSD | 2432 |
| 1588 | SLLREVETPIRNEWGCRCNDSSD | 2286 |
| 803 | SLLSEVETPIRNEWGCRCNDSSD | 2305 |
| 1589 | SLLVEVETPIRNEWGCRCNDSSD | 1932 |
| 1590 | SLLWEVETPIRNEWGCRCNDSSD | 2221 |
| 1591 | SLLYEVETPIRNEWGCRCNDSSD | 2181 |
| 822 | SLLTDVETPIRNEWGCRCNDSSD | 1113 |
| 522 | SLLTMVETPIRNEWGCRCNDSSD | 1244 |
| 608 | SLLTEIETPIRNEWGCRCNDSSD | 2016 |
| 556 | SLLTELETPIRNEWGCRCNDSSD | 1380 |
| 547 | SLLTETETPIRNEWGCRCNDSSD | 1594 |
| 551 | SLLTEVATPIRNEWGCRCNDSSD | 2093 |
| 657 | SLLTEVDTPIRNEWGCRCNDSSD | 2095 |
| 731 | SLLTEVFTPIRNEWGCRCNDSSD | 1708 |
| 784 | SLLTEVGTPIRNEWGCRCNDSSD | 2005 |
| 690 | SLLTEVHTPIRNEWGCRCNDSSD | 2057 |
| 795 | SLLTEVITPIRNEWGCRCNDSSD | 1438 |
| 705 | SLLTEVKTPIRNEWGCRCNDSSD | 1905 |
| 709 | SLLTEVLTPIRNEWGCRCNDSSD | 1743 |
| 629 | SLLTEVMTPIRNEWGCRCNDSSD | 2331 |
| 675 | SLLTEVNTPIRNEWGCRCNDSSD | 2150 |
| 594 | SLLTEVQTPIRNEWGCRCNDSSD | 2289 |
| 575 | SLLTEVRTPIRNEWGCRCNDSSD | 1024 |
| 545 | SLLTEVSTPIRNEWGCRCNDSSD | 2288 |
| 553 | SLLTEVTTPIRNEWGCRCNDSSD | 2102 |

TABLE 3-continued

Peptides that show specific binding to Z3G1 (A numeral "1" in the peptide sequence indicates a differentially protected cystein allowing for selective CLIP attachment at certain residues)

| SEQ ID NO: | Peptides that bind to Z3G1 | Signal |
|---|---|---|
| 645 | SLLTEVVTPIRNEWGCRCNDSSD | 1492 |
| 583 | SLLTEVWTPIRNEWGCRCNDSSD | 1889 |
| 658 | SLLTEVYTPIRNEWGCRCNDSSD | 1092 |
| 635 | SLLTEVEAPIRNEWGCRCNDSSD | 2325 |
| 779 | SLLTEVEDPIRNEWGCRCNDSSD | 2216 |
| 652 | SLLTEVEEPIRNEWGCRCNDSSD | 2362 |
| 621 | SLLTEVEFPIRNEWGCRCNDSSD | 2297 |
| 646 | SLLTEVEGPIRNEWGCRCNDSSD | 2341 |
| 450 | SLLTEVEHPIRNEWGCRCNDSSD | 2241 |
| 593 | SLLTEVEIPIRNEWGCRCNDSSD | 2365 |
| 534 | SLLTEVEKPIRNEWGCRCNDSSD | 2505 |
| 564 | SLLTEVELPIRNEWGCRCNDSSD | 2407 |
| 590 | SLLTEVEMPIRNEWGCRCNDSSD | 2516 |
| 467 | SLLTEVENPIRNEWGCRCNDSSD | 2549 |
| 537 | SLLTEVEPPIRNEWGCRCNDSSD | 2522 |
| 527 | SLLTEVEQPIRNEWGCRCNDSSD | 2344 |
| 599 | SLLTEVERPIRNEWGCRCNDSSD | 2131 |
| 607 | SLLTEVESPIRNEWGCRCNDSSD | 2156 |
| 695 | SLLTEVEVPIRNEWGCRCNDSSD | 2286 |
| 763 | SLLTEVEWPIRNEWGCRCNDSSD | 2178 |
| 783 | SLLTEVEYPIRNEWGCRCNDSSD | 2113 |
| 559 | SLLTEVETAIRNEWGCRCNDSSD | 2415 |
| 610 | SLLTEVETDIRNEWGCRCNDSSD | 2392 |
| 602 | SLLTEVETEIRNEWGCRCNDSSD | 2368 |
| 549 | SLLTEVETFIRNEWGCRCNDSSD | 2301 |
| 597 | SLLTEVETGIRNEWGCRCNDSSD | 2366 |
| 609 | SLLTEVETHIRNEWGCRCNDSSD | 2288 |
| 653 | SLLTEVETIIRNEWGCRCNDSSD | 2096 |
| 300 | SLLTEVETKIRNEWGCRCNDSSD | 2485 |
| 491 | SLLTEVETLIRNEWGCRCNDSSD | 2225 |
| 493 | SLLTEVETMIRNEWGCRCNDSSD | 2320 |
| 529 | SLLTEVETNIRNEWGCRCNDSSD | 2253 |
| 606 | SLLTEVETQIRNEWGCRCNDSSD | 2189 |
| 611 | SLLTEVETRIRNEWGCRCNDSSD | 2159 |
| 700 | SLLTEVETSIRNEWGCRCNDSSD | 2151 |
| 649 | SLLTEVETTIRNEWGCRCNDSSD | 2295 |
| 614 | SLLTEVETVIRNEWGCRCNDSSD | 2264 |
| 670 | SLLTEVETWIRNEWGCRCNDSSD | 2146 |
| 581 | SLLTEVETYIRNEWGCRCNDSSD | 2290 |
| 715 | SLLTEVETPARNEWGCRCNDSSD | 2244 |
| 660 | SLLTEVETPDRNEWGCRCNDSSD | 2390 |
| 630 | SLLTEVETPERNEWGCRCNDSSD | 2480 |
| 665 | SLLTEVETPFRNEWGCRCNDSSD | 2229 |
| 495 | SLLTEVETPGRNEWGCRCNDSSD | 2676 |
| 591 | SLLTEVETPHRNEWGCRCNDSSD | 2425 |
| 392 | SLLTEVETPKRNEWGCRCNDSSD | 2300 |
| 461 | SLLTEVETPLRNEWGCRCNDSSD | 2239 |
| 457 | SLLTEVETPMRNEWGCRCNDSSD | 2297 |
| 770 | SLLTEVETPNRNEWGCRCNDSSD | 2299 |
| 738 | SLLTEVETPPRNEWGCRCNDSSD | 2302 |
| 782 | SLLTEVETPQRNEWGCRCNDSSD | 2341 |
| 750 | SLLTEVETPRRNEWGCRCNDSSD | 2376 |
| 673 | SLLTEVETPSRNEWGCRCNDSSD | 2396 |
| 758 | SLLTEVETPTRNEWGCRCNDSSD | 2417 |
| 650 | SLLTEVETPVRNEWGCRCNDSSD | 2331 |
| 693 | SLLTEVETPWRNEWGCRCNDSSD | 2190 |
| 389 | SLLTEVETPYRNEWGCRCNDSSD | 2303 |
| 707 | SLLTEVETPIANEWGCRCNDSSD | 2302 |
| 524 | SLLTEVETPIDNEWGCRCNDSSD | 2337 |
| 676 | SLLTEVETPIENEWGCRCNDSSD | 2252 |
| 576 | SLLTEVETPIFNEWGCRCNDSSD | 2176 |
| 744 | SLLTEVETPIGNEWGCRCNDSSD | 2073 |
| 488 | SLLTEVETPIHNEWGCRCNDSSD | 2121 |
| 720 | SLLTEVETPIINEWGCRCNDSSD | 2262 |
| 778 | SLLTEVETPIKNEWGCRCNDSSD | 2322 |
| 692 | SLLTEVETPILNEWGCRCNDSSD | 2363 |
| 454 | SLLTEVETPIMNEWGCRCNDSSD | 2369 |
| 780 | SLLTEVETPINNEWGCRCNDSSD | 2277 |
| 357 | SLLTEVETPIPNEWGCRCNDSSD | 2515 |
| 677 | SLLTEVETPIQNEWGCRCNDSSD | 2372 |
| 754 | SLLTEVETPISNEWGCRCNDSSD | 2292 |

TABLE 3-continued

Peptides that show specific binding to Z3G1 (A numeral "1" in the peptide sequence indicates a differentially protected cystein allowing for selective CLIP attachment at certain residues)

| SEQ ID NO: | Peptides that bind to Z3G1 | Signal |
|---|---|---|
| 766 | SLLTEVETPITNEWGCRCNDSSD | 2358 |
| 680 | SLLTEVETPIVNEWGCRCNDSSD | 2366 |
| 656 | SLLTEVETPIWNEWGCRCNDSSD | 2250 |
| 509 | SLLTEVETPIYNEWGCRCNDSSD | 2296 |
| 582 | SLLTEVETPIRAEWGCRCNDSSD | 2306 |
| 698 | SLLTEVETPIRDEWGCRCNDSSD | 2187 |
| 771 | SLLTEVETPIREEWGCRCNDSSD | 2156 |
| 620 | SLLTEVETPIRFEWGCRCNDSSD | 2364 |
| 773 | SLLTEVETPIRGEWGCRCNDSSD | 2228 |
| 721 | SLLTEVETPIRHEWGCRCNDSSD | 2296 |
| 627 | SLLTEVETPIRIEWGCRCNDSSD | 2444 |
| 631 | SLLTEVETPIRKEWGCRCNDSSD | 2437 |
| 585 | SLLTEVETPIRLEWGCRCNDSSD | 2468 |
| 622 | SLLTEVETPIRMEWGCRCNDSSD | 2385 |
| 753 | SLLTEVETPIRPEWGCRCNDSSD | 2301 |
| 661 | SLLTEVETPIRQEWGCRCNDSSD | 2367 |
| 710 | SLLTEVETPIRREWGCRCNDSSD | 2278 |
| 678 | SLLTEVETPIRSEWGCRCNDSSD | 2322 |
| 387 | SLLTEVETPIRTEWGCRCNDSSD | 2360 |
| 565 | SLLTEVETPIRVEWGCRCNDSSD | 2300 |
| 562 | SLLTEVETPIRWEWGCRCNDSSD | 2302 |
| 654 | SLLTEVETPIRYEWGCRCNDSSD | 2202 |
| 666 | SLLTEVETPIRNAWGCRCNDSSD | 2334 |
| 712 | SLLTEVETPIRNDWGCRCNDSSD | 2324 |
| 662 | SLLTEVETPIRNFWGCRCNDSSD | 2417 |
| 643 | SLLTEVETPIRNGWGCRCNDSSD | 2408 |
| 684 | SLLTEVETPIRNHWGCRCNDSSD | 2377 |
| 577 | SLLTEVETPIRNIWGCRCNDSSD | 2490 |
| 640 | SLLTEVETPIRNKWGCRCNDSSD | 2402 |
| 571 | SLLTEVETPIRNLWGCRCNDSSD | 2415 |
| 605 | SLLTEVETPIRNMWGCRCNDSSD | 2455 |
| 741 | SLLTEVETPIRNNWGCRCNDSSD | 2319 |
| 616 | SLLTEVETPIRNPWGCRCNDSSD | 2288 |
| 512 | SLLTEVETPIRNQWGCRCNDSSD | 2402 |
| 546 | SLLTEVETPIRNRWGCRCNDSSD | 2257 |
| 617 | SLLTEVETPIRNSWGCRCNDSSD | 2300 |
| 380 | SLLTEVETPIRNTWGCRCNDSSD | 2314 |
| 685 | SLLTEVETPIRNVWGCRCNDSSD | 2281 |
| 703 | SLLTEVETPIRNWWGCRCNDSSD | 2293 |
| 702 | SLLTEVETPIRNYWGCRCNDSSD | 2311 |
| 453 | SLLTEVETPIRNEAGCRCNDSSD | 2383 |
| 751 | SLLTEVETPIRNEDGCRCNDSSD | 2359 |
| 787 | SLLTEVETPIRNEEGCRCNDSSD | 2330 |
| 716 | SLLTEVETPIRNEFGCRCNDSSD | 2444 |
| 708 | SLLTEVETPIRNEGGCRCNDSSD | 2486 |
| 696 | SLLTEVETPIRNEHGCRCNDSSD | 2398 |
| 636 | SLLTEVETPIRNEIGCRCNDSSD | 2402 |
| 572 | SLLTEVETPIRNEKGCRCNDSSD | 2580 |
| 641 | SLLTEVETPIRNELGCRCNDSSD | 2436 |
| 517 | SLLTEVETPIRNEMGCRCNDSSD | 2398 |
| 637 | SLLTEVETPIRNENGCRCNDSSD | 2265 |
| 671 | SLLTEVETPIRNEPGCRCNDSSD | 2279 |
| 765 | SLLTEVETPIRNEQGCRCNDSSD | 2264 |
| 737 | SLLTEVETPIRNERGCRCNDSSD | 2328 |
| 745 | SLLTEVETPIRNESGCRCNDSSD | 2346 |
| 688 | SLLTEVETPIRNETGCRCNDSSD | 2401 |
| 386 | SLLTEVETPIRNEVGCRCNDSSD | 2411 |
| 384 | SLLTEVETPIRNEYGCRCNDSSD | 2426 |
| 681 | SLLTEVETPIRNEWACRCNDSSD | 2431 |
| 717 | SLLTEVETPIRNEWDCRCNDSSD | 2322 |
| 726 | SLLTEVETPIRNEWECRCNDSSD | 2364 |
| 596 | SLLTEVETPIRNEWFCRCNDSSD | 2493 |
| 633 | SLLTEVETPIRNEWHCRCNDSSD | 2327 |
| 347 | SLLTEVETPIRNEWICRCNDSSD | 2359 |
| 541 | SLLTEVETPIRNEWKCRCNDSSD | 2328 |
| 569 | SLLTEVETPIRNEWLCRCNDSSD | 2379 |
| 642 | SLLTEVETPIRNEWMCRCNDSSD | 2378 |
| 785 | SLLTEVETPIRNEWNCRCNDSSD | 2236 |
| 774 | SLLTEVETPIRNEWPCRCNDSSD | 2328 |
| 760 | SLLTEVETPIRNEWQCRCNDSSD | 2338 |
| 704 | SLLTEVETPIRNEWRCRCNDSSD | 2371 |

TABLE 3-continued

Peptides that show specific binding to Z3G1 (A numeral "1" in the peptide sequence indicates a differentially protected cystein allowing for selective CLIP attachment at certain residues)

| SEQ ID NO: | Peptides that bind to Z3G1 | Signal |
|---|---|---|
| 735 | SLLTEVETPIRNEWSCRCNDSSD | 2374 |
| 669 | SLLTEVETPIRNEWTCRCNDSSD | 2401 |
| 624 | SLLTEVETPIRNEWVCRCNDSSD | 2418 |
| 366 | SLLTEVETPIRNEWWCRCNDSSD | 2406 |
| 625 | SLLTEVETPIRNEWYCRCNDSSD | 2362 |
| 659 | SLLTEVETPIRNEWGARCNDSSD | 2396 |
| 790 | SLLTEVETPIRNEWGDRCNDSSD | 2267 |
| 370 | SLLTEVETPIRNEWGERCNDSSD | 2286 |
| 504 | SLLTEVETPIRNEWGFRCNDSSD | 2349 |
| 563 | SLLTEVETPIRNEWGGRCNDSSD | 2270 |
| 647 | SLLTEVETPIRNEWGHRCNDSSD | 2113 |
| 667 | SLLTEVETPIRNEWGIRCNDSSD | 2211 |
| 648 | SLLTEVETPIRNEWGKRCNDSSD | 2295 |
| 600 | SLLTEVETPIRNEWGLRCNDSSD | 2389 |
| 732 | SLLTEVETPIRNEWGMRCNDSSD | 2269 |
| 664 | SLLTEVETPIRNEWGNRCNDSSD | 2328 |
| 727 | SLLTEVETPIRNEWGPRCNDSSD | 2334 |
| 713 | SLLTEVETPIRNEWGQRCNDSSD | 2369 |
| 672 | SLLTEVETPIRNEWGRRCNDSSD | 2372 |
| 682 | SLLTEVETPIRNEWGSRCNDSSD | 2346 |
| 638 | SLLTEVETPIRNEWGTRCNDSSD | 2404 |
| 644 | SLLTEVETPIRNEWGVRCNDSSD | 2444 |
| 595 | SLLTEVETPIRNEWGWRCNDSSD | 2439 |
| 668 | SLLTEVETPIRNEWGYRCNDSSD | 2410 |
| 683 | SLLTEVETPIRNEWGCACNDSSD | 2301 |
| 501 | SLLTEVETPIRNEWGCCCNDSSD | 2515 |
| 615 | SLLTEVETPIRNEWGCDCNDSSD | 2207 |
| 679 | SLLTEVETPIRNEWGCECNDSSD | 2148 |
| 639 | SLLTEVETPIRNEWGCFCNDSSD | 2312 |
| 775 | SLLTEVETPIRNEWGCGCNDSSD | 2186 |
| 776 | SLLTEVETPIRNEWGCHCNDSSD | 2134 |
| 722 | SLLTEVETPIRNEWGCICNDSSD | 2269 |
| 701 | SLLTEVETPIRNEWGCKCNDSSD | 2290 |
| 748 | SLLTEVETPIRNEWGCLCNDSSD | 2292 |
| 730 | SLLTEVETPIRNEWGCMCNDSSD | 2413 |
| 743 | SLLTEVETPIRNEWGCNCNDSSD | 2340 |
| 767 | SLLTEVETPIRNEWGCPCNDSSD | 2295 |
| 756 | SLLTEVETPIRNEWGCQCNDSSD | 2294 |
| 736 | SLLTEVETPIRNEWGCSCNDSSD | 2348 |
| 719 | SLLTEVETPIRNEWGCTCNDSSD | 2347 |
| 742 | SLLTEVETPIRNEWGCVCNDSSD | 2334 |
| 503 | SLLTEVETPIRNEWGCWCNDSSD | 2437 |
| 552 | SLLTEVETPIRNEWGCYCNDSSD | 2397 |
| 634 | SLLTEVETPIRNEWGCRANDSSD | 2265 |
| 794 | SLLTEVETPIRNEWGCRDNDSSD | 2033 |
| 796 | SLLTEVETPIRNEWGCRENDSSD | 2097 |
| 723 | SLLTEVETPIRNEWGCRFNDSSD | 2303 |
| 752 | SLLTEVETPIRNEWGCRGNDSSD | 2345 |
| 734 | SLLTEVETPIRNEWGCRHNDSSD | 2353 |
| 697 | SLLTEVETPIRNEWGCRINDSSD | 2409 |
| 598 | SLLTEVETPIRNEWGCRKNDSSD | 2435 |
| 686 | SLLTEVETPIRNEWGCRLNDSSD | 2363 |
| 691 | SLLTEVETPIRNEWGCRMNDSSD | 2356 |
| 746 | SLLTEVETPIRNEWGCRNNDSSD | 2384 |
| 757 | SLLTEVETPIRNEWGCRPNDSSD | 2326 |
| 772 | SLLTEVETPIRNEWGCRQNDSSD | 2327 |
| 584 | SLLTEVETPIRNEWGCRRNDSSD | 2383 |
| 519 | SLLTEVETPIRNEWGCRSNDSSD | 2344 |
| 573 | SLLTEVETPIRNEWGCRTNDSSD | 2374 |
| 375 | SLLTEVETPIRNEWGCRVNDSSD | 2316 |
| 579 | SLLTEVETPIRNEWGCRWNDSSD | 2364 |
| 699 | SLLTEVETPIRNEWGCRYNDSSD | 2169 |
| 706 | SLLTEVETPIRNEWGCRCADSSD | 2329 |
| 728 | SLLTEVETPIRNEWGCRCCDSSD | 2377 |
| 762 | SLLTEVETPIRNEWGCRCDDSSD | 2289 |
| 739 | SLLTEVETPIRNEWGCRCEDSSD | 2273 |
| 560 | SLLTEVETPIRNEWGCRCFDSSD | 2538 |
| 689 | SLLTEVETPIRNEWGCRCGDSSD | 2343 |
| 651 | SLLTEVETPIRNEWGCRCHDSSD | 2350 |
| 612 | SLLTEVETPIRNEWGCRCIDSSD | 2450 |
| 318 | SLLTEVETPIRNEWGCRCKDSSD | 2549 |

TABLE 3-continued

Peptides that show specific binding to Z3G1 (A numeral "1" in the peptide sequence indicates a differentially protected cystein allowing for selective CLIP attachment at certain residues)

| SEQ ID NO: | Peptides that bind to Z3G1 | Signal |
|---|---|---|
| 618 | SLLTEVETPIRNEWGCRCLDSSD | 2480 |
| 628 | SLLTEVETPIRNEWGCRCMDSSD | 2470 |
| 516 | SLLTEVETPIRNEWGCRCPDSSD | 2449 |
| 568 | SLLTEVETPIRNEWGCRCQDSSD | 2438 |
| 544 | SLLTEVETPIRNEWGCRCRDSSD | 2447 |
| 729 | SLLTEVETPIRNEWGCRCSDSSD | 2141 |
| 674 | SLLTEVETPIRNEWGCRCTDSSD | 2253 |
| 632 | SLLTEVETPIRNEWGCRCVDSSD | 2366 |
| 555 | SLLTEVETPIRNEWGCRCWDSSD | 2462 |
| 626 | SLLTEVETPIRNEWGCRCYDSSD | 2385 |
| 619 | SLLTEVETPIRNEWGCRCNASSD | 2454 |
| 588 | SLLTEVETPIRNEWGCRCNCSSD | 2505 |
| 694 | SLLTEVETPIRNEWGCRCNESSD | 2282 |
| 535 | SLLTEVETPIRNEWGCRCNFSSD | 2509 |
| 603 | SLLTEVETPIRNEWGCRCNGSSD | 2418 |
| 613 | SLLTEVETPIRNEWGCRCNHSSD | 2439 |
| 586 | SLLTEVETPIRNEWGCRCNISSD | 2517 |
| 465 | SLLTEVETPIRNEWGCRCNKSSD | 2597 |
| 393 | SLLTEVETPIRNEWGCRCNLSSD | 2634 |
| 394 | SLLTEVETPIRNEWGCRCNMSSD | 2574 |
| 395 | SLLTEVETPIRNEWGCRCNNSSD | 2502 |
| 396 | SLLTEVETPIRNEWGCRCNPSSD | 2445 |
| 397 | SLLTEVETPIRNEWGCRCNQSSD | 2376 |
| 398 | SLLTEVETPIRNEWGCRCNRSSD | 2514 |
| 342 | SLLTEVETPIRNEWGCRCNSSSD | 2440 |
| 399 | SLLTEVETPIRNEWGCRCNTSSD | 2483 |
| 400 | SLLTEVETPIRNEWGCRCNVSSD | 2476 |
| 401 | SLLTEVETPIRNEWGCRCNWSSD | 2556 |
| 337 | SLLTEVETPIRNEWGCRCNYSSD | 2475 |
| 402 | SLLTEVETPIRNEWGCRCNDASD | 2267 |
| 403 | SLLTEVETPIRNEWGCRCNDCSD | 2318 |
| 404 | SLLTEVETPIRNEWGCRCNDDSD | 2237 |
| 405 | SLLTEVETPIRNEWGCRCNDESD | 2203 |
| 406 | SLLTEVETPIRNEWGCRCNDFSD | 2395 |
| 338 | SLLTEVETPIRNEWGCRCNDGSD | 2226 |
| 407 | SLLTEVETPIRNEWGCRCNDHSD | 2537 |
| 408 | SLLTEVETPIRNEWGCRCNDISD | 2527 |
| 409 | SLLTEVETPIRNEWGCRCNDKSD | 2484 |
| 410 | SLLTEVETPIRNEWGCRCNDLSD | 2494 |
| 411 | SLLTEVETPIRNEWGCRCNDMSD | 2405 |
| 412 | SLLTEVETPIRNEWGCRCNDNSD | 2389 |
| 413 | SLLTEVETPIRNEWGCRCNDPSD | 2450 |
| 414 | SLLTEVETPIRNEWGCRCNDQSD | 2349 |
| 415 | SLLTEVETPIRNEWGCRCNDRSD | 2502 |
| 416 | SLLTEVETPIRNEWGCRCNDTSD | 2394 |
| 417 | SLLTEVETPIRNEWGCRCNDVSD | 2389 |
| 418 | SLLTEVETPIRNEWGCRCNDWSD | 2491 |
| 330 | SLLTEVETPIRNEWGCRCNDYSD | 2445 |
| 419 | SLLTEVETPIRNEWGCRCNDSAD | 2219 |
| 420 | SLLTEVETPIRNEWGCRCNDSCD | 2269 |
| 356 | SLLTEVETPIRNEWGCRCNDSDD | 2181 |
| 421 | SLLTEVETPIRNEWGCRCNDSED | 2527 |
| 422 | SLLTEVETPIRNEWGCRCNDSFD | 2492 |
| 313 | SLLTEVETPIRNEWGCRCNDSGD | 2485 |
| 423 | SLLTEVETPIRNEWGCRCNDSHD | 2353 |
| 424 | SLLTEVETPIRNEWGCRCNDSID | 2320 |
| 425 | SLLTEVETPIRNEWGCRCNDSKD | 2361 |
| 426 | SLLTEVETPIRNEWGCRCNDSLD | 2400 |
| 427 | SLLTEVETPIRNEWGCRCNDSMD | 2304 |
| 350 | SLLTEVETPIRNEWGCRCNDSND | 2299 |
| 428 | SLLTEVETPIRNEWGCRCNDSPD | 2344 |
| 429 | SLLTEVETPIRNEWGCRCNDSQD | 2175 |
| 430 | SLLTEVETPIRNEWGCRCNDSRD | 2373 |
| 431 | SLLTEVETPIRNEWGCRCNDSTD | 2205 |
| 432 | SLLTEVETPIRNEWGCRCNDSVD | 2232 |
| 433 | SLLTEVETPIRNEWGCRCNDSWD | 2477 |
| 434 | SLLTEVETPIRNEWGCRCNDSYD | 2479 |
| 435 | SLLTEVETP | 2380 |
| 436 | SLLTEVETPI | 2465 |
| 437 | SLLTEVETPIR | 2297 |
| 438 | SLLTEVETPIRN | 2130 |

TABLE 3-continued

| Peptides that show specific binding to Z3G1 (A numeral "1" in the peptide sequence indicates a differentially protected cystein allowing for selective CLIP attachment at certain residues) | | |
|---|---|---|
| SEQ ID NO: | Peptides that bind to Z3G1 | Signal |
| 439 | SLLTEVETPIRNE | 1819 |
| 440 | SLLTEVETPIRNEW | 2334 |
| 368 | SLLTEVETPIRNEWG | 2429 |
| 442 | SLLTEVETPIRNEWGC | 2369 |
| 443 | SLLTEVETPIRNEWGCR | 2444 |
| 444 | SLLTEVETPIRNEWGCRC | 2478 |
| 445 | SLLTEVETPIRNEWGCRCN | 2506 |
| 446 | SLLTEVETPIRNEWGCRCND | 2276 |
| 447 | SLLTEVETPIRNEWGCRCNDS | 2348 |
| 448 | SLLTEVETPIRNEWGCRCNDSS | 2325 |

Further, the peptides were screened for the ability to specifically bind 23K21 and 8I10 and NOT Z3G. In one set, peptides with high binding values for 23K21 and 8I10 that are NOT recognized by Z3G1 were identified. In a second set, peptides with high binding values for Z3G1 that are NOT recognized by 23K21 and 8I10 were identified.

Peptide sequences with high binding values for 23K12 and BI10 with no binding to Z3G1 were identified for low stringency (0.01 μg/mL) conditions (Table 4A) and high stringency (0.001 μg/mL) conditions (Table 4B).

TABLE 4A

| | |
|---|---|
| MCLCTCVGCSLLTEC | SEQ ID NO: 315 |
| CLCTCVGCSLLTEC | SEQ ID NO: 819 |
| SLLTECGCSCLCEV | SEQ ID NO: 567 |
| MSCLCECGCSLLTEC | SEQ ID NO: 340 |
| SLLTECGCSLLTEC | SEQ ID NO: 374 |
| CSLLTECGCSLLTEC | SEQ ID NO: 483 |
| SLLTECGSCLCEC | SEQ ID NO: 497 |
| MSLLTECGCSLLTEC | SEQ ID NO: 818 |
| CSCLCEVGCSLLTEC | SEQ ID NO: 335 |
| SLLTECGSCLTEV | SEQ ID NO: 601 |
| CLCTCVGSLLTEC | SEQ ID NO: 455 |
| SCLTEVGSLLTEC | SEQ ID NO: 823 |
| CSLLTECGSCLCEC | SEQ ID NO: 815 |
| CSLLTECGMSCLCEC | SEQ ID NO: 558 |
| MSLLTCVGCSLLTEC | SEQ ID NO: 820 |
| CSLLTECGSLLTEC | SEQ ID NO: 813 |
| SCLTEVGCSLLTEC | SEQ ID NO: 808 |
| SCLCECGCSLLTEC | SEQ ID NO: 361 |
| MSCLTEVGCSLLTEC | SEQ ID NO: 799 |
| CSLLTECGCSCLCEV | SEQ ID NO: 817 |
| CSCLCEVGMSLLTEC | SEQ ID NO: 305 |
| SLLTECGCLLTEV | SEQ ID NO: 462 |

TABLE 4B

| | |
|---|---|
| CSLLTECG-SLLTCV | SEQ ID NO: 1592 |
| CSLLTECGMSLLTCV | SEQ ID NO: 306 |
| SLLTECG-SLLTCV | SEQ ID NO: 1593 |
| MSLLTECGMCLLTEV | SEQ ID NO: 489 |
| MSLLTECGMSLLTCV | SEQ ID NO: 331 |
| SLLTECGCSLLTEC | SEQ ID NO: 374 |

Properties of the peptides that bind specifically to HuM2e antibodies 23K12/BI10 at different stringency conditions were analyzed. Antibodies 8i10 and 23k12 bind a conformational epitope with SLLTE as its core sequence. The best 23k12 binder is SLLTEVGSLLTEV (SEQ ID NO: 320), which is also recognized by Z3G1. The best 8i10 binder is CSLLTEVGSLLTEV (SEQ ID NO: 283), which is also recognized by Z3G1. The very best specific binder is CSLLTECGSLLTCV (SEQ ID NO: 463). The binding sequences contain a remarkably high number of cysteines.

Peptide sequences with high binding values for Z3G1 with no binding to 23K12 and BI10 were identified for low stringency (0.01 μg/mL) conditions (Table 5A) and high stringency (0.001 μg/mL) conditions (Table 5B).

TABLE 5A

| High binding values with Z3G1 NO binding 23k12 & 8i10, ■ | |
|---|---|
| CSLLCEVETPIRNE | SEQ ID NO: 1316 |
| CLL■EVECPIRNE | SEQ ID NO: 1358 |
| SLLCEVETPIRNE | SEQ ID NO: 1371 |
| CMSLLCEVETPIRNE | SEQ ID NO: 1313 |
| SLLCEVETPIRNCWG | SEQ ID NO: 1389 |
| SLLCEVETPICNEWG | SEQ ID NO: 1391 |
| MSLLLEVETPIRNEWGCRCN | SEQ ID NO: 1287 |
| CSLLCEVETPIRNE | SEQ ID NO: 1316 |
| MRLLTEVETPIRNEWGCRCN | SEQ ID NO: 1263 |
| SLLCEVETPIRCEWG | SEQ ID NO: 1390 |
| CLLTEVETPCRNEWG | SEQ ID NO: 1381 |
| SLLCEVETPIRNEWC | SEQ ID NO: 1387 |
| MSLLCEVGMSLLCEV | SEQ ID NO: 1341 |

TABLE 5B

| High binding values with Z3G1 NO binding 23k12 & 8i10, ■ | |
|---|---|
| MSLLTEVDTPIRNEWGCRCN | SEQ ID NO: 1300 |
| MSLLMEVETPIRNEWGCRCN | SEQ ID NO: 1288 |
| MSLLEEVETPIRNEWGCRCN | SEQ ID NO: 1281 |
| MSLLCEVETPIRNC | SEQ ID NO: 1325 |
| MSLLSEVETPIRNEWGCRCN | SEQ ID NO: 1293 |
| MSLLNEVETPIRNEWGCRCN | SEQ ID NO: 1289 |
| MSLLKEVETPIRNEWGCRCN | SEQ ID NO: 1286 |
| SLLCEVECPIRNEWG | SEQ ID NO: 1394 |
| MSLLAEVETPIRNEWGCRCN | SEQ ID NO: 1279 |
| MSLLDEVETPIRNEWGCRCN | SEQ ID NO: 1280 |
| MDLLTEVETPIRNEWGCRCN | SEQ ID NO: 1251 |
| MNLLTEVETPIRNEWGCRCN | SEQ ID NO: 1260 |
| Now dominant Motif occurs! | |

There is a clear difference between binding specificity between antibodies 8i10/23k12 versus Z3G1. The very best specific binder is a longer sequence than with 23k12/8i10, has no dimer topology and also no CLIPS. Among the very best specific binder is mostly the whole native sequence, MSLLTEVETPIRNEWGCRCN (SEQ ID NO: 1149). The result with 0.01 μg/ml shows that LLXEVEXPIRN (SEQ ID NO: 1594) is the core of the Z3G1 binding epitope.

Specific binding motifs can derived from 0.001 μg/ml screening. Thus, mAbs 23k12/8i10 recognize M2e peptides with SLLTE as the core of the epitope. The T residue in S-L-L-T-E differentiates binding between 23k12/8i10 and Z3G1. In contrast, mAb Z3G1 recognize M2e with LLX-EVEXPIRN (SEQ ID NO: 1594) as the core of the epitope. (Tables 6A and 6B).

TABLE 6A

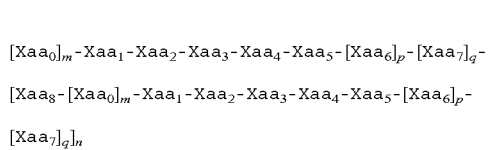

| | |
|---|---|
| CSLL ECG-SLL CV | SEQ ID NO: 1595 |
| CSLL ECGMSLL CV | SEQ ID NO: 306 |
| SLL ECG-SLL CV | SEQ ID NO: 1596 |
| MSLL ECGMCLL EV | SEQ ID NO: 489 |
| MSLL ECGMSLL CV | SEQ ID NO: 331 |
| SLL ECGCSLL EV | SEQ ID NO: 374 |

TABLE 6B 0,001 ug/ml

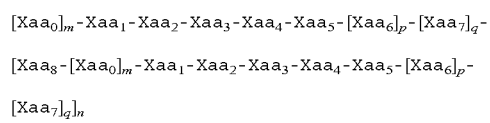

| | |
|---|---|
| MSLLTEVDTPIRNEWGCRCN | SEQ ID NO: 1300 |
| MSLLMEVETPIRNEWGCRCN | SEQ ID NO: 1288 |
| MSLLEEVETPIRNEWGCRCN | SEQ ID NO: 1281 |
| MSLLCEVETPIRNC | SEQ ID NO: 1325 |
| MSLLSEVETPIRNEWGCRCN | SEQ ID NO: 1293 |
| MSLLNEVETPIRNEWGCRCN | SEQ ID NO: 1289 |
| MSLLKEVETPIRNEWGCRCN | SEQ ID NO: 1286 |
| SLLCEVECPIRNEWG | SEQ ID NO: 1394 |
| MSLLAEVETPIRNEWGCRCN | SEQ ID NO: 1279 |
| MSLLDEVETPIRNEWGCRCN | SEQ ID NO: 1280 |
| MDLLTEVETPIRNEWGCRCN | SEQ ID NO: 1251 |
| MNLLTEVETPIRNEWGCRCN | SEQ ID NO: 1260 |

Peptide Immunogens

In particular, a peptide immunogen of this invention that binds the HuM2e 23k12/8i10 comprises a core sequence of S-L-L-T-E as well as variants, modifications and multimers thereof. Core sequences for low stringency (0.01 μg/mL) conditions (FIG. 6A) and high stringency (0.001 μg/mL) conditions (FIG. 6B) and variants thereof derived from the binding data are shown in FIGS. 6A and 6B.

In some embodiments, the core sequence comprises a first additional amino acid at the C terminal end of S-L-L-T-E-$Xaa_6$, wherein $Xaa_6$ is any amino acid, preferably V or C. (FIG. 6C)

Further, in some embodiments, the core sequence comprises a first additional amino acid at the C terminal end of S-L-L-T-E-$Xaa_6$-$Xaa_7$, wherein $Xaa_7$ is any amino acid, but preferably E. (FIG. 6C)

In some embodiments, the peptide immunogens comprise a plurality of core sequences linked by an amino acid, preferably a small amino acid such as G or A. However, amino acids such as proline, which can act as a structural disrupter in the middle of regular secondary structure elements such as alpha helices and beta sheets, are less desirable. The number of core sequences in peptide immunogens of the invention can be 1, 2, 3, 4, 5 or more. (FIG. 6D).

In some embodiments, an N-terminal amino acid $Xaa_0$ is present in the peptide immunogens. $Xaa_0$ can be any amino acid, but preferably is a cysteine. In some embodiments a N-terminal cysteine is used to cyclize the peptide immunogen. (FIG. 6E)

Peptide immunogens (linear or cyclized) with particularly strong affinity for 23K12/8I10 binding are shown in FIG. 6F.

The peptide immunogens of this invention that bind the huM2e monoclonal antibodies under high stringency conditions are represented by the following formula:

$[Xaa_0]_m$-$Xaa_1$-$Xaa_2$-$Xaa_3$-$Xaa_4$-$Xaa_5$-$[Xaa_6]_p$-$[Xaa_7]_q$-

$[Xaa_8$-$[Xaa_0]_m$-$Xaa_1$-$Xaa_2$-$Xaa_3$-$Xaa_4$-$Xaa_5$-$[Xaa_6]_p$-

$[Xaa_7]_q]_n$ wherein, m, p and q are independently 0 or 1,
n is any number between 0 and 4,
$Xaa_0$ is any amino acid, preferably C;
$Xaa_6$ is any amino acid, preferably V or C;
$Xaa_7$ is any amino acid, preferably E;
$Xaa_8$ is any amino acid not including proline, preferably G or A;
$Xaa_1$-$Xaa_2$-$Xaa_3$-$Xaa_4$-$Xaa_5$ is S-L-L-T-E,
or a peptide having a single substitution to the sequence S-L-L-T-E, the substitution selected from the group consisting of:
$Xaa_1$ is C or T;
$Xaa_2$ is A, C, F or K,
$Xaa_3$ is A, C, E, F, I, K, M, Q, S, T or V, and
$Xaa_5$ is D or C.

The peptide immunogens of this invention that bind the huM2e monoclonal antibodies under low stringency conditions are represented by the following formula:

$[Xaa_0]_m$-$Xaa_1$-$Xaa_2$-$Xaa_3$-$Xaa_4$-$Xaa_5$-$[Xaa_6]_p$-$[Xaa_7]_q$-

$[Xaa_8$-$[Xaa_0]_m$-$ general methodology of solid phase synthesis is well known in the art. Merrifield, R. B., Solid phase synthesis (Nobel lecture). Angew Chem 24:799-810 (1985) and Barany et al., The Peptides, Analysis, Synthesis and Biology, Vol. 2, Gross, E. and Meienhofer, J., Eds. Academic Press 1-284 (1980). For example, chemical reaction protocols, such as those described in U.S. Pat. Nos. 4,033,940 and 4,102,877, have been devised to produce circularized peptides. In other techniques, biological and chemical methods are combined to produce cyclic peptides. These latter methods involve first expressing linear precursors of cyclic peptides in cells (e.g., bacteria) to produce linear precursors of cyclic peptides and then adding of an exogenous agent such as a protease or a nucleophilic reagent to chemically convert these linear precursors into cyclic peptides. See, e.g., Camerero, J. A., and Muir, T. W., J. Am. Chem. Society. 121:5597 (1999); Wu, H. et al, Proc. Natl. Acad. Sci. USA, 95:9226 (1998).

Head-to-tail (backbone) peptide cyclization has been used to rigidify structure and improve in vivo stability of small bioactive peptides (see Camarero and Muir, J. Am. Chem. Soc., 121:5597-5598 (1999)). An important consequence of peptide cyclization is retention of biological activity and/or the identification of new classes of pharmacological agents. A chemical cross-linking approach was used to prepare a backbone cyclized version of bovine pancreatic trypsin inhibitor (Goldenburg and Creighton, J. Mol. Biol., 165:407-413 (1983)). Other approaches include chemical (Camarero et al., Angew. Chem. Int. Ed., 37:347-349 (1998); Tam and Lu, Prot. Sci., 7:1583-1592 (1998); Camarero and Muir, Chem. Commun., 1997:1369-1370 (1997); and Zhang and Tam, J. Am. Chem. Soc. 119:2363-2370 (1997)) and enzymatic (Jackson et al., J. Am. Chem. Soc., 117:819-820 (1995)) intramolecular ligation methods which allow linear synthetic peptides to be efficiently cyclized under aqueous conditions.

A native chemical ligation approach utilizes inteins (internal proteins) to catalyze head-to-tail peptide and protein ligation in vivo (see, for example, Evans et al., J. Biol. Chem. 274:18359-18363 (1999); Iwai and Pluckthun, FEBS Lett. 459.166-172 (1999); Wood et al., Nature Biotechnology 17:889-892 (1999); Camarero and Muir, J. Am. Chem. Soc. 121:5597-5598 (1999); and Scott et al., Proc. Natl. Acad. Sci. USA 96:13638-13643 (1999)).

The invention also encompasses isolated nucleic acid molecules comprising a sequences that encode M2e peptide immunogens of the invention. Also provided by the present invention are nucleic acid expression constructs, and host cells containing such nucleic acids, which encode M2e peptides, and variants thereof, which have at least one epitope characteristic of M2e peptide immunogens. This aspect of the invention pertains to isolated nucleic sequences encoding an M2e sequence or M2e peptide immunogen sequence as described herein, as well as those sequences readily derived from isolated nucleic molecules such as, for example, complementary sequences, reverse sequences and complements of reverse of sequences.

A related embodiment includes a nucleic acid expression construct comprising a promoter operably linked to the isolated nucleic acid molecule such that a M2e peptide immunogen or fusion protein comprising a M2e peptide immunogen as described herein is expressed in a host cell. In another embodiment, the invention provides a host cell containing such a nucleic acid expression construct. In a related embodiment, the invention provides a method for producing a peptide immunogen, comprising growing the described host cells for a time sufficient to express the peptide immunogen encoded by the nucleic acid expression construct.

Conjugated Peptide Immunogens

The approach of increasing immunogenicity of small immunogenic molecules by conjugating these molecules to large "carrier" molecules has been utilized successfully for decades (see, e.g., Goebel et al. (1939) J. Exp. Med. 69: 53). For example, many immunogenic compositions have been described in which purified capsular polymers have been conjugated to carrier proteins to create more effective immunogenic compositions by exploiting this "carrier effect." Schneerson et al. (1984) Infect. Immun. 45: 582-591).

In one aspect of the invention, method for conjugating a M2e peptide immunogen via a reactive group of an amino acid residue of the peptide immunogen to a protein/polypeptide carrier having one or more functional groups is provided. The protein/polypeptide carrier may be human serum albumin, keyhole limpet hemocyanin (KLH), immunoglobulin molecules, thyroglobulin, ovalbumin, influenza hemagglutinin, PAN-DR binding peptide (PADRE polypeptide), malaria circumsporozite (CS) protein, hepatitis B surface antigen ($HBSAg_{19-28}$), Heat Shock Protein (HSP) 65, *Bacillus* Calmette-Guerin (BCG), cholera toxin, cholera toxin mutants with reduced toxicity, diphtheria toxin, $CRM_{197}$ protein that is cross-reactive with diphtheria toxin, recombinant Streptococcal C5a peptidase, *Streptococcus pyogenes* ORF1224, *Streptococcus pyogenes* ORF1664, *Streptococcus pyogenes* ORF 2452, *Chlamydia pneumoniae* ORF T367, *Chlamydia pneumoniae* ORF T858, Tetanus toxoid, HIV gp120 T1, microbial surface components recognizing adhesive matrix molecules (MSCRAMMS), growth factor/hormone, cytokines or chemokines.

Methods for protecting a subject from infection or decreasing susceptibility of a subject to infection by one or more influenza strains/isolates or subtypes, i.e., prophylactic methods, are additionally provided. In one embodiment, a method includes administering to the subject an amount of M2e peptide immunogens that specifically bind influenza M2 effective to protect the subject from infection, or effective to decrease susceptibility of the subject to infection, by one or more influenza strains/isolates or subtypes.

Symptoms or complications of influenza infection that can be reduced or decreased include, for example, chills, fever, cough, sore throat, nasal congestion, sinus congestion, nasal infection, sinus infection, body ache, head ache, fatigue, pneumonia, bronchitis, ear infection, ear ache or death.

Peptide Immunogens as Vaccines

The peptide immunogens can be used as vaccines to generate an anti-influenza M2-mediated immune response in order to prevent influenza infections. Synthetic peptides require both stabilization and adjuvantation for the induction of an effective immune response in vivo. Various methods have been employed to protect synthetic peptide immunogens against degradation in vitro and in vivo, mediated by various processes including chemical and physical pathways. (Manning M C, et al. Pharmaceutical Research, 1989, 6:903-918).

Numerous adjuvants and/or depot-based parenteral, mucosal or transdermal delivery systems destined for use with human or veterinary vaccines have been developed to enhance the immune response. These include the use of mineral salts, water-in-oil (w/o)-emulsions, liposomes, polymeric microparticles, nanoparticles and gels/hydrogels. (Cox J C, et al. Vaccine, 1997, 15:248-256). Freund's complete adjuvant (FCA), a suspension of heat-killed *M. tuberculosis* mycobacteria in mineral oil containing a surfactant, has been recognized as one of the most powerful adjuvants. Adjuvants are well known in the art (Vaccine Design—The Subunit and Adjuvant Approach, 1995, Pharmaceutical Biotechnology, Volume 6, Eds. Powell, M. F., and Newman, M. J., Plenum Press, New York and London, ISBN 0-306-44867-X). Preferred adjuvants for use with immunogens of the present invention include aluminium or calcium salts (hydroxide or phosphate). Adjuvants may be selected from GM-CSF, 529 SE, IL-12, aluminum phosphate, aluminum hydroxide, *Mycobacterium tuberculosis, Bordetella pertussis*, bacterial lipopolysaccharides, aminoalkyl glucosane phosphate compounds, MPL™ (3-O-deacylated monophosphoryl lipid A), a polypeptide, Quil A, STIMULON™ QS-21, a pertussis toxin (PT), an *E. coli* heat-labile toxin (LT), IL-1alpha, IL-1β, IL-2, IL-4, IL-5, IL-6, IL-7, IL-8, IL-10, IL-13, IL-14, IL-15, IL-16, IL-17, IL-18, interferon-alpha, interferon-β, interferon-gamma, G-CSF, TNF-alpha and TNF-β.

Still other adjuvants include mineral oil and water emulsions, calcium salts such as calcium phosphate, aluminum salts (alum), such as aluminum hydroxide, aluminum phosphate, etc., Amphigen, Avridine, L121/squalene, D-lactide-polylactide/glycoside, pluronic acids, polyols, muramyl dipeptide, killed *Bordetella*, saponins, such as Stimulon™ QS-21 (Antigenics, Framingham, Mass.), described in U.S. Pat. No. 5,057,540, which is hereby incorporated by reference 3, and particles generated therefrom such as ISCOMS (immunostimulating complexes), *Mycobacterium tuberculosis*, bacterial lipopolysaccharides, synthetic polynucleotides such as oligonucleotides containing a CpG motif (U.S. Pat. No. 6,207,646, which is hereby incorporated by reference), a pertussis toxin (PT), or an *E. coli* heat-labile toxin (LT), particularly LT-K63, LT-R72, PT-K9/G129; see, e.g., International Patent Publication Nos. WO 93/13302 and WO 92/19265, which are/incorporated herein by reference for all purposes.

Also useful as adjuvants are cholera toxins and mutants thereof, including those described in published International Patent Application No. WO 00/18434 (wherein the glutamic acid at amino acid position 29 is replaced by another amino acid (other than aspartic acid, preferably a histidine). Similar CT toxins or mutants are described in published International Patent Application number WO 02/098368 (wherein the isoleucine at amino acid position 16 is replaced by another amino acid, either alone or in combination with the replacement of the serine at amino acid position 68 by another amino acid; and/or wherein the valine at amino acid position 72 is replaced by another amino acid). Other CT toxins are described in published International Patent Application number WO 02/098369 (wherein the arginine at amino acid position 25 is replaced by another amino acid; and/or an amino acid is inserted at amino acid position 49; and/or two amino acids are inserted at amino acid position 35 and 36).

Various methods may be employed to adjuvant synthetic peptide-based immunogens, but normally a carrier or depot system is required for effective long-term immunogenic responses. Notable examples include adsorbing the immunogen onto a mineral salt or gel. For example, encapsulating a peptide immunogen within a polymeric matrix (monolithic matrix) or gel, or layering a polymeric material around a peptide immunogen (core-shell) may be an effective strategy. Or, an immunogen may be incorporated in a liposome or vesicular type of formulation, with the immunogen either embedded in the lipid matrix or physically entrapped in the internal aqueous phase. Another strategy may employ a mineral-based, vegetable-based or animal-based oil, with an aqueous solution of the immunogen in various proportions, to prepare a water-in-oil (w/o)-emulsion or a water-in-oil-in-water (w/o/w)-double emulsion. Powell M F, et al., Pharmaceutical Biotechnology, Vol. 6, Plenum Press, New York, 1995.

Kits

It is particularly useful to use antibody binding sequences in the kit, which correspond to defined epitope sequences known to be specific for the immunogen under investigation. This kit will lead to a more specific answer than those kits used today, and hence to a better selection of immunogen vaccine therapy for the individual patient.

In an extension of this approach, one could also characterize the patient's serum by identifying the corresponding antibody binding peptides among a random display library using the aforementioned methods. This again may lead to optimisation of the epitope information, and thus to a better diagnosis.

Further, one could use the individual antibody binding sequences as (immunogen) vaccines leading to more specific (immunogen) vaccines. These antibody binding sequences could be administered in an isolated form or fused to a membrane protein of the phage display system, or to another carrier protein, which may have beneficial effect for the immunoprotective effect of the antibody binding peptide (Dalum et al., Nature Biotechnology, Vol. 17, pp. 666-669 (1999)).

The present invention relates to a kit for predicting binding of a specific antibody to at least one potential immunogen. The kit of the invention would also be useful for other screening purposes where it is desirable to test for antibody binding to peptide sequences, such as epitope variant.

In one embodiment the peptide immunogen may be immobilized on a solid support. Suitable solid support could be any chemical support, including micro titer plates, beads, capillary tubing or membranes. Each of these supports could be activated, supporting covalent, ionic or hydrophobic binding, chelation or affinity binding, or inactivated, promoting ionic or hydrophobic binding. Immobilisation could take place by attachment through covalent binding, ionic or hydrophobic binding, chelation, affinity binding, or through van der Waal bonds. A solid support could also be biological in nature, such as phages, bacteria, red blood cells or any related system allowing display of heterologous proteins or peptides.

The kit also can be used for screening different antigenic peptide sequences corresponding to structural epitopes at the same time. The kit above also can be used in a high throughput screening method for screening many samples, obtained e.g. from humans or animals, at the same time and thereby predicting which humans or animals will display an immunogenic response towards particular immunogens. Any practical combination of the number of antigenic peptide sequences and the number of humans or animals would be possible.

The following examples illustrate embodiments of the invention. It will be appreciated by one of skill in the art that the techniques disclosed in the examples which follow represent techniques discovered by the inventors to function well in the practice of the invention. However, those of skill in the art should, in light of the present disclosure, appreciate that many changes can be made in the specific embodiments which are disclosed and still obtain a like or similar result without departing from the spirit and scope of the invention.

EXAMPLES

Example 1

Identification of M2-Specific Antibodies

Mononuclear or B cells expressing three of the MAbs identified in human serum were diluted into clonal populations and induced to produce antibodies. Antibody containing supernatants were screened for binding to 293 FT cells stably transfected with the full length M2E protein from influenza strain Influenza subtype H3N2. Supernatants which showed positive staining/binding were re-screened again on 293 FT cells stably transfected with the full length M2E protein from influenza strain Influenza subtype H3N2 and on vector alone transfected cells as a control.

The variable regions of the antibodies were then rescue cloned from the B cell wells whose supernatants showed positive binding. Transient transfections were performed in 293 FT cells to reconstitute and produce these antibodies. Reconstituted antibody supernatants were screened for binding to 293 FT cells stably transfected with the full length M2E protein as detailed above to identify the rescued anti-M2E antibodies. Three different antibodies were identified: 8i10, 21B15 and 23K12.

Antibodies 21B15, 23K12, and 8I10 bound to the surface of 293-HEK cells stably expressing the M2 protein, but not to vector transfected cells (see FIG. 1). In addition, binding of these antibodies was not competed by the presence of 5 mg/ml 24-mer M2 peptide, whereas the binding of the control chimeric mouse V-region/human IgG1 kappa 14C2 antibody (hu14C2) generated against the linear M2 peptide was completely inhibited by the M2 peptide (see FIG. 1). These data confirm that these antibodies bind to conformational epitopes present in M2e expressed on the cell or virus surface, as opposed to the linear M2e peptide.

Example 2

Viral Binding of Human Anti-influenza Monoclonal Antibodies

Figure 2A:
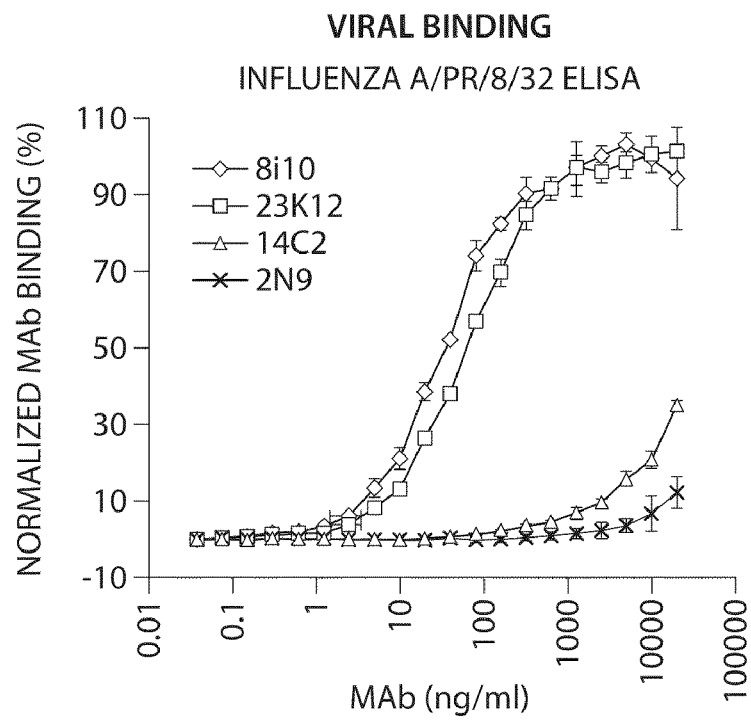
FIGS. 2A and 2B are graphs showing human monoclonal antibody binding to influenza A/PR/32.
Figure 2B:
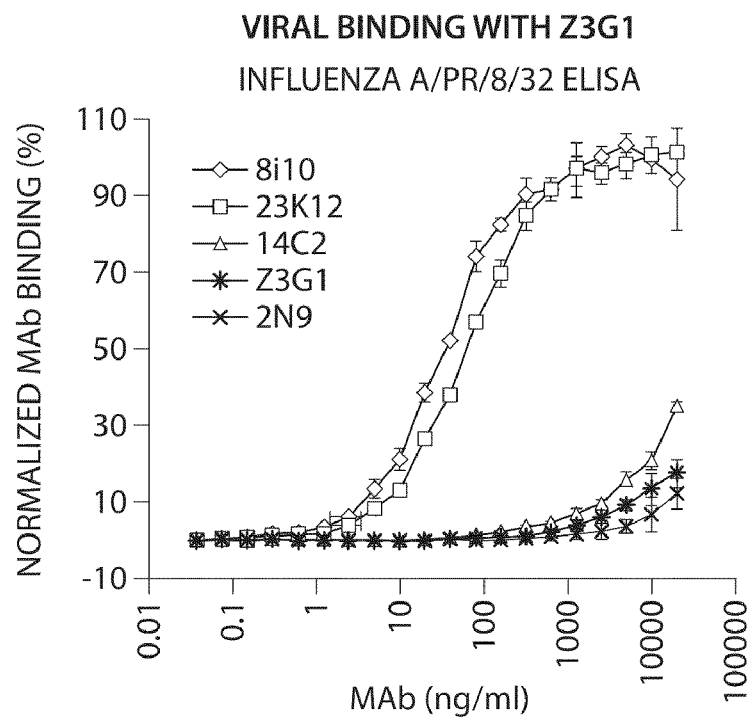

UV-inactivated influenza A virus (A/PR/8/34) (Applied Biotechnologies) was plated in 384-well MaxiSorp plates (Nunc) at 1.2 µg/ml in PBS, with 25 µl/well, and was incubated at 4° C. overnight. The plates were then washed three times with PBS, and blocked with 1% Nonfat dry milk in PBS, 50 µl/well, and then were incubated at room temp for 1 hr. After a second wash with PBS, MAbs were added at the indicated concentrations in triplicate, and the plates were incubated at room temp for 1 hour. After another wash with PBS, to each well was added 25 µl of a 1/5000 dilution of horseradish peroxidase (HRP) conjugated goat anti-human IgG Fc (Pierce) in PBS/1% Milk, and the plates were left at room temp for 1 hr. After the final PBS wash, the HRP substrate 1-Step™ Ultra-TMB-ELISA (Pierce) was added at 25 µl/well, and the reaction proceeded in the dark at room temp. The assay was stopped with 25 µl/well 1N $H_2SO_4$, and light absorbance at 450 nm (A450) was read on a SpectroMax Plus plate reader. Data are normalized to the absorbance of MAb 8I10 binding at 10 µ/ml. Results are shown in FIGS. 2A and 2B.

Example 3

Binding of Human Anti-Influenza Monoclonal Antibodies to Full-Length M2 Variants M2 variants (including those with a high pathology phenotype in vivo) were selected for analysis. See FIG. 3A for sequences.

Figure 3B:
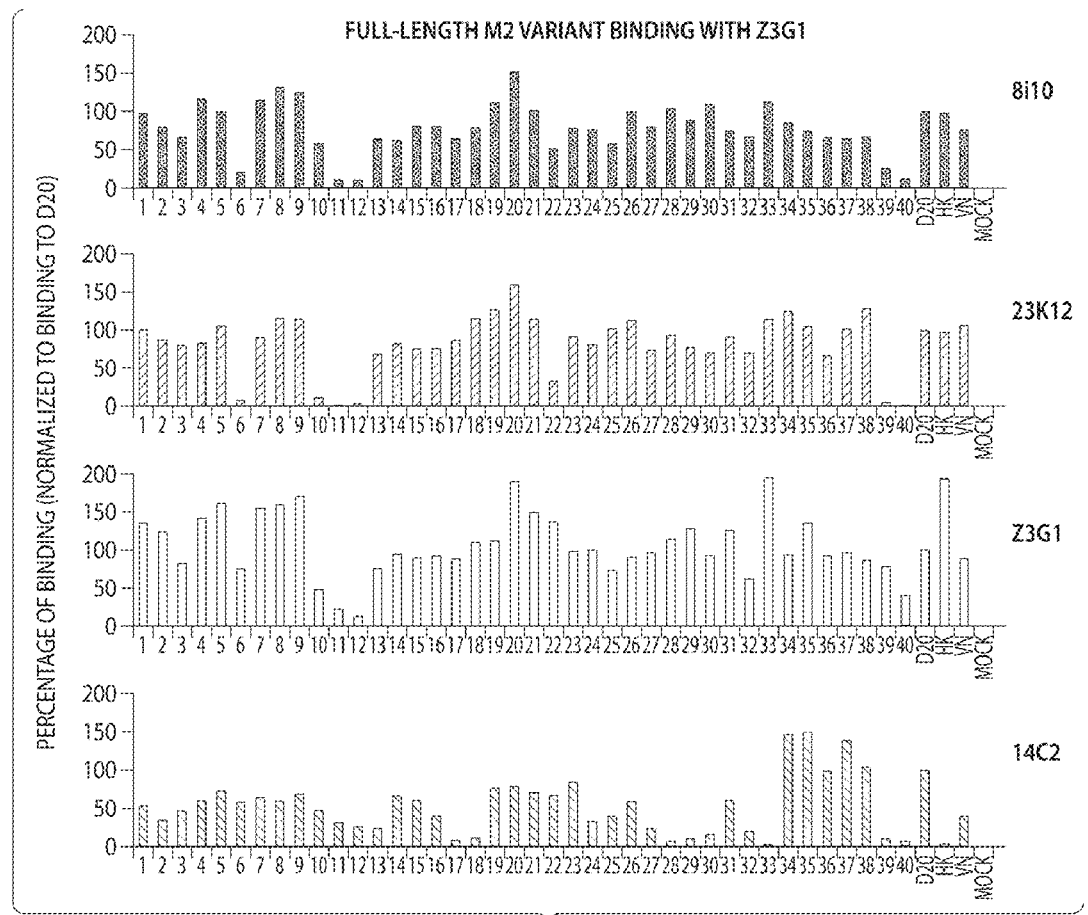
FIGS. 3B and 3C are bar charts showing binding of human monoclonal anti-influenza antibody binding to M2 variants shown in FIG. 3A.
Figure 3C:
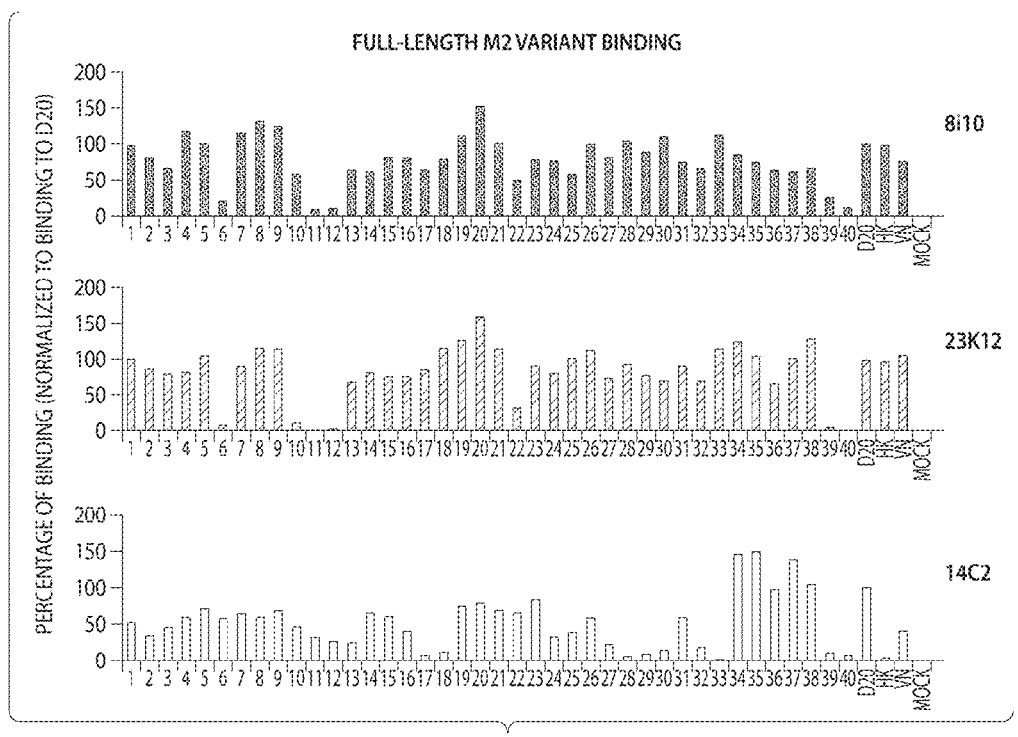

M2 cDNA constructs were transiently transfected in HEK293 cells and analyzed as follows: To analyze the transient transfectants by FACS, cells on 10 cm tissue culture plates were treated with 0.5 ml Cell Dissociation Buffer (Invitrogen), and harvested. Cells were washed in PBS containing 1% FBS, 0.2% $NaN_3$ (FACS buffer), and resuspended in 0.6 ml FACS buffer supplemented with 100 µg/ml rabbit IgG. Each transfectant was mixed with the indicated MAbs at 1 µg/ml in 0.2 ml FACS buffer, with $5 \times 10^5$ to $10^6$ cells per sample. Cells were washed three times with FACS buffer, and each sample was resuspended in 0.1 ml containing 1 µg/ml alexafluor (AF) 647-anti human IgG H&L (Invitrogen). Cells were again washed and flow cytometry was performed on a FACSCanto device (Becton-Dickenson). The data is expressed as a percentage of the mean fluorescence of the M2-D20 transient transfectant. Data for variant binding are representative of 2 experiments. Data for alanine mutants are average readouts from 3 separate experiments with standard error. Results are shown in FIGS. 3B and 3C.

Example 4

Epitope Blocking

Figure 4:
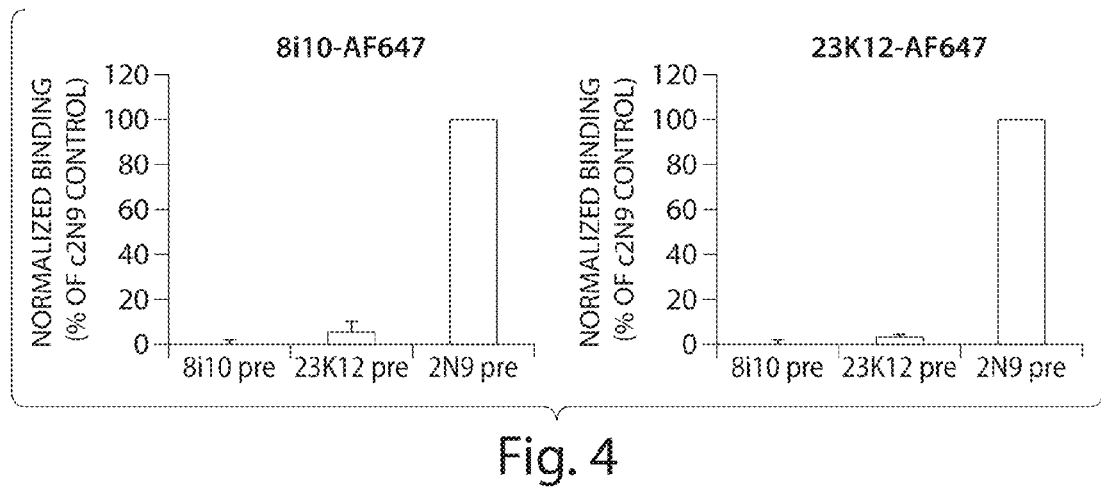
FIG. 4 is a series of bar charts showing binding of MAbs 8I10 and 23K12 to M2 protein representing influenza strain A/HK/483/1997 sequence that was stably expressed in the CHO cell line DG44.
Figure 5:
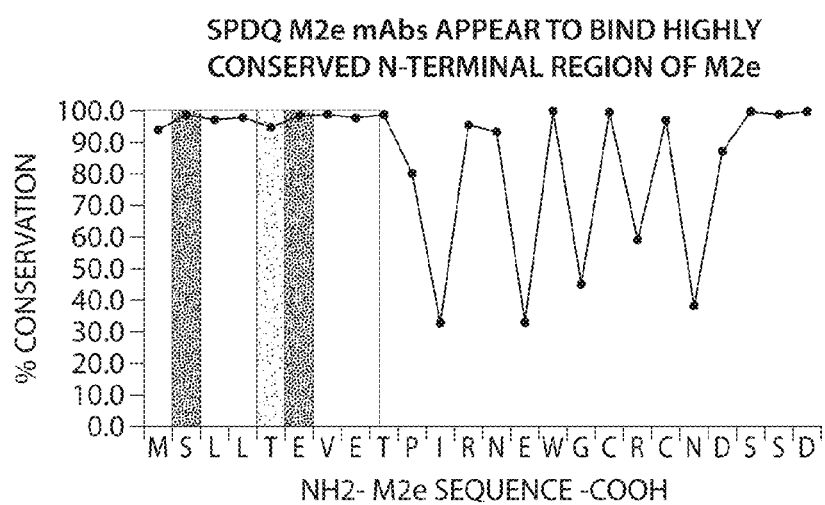
FIG. 5 is an illustration showing the anti-M2 antibodies bind a highly conserved region in the N-Terminus of M2e.

To determine whether the MAbs 8I10 and 23K12 bind to the same site, M2 protein representing influenza strain A/HK/483/1997 sequence was stably expressed in the CHO (Chinese Hamster Ovary) cell line DG44. Cells were treated with Cell Dissociation Buffer (Invitrogen), and harvested. Cells were washed in PBS containing 1% FBS, 0.2% $NaN_3$ (FACS buffer), and resuspended at $10^7$ cells/ml in FACS buffer supplemented with 100 µg/ml rabbit IgG. The cells were pre-bound by either MAb (or the 2N9 control) at 10 µg/ml for 1 hr at 4° C., and were then washed with FACS buffer. Directly conjugated AF647-8I10 or –23K12 (labeled with the AlexaFluor® 647 Protein Labeling kit (Invitrogen) was then used to stain the three pre-blocked cell samples at 1 µg/ml for $10^6$ cells per sample. Flow cytometric analyses proceeded as before with the FACSCanto. Data are average readouts from 3 separate experiments with standard error. Results are shown in FIG. 4.

Example 5

Binding of Human Anti-influenza Monoclonal Antibodies to M2 Variants and Truncated M2 Peptides The cross reactivity of mAbs 8i10 and 23K12 to other M2 peptide variants was assessed by ELISA. Peptide sequences are shown in Tables 7A and 7B. Additionally, a similar ELISA assay was used to determine binding activity to M2 truncated peptides.

In brief, each peptide was coated at 2 µg/mL to a flat bottom 384 well plate (Nunc) in 25 µL/well of PBS buffer overnight at 4° C. Plates were washed three times and blocked with 1% Milk/PBS for one hour at room temperature. After washing three times, MAb titers were added and incubated for one hour at room temperature. Diluted HRP conjugated goat anti-human immunoglobulin FC specific (Pierce) was added to each well after washing three times. Plates were incubated for one hour at room temperature and washed three times. 1-Step™ Ultra-TMB-ELISA (Pierce) was added at 25 µl/well, and the reaction proceeded in the dark at room temp. The assay was stopped with 25 µl/well 1N $H_2SO_4$, and light absorbance at 450 nm (A450) was read on a SpectroMax Plus plate reader. Results are shown in Tables 7A and 7B.

TABLE 7A

Cross reactivity binding of anti-M2 antibodies to variant M2 peptides.

| seqNo | Name | Size | Description | ELISA (OD 450) | | | |
|---|---|---|---|---|---|---|---|
| | | | | 14C2 | 8i10 | 23K12 | 2N9 |
| 1 | M2 | 23 aa | SLLTEVETPIRNEWGCRCNDSSD | + | − | − | − |
| 2 | M2SG | 23 aa | SLLTEVETPIRSEWGCRCNDSGD | + | − | − | − |
| 3 | M2EG | 23 aa | SLLTEVETPIRNEWECRCNGSSD | + | − | − | − |
| 4 | M2P | 23 aa | SLPTEVETPIRNEWGCRCNDSSD | + | − | − | − |
| 5 | M2G | 23 aa | SLLTEVETPIRNEWGCRCNGSSD | + | − | − | − |
| 6 | M2DLTGS | 23 aa | SLLTEVDTLTRNGWGCRCSDSSD | − | − | + | − |
| 7 | M2KNS | 23 aa | SLLTEVETPIRKEWGCNCSDSSD | + | − | − | − |
| 8 | M2LGS | 23 aa | SLLTEVETLIRNGWGCRCSDSSD | − | − | − | − |
| 9 | M2LTKGS | 23 aa | SLLTEVETLTKNGWGCRCSDSSD | − | − | − | − |
| 10 | M2SY | 23 aa | SLLTEVETPIRSEWGCRYNDSSD | + | − | − | − |
| 11 | M2TGEKS | 23 aa | SLLTEVETPTRNGWECKCSDSSD | + | − | − | − |
| 12 | M2HTGEKS | 23 aa | SLLTEVETHTRNGWECKCSDSSD | − | − | − | − |
| 13 | M2KTGEKS | 23 aa | SLLTEVKTPTRNGWECKCSDSSD | − | − | − | − |
| 14 | M2LTGS | 23 aa | SLLTEVETLTRNGWGCRCSDSSD | − | − | + | − |
| 15 | M2TDGEKS | 23 aa | SLLTEVETPTRDGWECKCSDSSD | + | − | − | − |
| 16 | M2TGS | 23 aa | SLLTEVETPTRNGWGCRCSDSSD | + | − | W | − |
| 17 | M2TGEK | 23 aa | SLLTEVETPTRNGWECKCNDSSD | + | − | − | − |
| 18 | M2LTGEKS | 23 aa | SLLTEVETLTRNGWECKCSDSSD | − | − | W | − |
| 19 | M2K | 23 aa | SLLTEVETPIRNEWGCKCNDSSD | + | W | + | − |
| 20 | M2FG | 23 aa | SFLTEVETPIRNEWGCRCNGSSD | + | W | − | − |
| 21 | M2TGE | 23 aa | SLLTEVETPTRNGWECRCNDSSD | + | − | − | − |
| 22 | M2KGENS | 23 aa | SLLTEVETPIRKGWECNCSDSSD | + | − | − | − |
| 23 | M2TES | 23 aa | SLLTEVETPTRNEWECRCSDSSD | + | − | − | − |
| 24 | M2GHTGKS | 23 aa | SLLTGVETHTRNGWGCKCSDSSD | − | − | − | − |
| 25 | M2PHTGS | 23 aa | SLLPEVETHTRNGWGCRCSDSSD | − | − | − | − |

Percentage compared relative to binding to wild-type peptide (Seq 1)
Note:
mAbs were tested at 5 μg/mL
>25%   − no binding
25-40% W weak binding
>40%   + positive binding

TABLE 7B

Binding activity of M2 antibodies to truncated M2 peptides.

| seqNo | Name | Size | Description | 14C2 | 8i10 | 23K12 | 2N9 |
|---|---|---|---|---|---|---|---|
| 1 | M2 | 23 aa | SLLTEVETPIRNEWGCRCNDSSD | 3.85 | 0.11 | 0.22 | 0.06 |
| 26 | M16 | 16 aa | LLTEVETPIRNEWGCR | 3.94 | 0.09 | 0.21 | 0.09 |
| 27 | M15 | 15 aa | LTEVETPIRNEWGCR | 3.95 | 0.09 | 0.21 | 0.09 |
| 28 | M12 | 12 aa | VETPIRNEWGCR | 0.15 | 0.09 | 0.20 | 0.09 |

TABLE 7B-continued

Binding activity of M2 antibodies to truncated M2 peptides.

| seqNo | Name | Size | Description | 14C2 | 8i10 | 23K12 | 2N9 |
|---|---|---|---|---|---|---|---|
| 29 | CM17 | 17 aa | ETPIRNEWGCRCNDSSD | 0.19 | 0.11 | 0.34 | 0.11 |
| 30 | CM16 | 16 aa | TPIRNEWGCRCNDSSD | 0.23 | 0.13 | 0.35 | 0.12 |
| 31 | CM15 | 15 aa | PIRNEWGCRCNDSSD | 0.19 | 0.12 | 0.34 | 0.11 |
| 32 | CM14 | 14 aa | IRNEWGCRCNDSSD | 0.23 | 0.14 | 0.36 | 0.13 |
| 33 | CM13 | 13 aa | RNEWGCRCNDSSD | 0.22 | 0.14 | 0.34 | 0.13 |
| 34 | CM12 | 12 aa | NEWGCRCNDSSD | 0.27 | 0.14 | 0.39 | 0.14 |
| 35 | NM17 | 17 aa | SLLTEVETPIRNEWGCR | 3.99 | 0.26 | 0.58 | 0.10 |
| 36 | NM16 | 16 aa | SLLTEVETPIRNEWGC | 3.90 | 0.29 | 0.62 | 0.09 |
| 37 | NM15 | 15 aa | SLLTEVETPIRNEWG | 3.97 | 0.12 | 0.30 | 0.11 |
| 38 | NM14 | 14 aa | SLLTEVETPIRNEW | 3.97 | 0.11 | 0.24 | 0.09 |
| 39 | NM13 | 13 aa | SLLTEVETPIRNE | 0.18 | 0.11 | 0.25 | 0.10 |
| 40 | NM12 | 12 aa | SLLTEVETPIRN | 0.20 | 0.10 | 0.24 | 0.09 |
| 41 | NM11 | 11 aa | SLLTEVETPIR | 0.21 | 0.13 | 0.30 | 0.12 |
| 42 | NM10 | 10 aa | SLLTEVETPI | 0.17 | 0.10 | 0.24 | 0.10 |
| 43 | NM8 | 8 aa | SLLTEVET | 0.15 | 0.10 | 0.20 | 0.09 |
| 44 | NM7 | 7 aa | SLLTEVE | 0.14 | 0.10 | 0.20 | 0.08 |
| 45 | NM9 | 9 aa | SLLTEVETP | 0.21 | 0.12 | 0.30 | 0.19 |
| 46 | M2e | 24 aa | MSLLTEVETPIRNEWGCRCNDSSD | 3.98 | 0.13 | 0.43 | 0.10 |
| CMV | HVIR1 | | | 0.16 | 0.11 | 0.21 | 3.99 |

Note:
mAbs were tested at 5 µg/mL

OTHER EMBODIMENTS

All publications and patent applications cited in this specification are herein incorporated by reference as if each individual publication or patent application is specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08329188B2). An electronic copy of the "Sequence Listing" will also be available from the USPTO upon request and payment of the fee set forth in 37 CFR 1.19(b)(3).

What is claimed:

1. A peptide immunogen consisting of the sequence of:

$[Xaa_0]_m\text{-}Xaa_1\text{-}Xaa_2\text{-}Xaa_3\text{-}Xaa_4\text{-}Xaa_5\text{-}[Xaa_6]_p\text{-}$
$[Xaa_7]_q\text{-}[Xaa_8\text{-}[Xaa_0]_m\text{-}Xaa_1\text{-}Xaa_2\text{-}Xaa_3\text{-}Xaa_4\text{-}Xaa_5\text{-}$
$[Xaa_6]_p\text{-}[Xaa_7]_q]_n$ wherein, m, p and q are independently 0 or 1,
n is any number between 1 and 4,
$Xaa_0$, $Xaa_6$, $Xaa_7$ and $Xaa_8$ is independently any amino acid,
$Xaa_1\text{-}Xaa_2\text{-}Xaa_3\text{-}Xaa_4\text{-}Xaa_5$ is S-L-L-T-E.

2. The peptide immunogen of claim 1, wherein $Xaa_0$ is C.

3. The peptide immunogen of claim 1, wherein $Xaa_6$ is V or C.

4. The peptide immunogen of claim 1, wherein $Xaa_7$ is E.

5. The peptide immunogen of claim 1, wherein $Xaa_8$ is G or A.

6. The peptide immunogen of claim 1, wherein said peptide is non-linear, and wherein said peptide is cyclic, and n is any number between 1 and 4.

7. The peptide immunogen of claim 1, wherein said peptide is a Linear or cyclized peptide having the sequence SLLTEVGSLLTEV (SEQ ID NO: 320).

* * * * *